(12) United States Patent
Schirmer et al.

(10) Patent No.: US 7,208,140 B2
(45) Date of Patent: Apr. 24, 2007

(54) TRIMERIC MACROCYCLIC SUBSTITUTED BENZENE DERIVATIVES

(75) Inventors: Heiko Schirmer, Berlin (DE);
Hanns-Joachim Weinmann, Berlin (DE); Johannes Platzek, Berlin (DE); Jose Luis Martin, Majadahonda (ES); Juan R. Harto, Madrid (ES); Bjoern Riefke, Berlin (DE)

(73) Assignee: Schering Aktiengesellschaft, Berlin (DE)

( * ) Notice: Subject to any disclaimer, the term of this patent is extended or adjusted under 35 U.S.C. 154(b) by 344 days.

(21) Appl. No.: 10/780,887

(22) Filed: Feb. 19, 2004

(65) Prior Publication Data

US 2004/0265236 A1    Dec. 30, 2004

Related U.S. Application Data

(60) Provisional application No. 60/452,053, filed on Mar. 6, 2003.

(30) Foreign Application Priority Data

Feb. 19, 2003    (DE)    ................ 103 07 759

(51) Int. Cl.
*A61B 5/055* (2006.01)
*C07F 5/00* (2006.01)
*C07D 225/00* (2006.01)
*C07D 243/14* (2006.01)

(52) U.S. Cl. ............ 424/9.363; 534/16; 540/465; 540/474

(58) Field of Classification Search ............ 424/9.363; 534/16; 540/465, 474
See application file for complete search history.

(56) References Cited

U.S. PATENT DOCUMENTS 5,403,576 A    4/1995    Lin et al. ............... 424/9
5,660,814 A    8/1997    Uggeri et al. ........... 424/9.36

FOREIGN PATENT DOCUMENTS

WO    WO 9316375    8/1993
WO    WO 9427644    12/1994

*Primary Examiner*—Brenda Coleman
(74) *Attorney, Agent, or Firm*—Millen, White, Zelano & Branigan, P.C.

(57) ABSTRACT

The metal complexes of general formula I (I)

[chemical structure: benzene ring with substituents $A^1$, $A^1$, $A^2$, and three Hal groups]

in which Hal stands for bromine or iodine and $A^1$ and $A^2$ have different meanings, are suitable as contrast media.

19 Claims, 4 Drawing Sheets

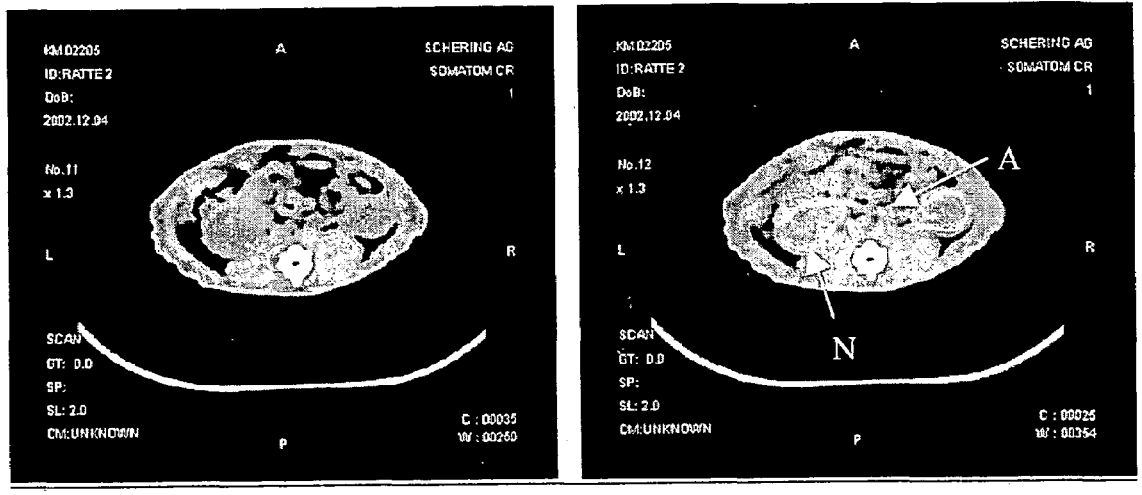
Fig. 1     a (Baseline)     b (15 sec p.i.)
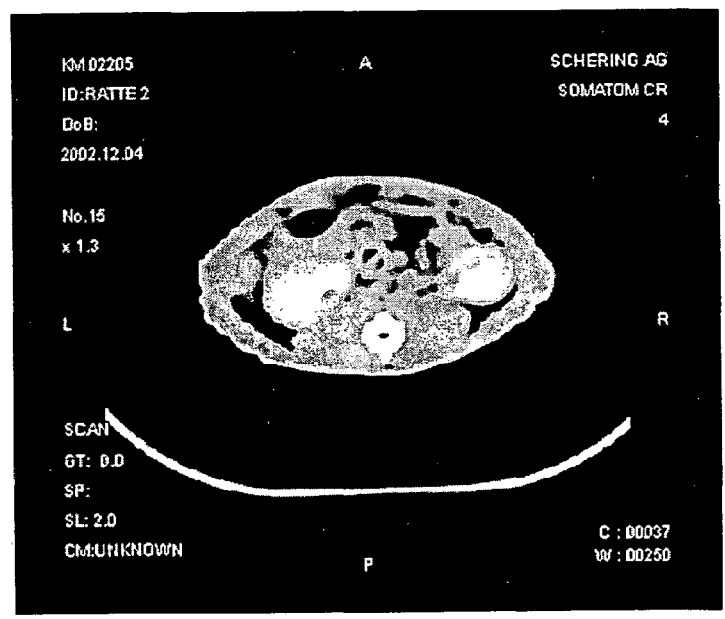
Fig. 2  CT Image of a Rat 15 Minutes after I.V. Injection of IB

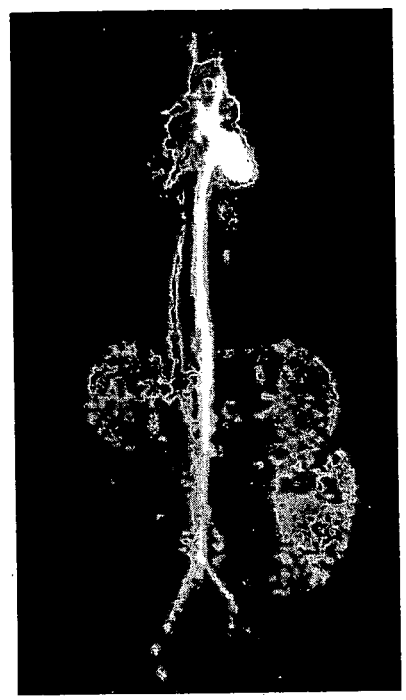
Fig. 3 MRA 7.5 Seconds After I.V. Injection of IB in Rats
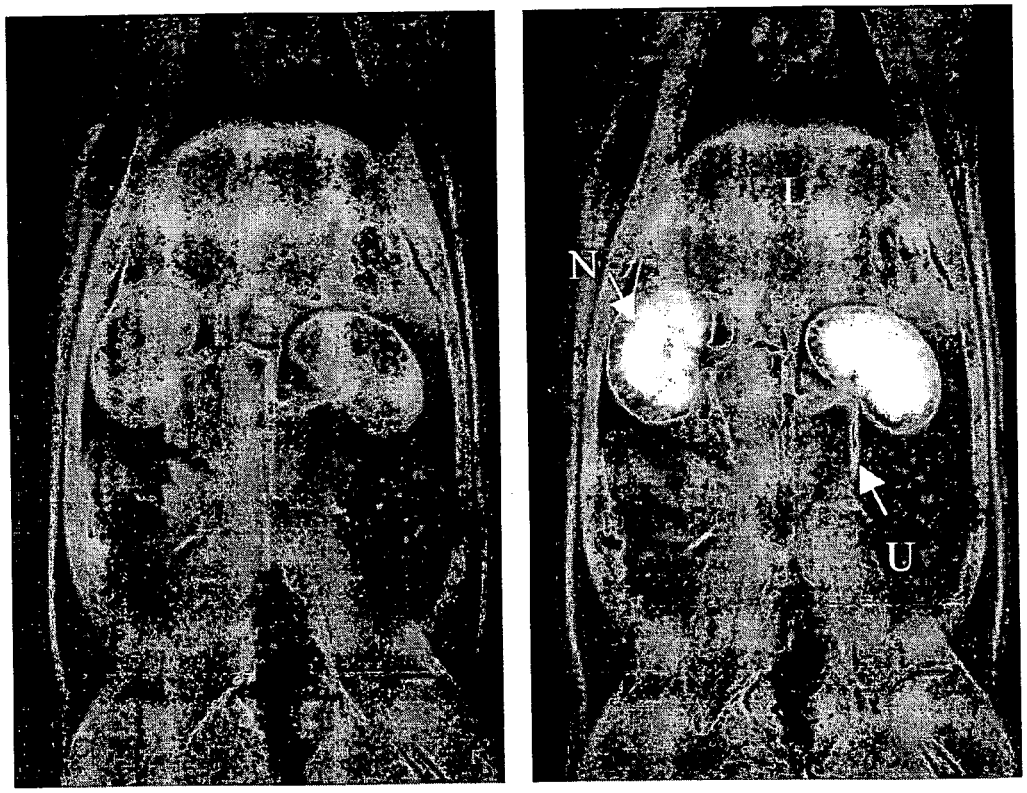
Fig. 4      a (Baseline)      b (15 min p.i.)

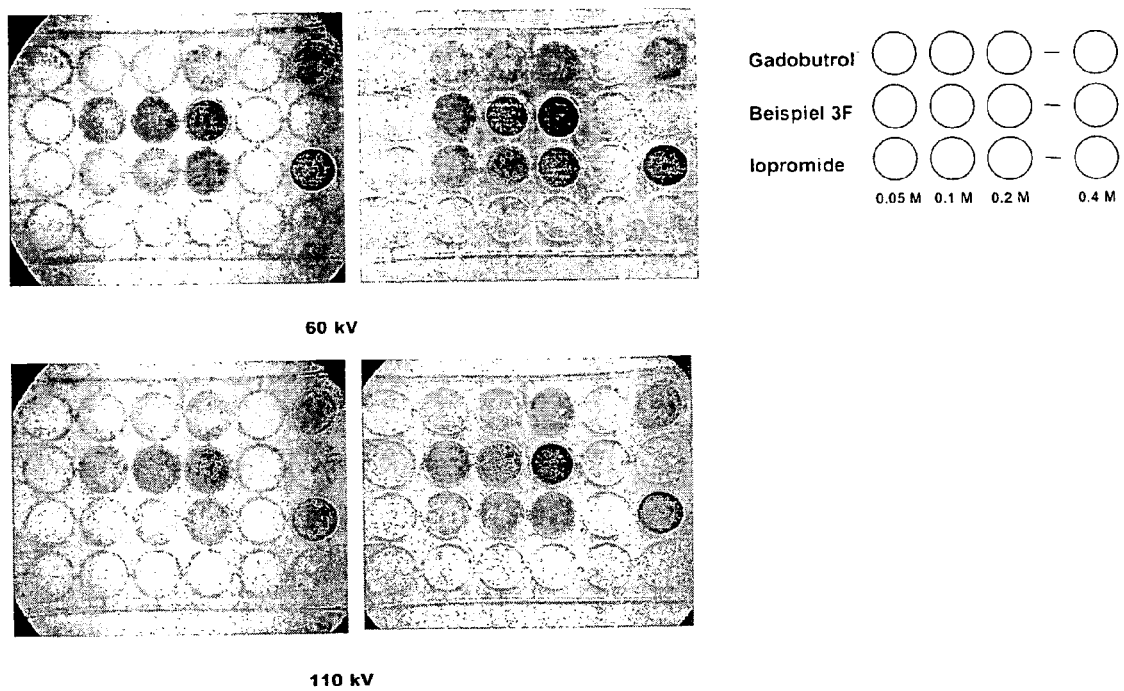
Figure 5: Comparison of X-ray Absorption of Example 3F, Gadobutrol and Iopromide X-ray images of the phantom at 60 and 110 kV anode voltage are recorded with the C-arm device stenoscope D6 (General Electric).
[Key to Fig. 5:] Beispiel 3F = Example 3F

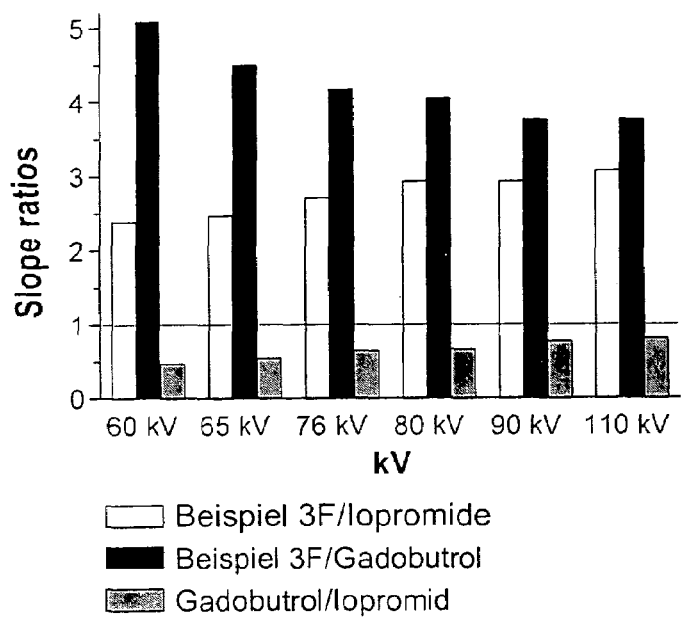
Figure 6: Relative X-ray Absorption of Example 3F in Comparison with Gadobutrol and Iopromide at Various Anode Voltages of X-ray Tubes (Stenoscope D6, General Electric).
[Key to Fig. 6:] Beispiel = Example, Ipromid = Iopromide

TRIMERIC MACROCYCLIC SUBSTITUTED BENZENE DERIVATIVES

This application claims the benefit of the filing date of U.S. Provisional Application Ser. No. 60/452,053 filed Mar. 6, 2003.

The invention relates to the subjects that are characterized in the claims: new trimeric macrocyclic substituted triiodine and tribromobenzene derivatives, their production and use as contrast media in x-ray diagnosis and MRT diagnosis.

During the last decade, impressive advances were achieved in imaging diagnosis. The imaging techniques, such as DAS, CT and MRT, have developed into standard and indispensable tools in diagnosis and interventional radiology and now offer a spatial resolution of less than 1 mm. In addition, the possible applications of these techniques are increased decisively by the use of contrast media. This now wide distribution and acceptance of the contrast media in x-ray diagnosis can be attributed to the introduction of non-ionic monomeric triiodoaromatic compounds in the 1980's, as well as the isoosmolar dimeric iodoaromatic compounds that were introduced in the 1990's. By these two compound classes, the frequency of contrast medium-induced side effects was reduced to 2–4% (Bush, W. H., Swanson, D. P.: Acute Reactions to Intravascular Contrast Media: Types, Risk Factors, Recognition and Specific Treatment. AJR 157, 1153–1161, 1991. Rydberg, J., Charles, J., Aspelin, P.: Frequency of Late Allergy-Like Adverse Reactions Following Injection of Intravascular Non-ionic Contrast Media. Acta Radiológica 39, 219–222, 1998). The use of contrast media in connection with modern imaging techniques now extends from the detection of tumors, for high-resolution vascular visualization, to the quantitative determination of physiological factors such as permeability or perfusion of organs. The concentration of the x-ray contrast medium (here the iodine atom) is decisive for the contrast and the detection sensitivity. Despite further development of the technology, it was not possible to reduce the concentration or the dose to be administered that is necessary for a medical diagnosis. Thus, in a standard CT study, 100 g of substance or more is injected per patient.

Although the compatibility of the x-ray contrast media has been improved by the introduction of non-ionic triiodobenzenes, the number of side effects is still always high. Because of very high study numbers of several million per year in x-ray diagnosis, ten thousand patients are thus affected. These contrast medium-induced side effects extend from slight reactions such as nausea, dizziness, vomiting, and hives up to severe reactions such as bronchiospasms, or renal failure up to reactions such as shock or even death. Fortunately, these severe cases are very rare and are observed at a frequency of only 1/200,000 (Morcos, S. K., Thomsen, H. S.: Adverse Reactions to Iodinated Contrast Media. Eur Radiol 11, 1267–1275, 2001).

The frequency of these side effects, which are also observed as pseudoallergic contrast medium-induced side effects, is, however, increased by about a factor of 3 in atopic patients and by a factor of 5 in patients with a previous history of contrast medium-induced side effects. Asthma increases the risk of severe contrast medium-induced side effects by a factor of 6 in non-ionic contrast media (Thomsen, H. S., Morcos, S. K.: Radiographic Contrast Media. BJU 86 (Suppl1), 1–10, 2000. Thomsen, H. S., Dorph, S.: High-Osmolar and Low-Osmolar Contrast Media. An Update on Frequency of Adverse Drug Reactions. Acta Radiol 34, 205–209, 1993. Katayama, H., Yamaguchi, K., Kozuka, T., Takashima, T., Seez, P., Matsuura, K.: Adverse Reactions to Ionic and Non-ionic Contrast Media. Radiology 175, 621–628, 1990. Thomsen, H. S., Bush, Jr., W. H.: Adverse Effects on Contrast Media. Incidence, Prevention and Management. Drug Safety 19: 313–324, 1998). Under these conditions, the examiners for x-ray diagnosis in recent years most frequently use non-iodine-containing Gd-chelates instead of the standard triiodoaromatic compounds in computer topography but also in interventional radiology as well as DSA (Gierada, D. S., Bae, K. T.: Gadolinium as CT Contrast Agent: Assessment in a Porcine Model. Radiology 210, 829–834, 1999. Spinosa, D. J., Matsumoto, A. H., Hagspiel, K. D., Angle, J. F., Hartwell, G. D.: Gadolinium-based Contrast Agents in Angiography and Interventional Radiology. AJR 173; 1403–1409, 1999. Spinosa, D. J., Kaufmann, J. A., Hartwell, G. D.: Gadolinium Chelates in Angiography and Interventional Radiology: A Useful Alternative to Iodinated Contrast Media for Angiography. Radiology 223, 319–325, 2002). This is, on the one hand, substantiated by the very good compatibility of the metal chelates that are used in MRT, but also by the known fact that lanthanides are also x-ray-opaque. In comparison to iodine, gadolinium and other lanthanides show a greater absorption than iodine especially at higher voltages/energies of the x-ray radiation, such that, in principle, they are suitable as opacifying elements for x-ray diagnosis (Schmitz, S., Wagner, S., Schuhmann-Giampieri, G., Wolf, K. J.: Evaluation of Gadobutrol in a Rabbit Model as a New Lanthanide Contrast Agent for Computer Tomography. Invest. Radiol. 30(11): 644–649, 1995).

The above-mentioned Gd-containing chelate compounds originally used in the MRT are also readily water-soluble and are distinguished by an excellent compatibility. Compared to the iodine-containing/non-ionic contrast media, the rate of light pseudoallergenic reactions is greatly reduced, the rate of fatal reactions is extremely rare and is indicated with 1/1000000 (Runge, V. M.: Safety of Approved MR Contrast Media for Intravenous Injection. J. Magn Reson Imaging 12, 205–213, 2000). In contrast to other contrast medium-induced side effects, such as, e.g., the renal compatibility, pseudoallergic reactions are more likely independent of the administered dose. Also, the smallest dosages can accordingly already trigger a pseudoallergic reaction.

Desired are substances that combine the advantages of the two chemically entirely different classes of compounds.

The extraordinarily high hydrophilia of the metal chelates suggests a low incompatibility rate. Iodoaromatic compounds have a higher lipophilia by a factor of 100–200 (larger distribution coefficient between butanol/water) than metal chelates.

Based on the low substance concentration and the low specific proportion of the imaging metal in the entire molecule, the previously known metal chelates for x-ray diagnosis are not optimal (Albrecht, T., Dawson, P.: Gadolinium-DTPA as X-ray Contrast Medium in Clinical Studies. BJR 73, 878–882, 2000). More recent attempts to solve this problem describe the production of metal complex conjugates, in which triiodoaromatic compounds are covalently bonded to an open-chain or macrocyclic metal complex (U.S. Pat. No. 5,324,503, U.S. Pat. No. 5,403,576, WO 93/16375, WO 00/75141, WO 97/01359, WO 00/71526, U.S. Pat. No. 5,660,814). Because of their low hydrophilia and high viscosity, the latter cannot be administered in adequate concentration and reasonable volumes, however.

The purpose is to produce compounds that have an adequate hydrophilia—comparable to that of Gd-chelates and in addition exhibit a high concentration of opacifying elements. Values that are significantly higher than those in metal chelates, which are approximately 25% (g/g), were desirable. In addition, at a higher concentration, a very good water solubility must be provided. In addition to their good pharmacological properties, the highly concentrated solutions must also indicate a practical viscosity and a low osmotic pressure.

This object is achieved by this invention. The metal complexes of general formula I according to the invention

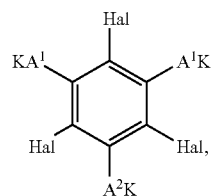

(I)

in which
Hal stands for bromine or iodine,
$A^1$ stands for the radicals
—CONR$^1$—(CH$_2$)$_n$—(CO—CHZ$^1$-NH)$_m$—CO—CHZ$^2$-*,
—CONR$^1$—(CH$_2$)$_p$—(CONR$^2$CH$_2$)$_m$—CHOH—CH$_2$—*,
—CH$_2$O—(CH$_2$)$_p$—CHOH—CH$_2$—*,
—CH$_2$—O—(CH$_2$)$_n$—NR$^1$—(CO—CHZ$^1$-NH)$_m$—CO—CHZ$^2$-*, or
—CH$_2$—NR$^1$—CO—(CHZ$^1$-NH—CO)$_m$—CHZ$^2$-*,
$A^2$ has the same meaning as $A^1$ or in the case that $A^1$ has the meaning first mentioned above can also stand for the radical —NR$^1$—CO—(NR$^1$)$_m$—(CH$_2$)$_p$—NR$^2$—(CO—CHZ$^1$-NH)$_m$—CO—CHZ$^2$-*,
in which $R^1$ and $R^2$, independently of one another, mean a hydrogen atom, a $C_1$-$C_2$-alkyl group or a monohydroxy-$C_1$-$C_2$-alkyl group,
* designates the binding site to K,
$Z^1$ and $Z^2$, independently of one another, mean a hydrogen atom or a methyl group,
n means the numbers 2–4,
m means the numbers 0 or 1 and
p means the numbers 1–4,
K stands for a macrocyclic compound of formula $I_A$

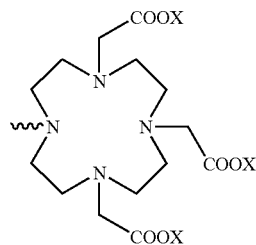

($I_A$)

with X in the meaning of a hydrogen atom or a metal ion equivalent of atomic numbers 20–29, 39, 42, 44 or 57–83, provided that at least two X stand for metal ion equivalents and optionally present free carboxy groups optionally are present as salts of organic and/or inorganic bases or amino acids or amino acid amides, show a very good solubility and a distribution coefficient that is comparable to that of Gd-chelates. In addition, the new compounds have a high specific content of opacifying elements, a low viscosity and osmolality and thus good tolerance/compatibility, so that they are extremely well suited as contrast media for x-ray and MR imaging.

Hal preferably stands for iodine, $R^1$ and $R^2$ stand for hydrogen and the methyl group, n stands for the number 2, and p stands for the number 1.

By way of example, radicals $A^1$ are mentioned:
—CONH(CH$_2$)$_{2,3}$NHCOCH$_2$NHCOCH(CH$_3$)—,
—CONH(CH$_2$)$_{2,3}$NHCOCH$_2$NHCOCH$_2$—,
—CONH(CH$_2$)$_{2,3}$NHCOCH$_2$—,
—CONH(CH$_2$)$_{2,3}$NHCOCH(CH$_3$)—,
—CONHCH$_2$CH(OH)CH$_2$—,
—CON(CH$_3$)CH$_2$CH(OH)CH$_2$—,
—CH$_2$OCH$_2$CH(OH)CH$_2$—,
—CONHCH$_2$CONHCH$_2$CH(OH)CH$_2$—,
—CH$_2$NHCOCH$_2$—,
—CH$_2$NHCOCH(CH$_3$)—,
—CH$_2$NHCOCH$_2$NHCOCH$_2$—,
—CH$_2$NHCOCH$_2$NHCOCH(CH$_3$)—,
—CH$_2$O(CH$_2$)$_2$NHCOCH$_2$—,
—CON(CH$_2$CH$_2$OH)CH$_2$CH$_2$NHCOCH$_2$—, or
—CH$_2$O(CH$_2$)$_2$N(CH$_2$CH$_2$OH)COCH$_2$—.

By way of example, radicals $A^2$ are mentioned:
—NHCOCH$_2$NHCOCH$_2$NHCOCH(CH$_3$)—,
—NHCOCH$_2$NHCOCH$_2$NHCOCH$_2$—,
—NHCOCH$_2$NHCOCH$_2$—,
—NHCOCH$_2$NHCOCH(CH$_3$)—,
—N(CH$_3$)COCH$_2$NHCOCH$_2$—,
—NHCONH(CH$_2$)$_2$NHCOCH$_2$—,
—NHCOCH$_2$N(CH$_2$CH$_2$OH)COCH$_2$—, or
—N(CH$_3$)COCH$_2$N(CH$_2$CH$_2$OH)COCH$_2$—.

The compounds of general formula I according to the invention can be produced according to the process that is known by one skilled in the art, by, for example,
a) a triiodo- or tribromoaromatic compound of general formula II

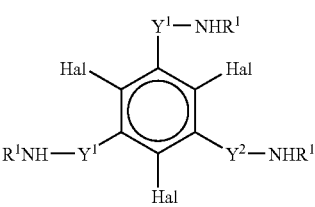

(II)

being reacted in a way that is known in the art with a macrocyclic compound of general formula III

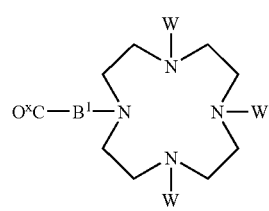

(III)

in which

C$^x$O stands for a —COOH or activated carboxyl group,

W stands for a protective group or a —CH$_2$COOX' group with X' in the meaning of X or a protective group and —Y$^1$—NR$^1$—CO—B$^1$— stands for the radical A$^1$ in the meaning of —CO—NR$^1$—(CH$_2$)$_n$—NR$^2$—(CO—CHZ$^1$-NH)$_m$—CO—CHZ$^2$- or —CH$_2$—O—(CH$_2$)$_n$—NR$^1$—(CO—CHZ$^1$-NH)$_m$—CO—CHZ$^2$- and —Y$^2$—NR$^1$—CO—B$^1$— for —Y$^1$—NR$^1$—CO—B$^1$- or for the case that —Y$^1$—NR$^1$—CO—B$^1$— has the meaning first mentioned above, the latter also stands for —NR$^1$—CO—(NR$^1$)$_m$(CH$_2$)$_p$—NR$^2$—(CO—CHZ$^1$-NH)$_m$—CO—CHZ$^2$-, whereby B$^1$ means the radical on the first or second (viewed from K) carbonyl group between —CO— and K, and Y$^1$ or Y$^2$ stands for the deficient radical of the linker group that is reduced by one imino group, and then optionally protective group W being removed and the radical CH$_2$COOX being introduced in a way that is known in the art or the protective group that optionally stands for X' being removed and then reacted in a way that is known in the art with a metal oxide or metal salt of an element of atomic numbers 20–29, 39, 42, 44 or 57–83 or b) a triiodo- or tribromoaromatic compound of general formula IV

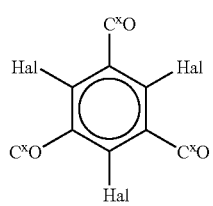

being reacted in a way that is known in the art with a macrocyclic compound of general formula V

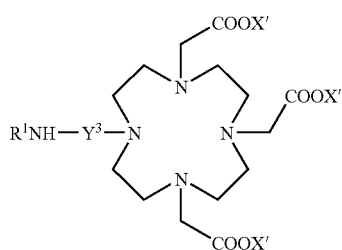

in which —C$^x$O and X' have the above-mentioned meaning, and —CO—NR$^1$—Y$^3$—stands for radical A$^1$ in the meaning of —CONR$^1$—(CH$_2$)$_p$—(CONR$^2$CH$_2$)$_m$—CH(OH)CH$_2$— and thus Y$^3$ is in the meaning of —NR$^1$—(CH$_2$)$_p$—(CONR$^2$CH$_2$)$_m$—CH(OH)CH$_2$—, and then the protective group that optionally stands for X' being removed and then being reacted in a way that is known in the art with a metal oxide or metal salt of an element of atomic numbers 20–29, 39, 42, 44 or 57–83 or c) a triiodo- or tribromoaromatic compound of general formula VI

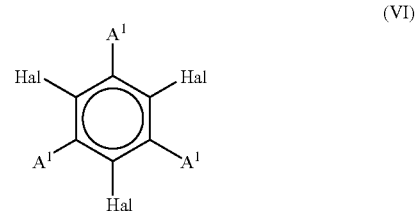

in which

A$^1$ stands for a radical

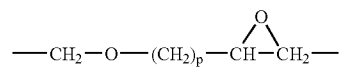

being reacted in a way that is known in the art with a cyclene of general formula VII

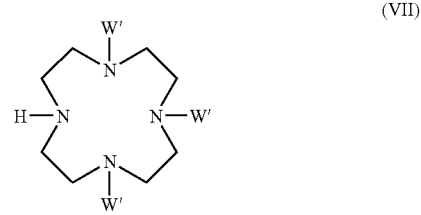

in which W' stands for a hydrogen atom or a protective group, (after the optionally present protective groups have been removed and then radical —CH$_2$COOX has been introduced in a way that is known in the art) to form a metal complex of general formula I with A in the meaning of radical —CH$_2$—O—(CH$_2$)$_p$—CHOH—CH$_2$— or d) a triiodo- or tribromoaromatic compound of general formula VIII

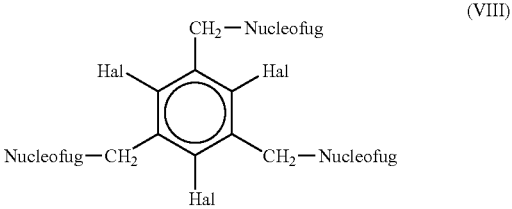

[Nucleofug = nucleofuge]

in which nucleofuge stands for a nucleofuge group, being reacted in a way that is known in the art with a macrocyclic compound of general formula IX

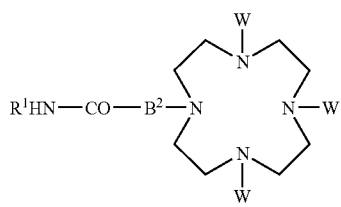

(IX)

in which

R[1] and W have the above-mentioned meanings, and B[2] stands for the radical —$(CHZ^1\text{-}NHCO)_m$—$CHZ^2$- and then being further processed as indicated under a), such that metal complexes of general formula I are obtained with A[1] in the meaning of radical —$CH_2$—$NR^1$—CO—$(CHZ^1\text{-}NHCO)_m$—$CHZ^2$, whereby then optionally in the metal complexes, obtained according to a)–d), of general formula I, still present acid hydrogen atoms are substituted by cations of inorganic or organic bases, amino acids or amino acid amides.

As amino protective groups W, the benzyloxycarbonyl, tert-butoxycarbonyl, trifluoroacetyl, fluorenylmethoxycarbonyl, benzyl, formyl, 4-methoxybenzyl, 2,2,2-trichloroethoxycarbonyl, phthaloyl, 1,2-oxazoline, tosyl, dithiasuccinoyl, allyloxycarbonyl, sulfate, pent-4-enecarbonyl, 2-chloroacetoxymethyl (or ethyl) benzoyl, tetrachlorophthaloyl, and alkyloxycarbonyl groups that are familiar to one skilled in the art can be mentioned [Th. W. Greene, P. G. M. Wuts, Protective Groups in Organic Syntheses, 2nd Ed., John Wiley and Sons (1991), pp. 309–385; E. Meinjohanns et al, J. Chem. Soc. Perkin Trans 1, 1995, 405; U. Ellensik et al, Carbohydrate Research 280, 1996, 251; R. Madsen et al, J. Org. Chem. 60, 1995, 7920; R. R. Schmidt, Tetrahedron Letters 1995, 5343].

The cleavage of the protective groups is carried out according to the process that is known to one skilled in the art (see, e.g., Wünsch, Methoden der Org. Chemie [Methods of Organic Chemistry], Houben-Weyl, Vol. XV/1, 4th Edition 1974, p. 315), for example by hydrolysis, hydrogenolysis, alkaline saponification of esters with alkali in aqueous-alcoholic solution at temperatures from 0° C. to 50° C., acidic saponification with mineral acids, or in the case of Boc groups with the aid of trifluoroacetic acid.

Activated carboxyl groups are defined above as those carboxyl groups that are derivatized, such that they facilitate the reaction with an amine. Which groups can be used for activation is known, and reference can be made to, for example, M. and A. Bodanszky, "The Practice of Peptide Synthesis," Springerverlag 1984. Examples are aducts of carboxylic acid with carbodiimides or activated esters, such as, e.g., hydroxybenzotriazole ester, acid chloride, N-hydroxysuccinimide ester,

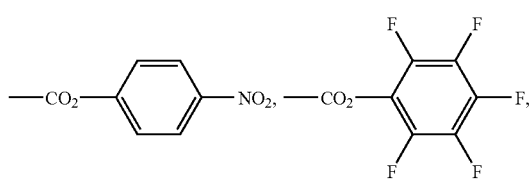

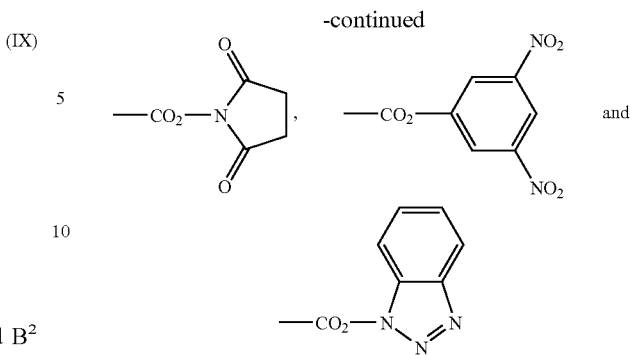

4-nitrophenyl ester and N-hydroxysuccinimide ester are preferred.

The activated esters of the above-described compounds are produced as known to one skilled in the art. Also, the reaction-with correspondingly derivatized esters of N-hydroxysuccinimide, such as, for example:

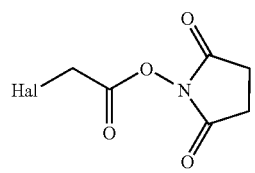

is possible (Hal=halogen).

In general, all commonly used activation methods for carboxylic acids that are known in the prior art can be used for this purpose. The activation of carboxylic acid is carried out according to commonly used methods. Examples of suitable activating reagents are dicyclohexylcarbodiimide (DCC), 1-ethyl-3-(3-dimethylaminopropyl)-carbodiimide-hydrochloride (EDC), benzotriazol-1-yloxytris(dimethylamino)-phosphoniumhexafluorophosphate (BOP) and O-(benzotriazol-1-yl)-1,1,3,3-tetramethyluroniumhexafluorophosphate (HBTU), preferably DCC. Also, the addition of O-nucleophilic catalysts, such as, e.g., N-hydroxysuccinimide (NHS) or N-hydroxybenzotriazole, is possible.

Advantageously used as nucleofuges are the radicals:
F, Cl, Br, I, —OTs, —OMs, OH,

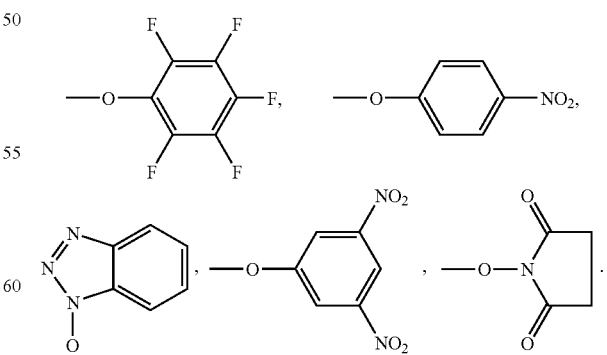

If X stands for an acid protective group, lower alkyl, aryl and aralkyl groups, for example the methyl, ethyl, propyl, butyl, phenyl, benzyl, diphenylmethyl, triphenylmethyl, and bis-(p-nitrophenyl)-methyl group, as well as trialkylsilyl groups, are suitable.

The t-butyl group and the benzyl group are preferred.

The cleavage of the protective groups is carried out according to the process that is known to one skilled in the art (see, e.g., Wünsch, Methoden der Org. Chemie, Houben-Weyl, Volume XV/1, 4$^{th}$ Edition 1974, p. 315), for example, by hydrolysis, hydrogenolysis, alkaline saponification of esters in aqueous-alcoholic solution at temperatures of 0° C. to 50° C., acidic saponification with mineral acids or in the case of tert-butyl esters with the aid of trifluoroacetic acid (Protective Groups in Organic Synthesis, 2$^{nd}$ Edition, T. W. Greene and P. G. M. Wuts, John Wiley and Sons Inc., New York, 1991).

The introduction of the desired metal ions can be carried out as was disclosed in Patents EP 71564, EP 130934 and DE-OS 34 01 052. To this end, the metal oxide or a metal salt (for example, a chloride, nitrate, acetate, carbonate or sulfate) of the desired element is dissolved or suspended in water and/or a lower alcohol (such as methanol, ethanol or isopropanol) and reacted with the solution or suspension of the equivalent amount of the complexing agent.

The neutralization of optionally still present free carboxy groups is carried out with the aid of inorganic bases (e.g., hydroxides, carbonates or bicarbonates) of, e.g., sodium, potassium, lithium, magnesium or calcium and/or organic bases, such as, i.a., primary, secondary and tertiary amines, such as, e.g., ethanolamine, morpholine, glucamine, N-methyl- and N,N-dimethylglucamine, as well as basic amino acids, such as, e.g., lysine, arginine, and ornithine or amides of original neutral or acidic amino acids.

For the production of neutral complex compounds, for example in acidic complex salts in aqueous solution or suspension, enough of the desired base can be added to reach the neutral point. The solution that is obtained can then be evaporated to the dry state in a vacuum. It is frequently advantageous to precipitate the neutral salts that are formed by adding water-miscible solvents, such as, e.g., lower alcohols (methanol, ethanol, isopropanol, etc.), lower ketones (acetone, etc.), polar ethers (tetrahydrofuran, dioxane, 1,2-dimethoxyethane, etc.) and thus to obtain easily isolated and readily purified crystallizates. It has proven especially advantageous to add the desired base as early as during the complexing of the reaction mixture and thus to save a process step.

The purification of the thus obtained complexes is carried out, optionally after the pH is set to 6 to 8, preferably about 7, by adding an acid or base, preferably by ultrafiltration with membranes of a suitable pore size (e.g., Amicon®YM1, Amicon® YM3), gel filtration on, e.g., suitable Sephadex® gels or by HPLC on silica gel or reverse-phase material.

A purification can also be carried out by crystallization from solvents such as methanol, i-propanol, acetone or their mixtures with water.

In the case of neutral complex compounds, it is frequently advantageous to add the oligomer complexes via an anion exchanger, for example IRA 67 (OH$^-$ form), and optionally in addition via a cation exchanger, for example IRC 50 (H$^+$ form), to separate ionic components.

The production of the compounds of general formula I according to the invention can be carried out as indicated above:

a) The reaction of triiodo- or tribromoaromatic compounds of general formula II with compounds of general formula III is carried out according to the process of amide formation that is known to one skilled in the art.

In this connection, either a direct coupling of the free acid of III with the free amine of II can be performed with dehydrating reagents, such as dicyclohexylcarbodiimide, diisopropylcarbodiimide, EDC, EEDQ, TBTU, or HATU in aprotic solvents such as DMF, DMA, THF, dioxane, toluene, chloroform or methylene chloride at temperatures of 0°–50° C., or else the acid group is activated in the compound of general formula III, by its first being converted into an active ester (see page 11) and then these esters in a solvent, such as, for example, DMF, DMA, THF, dioxane, dichloromethane, i-ProOH, or toluene, optionally with the addition of an organic or inorganic base, such as NEt$_3$, pyridine, DMAP, Hünig base, Na$_2$CO$_3$, or CaCO$_3$, being reacted at temperatures of –10° to +70° C. with the amine of general formula II.

In some cases, it has proven advantageous to produce the metal complexes of general formula III directly and to couple their terminal carboxylic acid under the process that is mentioned in WO 98/24775.

The production of the metal complexes is described in WO 98/24774.

The production of compounds of general formula II is carried out in the case when Y$^2$ stands for Y$^1$ by reactions of compounds of general formula IV

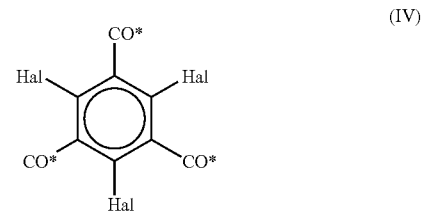

(IV)

with diamines of general formula A

(A)

in which Hal, CO*, R$^1$, R$^2$, and m are in the above-indicated meaning, according to the methods of amide formation known to one skilled in the art (see above) in an aprotic solvent such as DMF, DMA, THF, dioxane, 1,2-dichloroethane, chloroform, dichloromethane or toluene, optionally with the addition of an organic or inorganic base, such as NEt$_3$, pyridine, DMAP, Hünig base, Na$_2$CO$_3$, K$_2$CO$_3$, or CaCO$_3$, at temperatures of 0° C.–100° C.

In many cases, it has proven advantageous to use diamine itself as a solvent. Many times, it may be advantageous to use one of the two terminal amino groups in protected form (e.g., Mono-Boc, Mono-Z) and, after coupling is completed, to cleave this protective group according to the methods known to one skilled in the art (T. W. Greene, see above).

The diamines or mono-protected diamines are known in the literature and can be purchased (e.g., Aldrich, Fluka). The acid chloride of the compound of general formula IV is preferably used.

The production of the compound

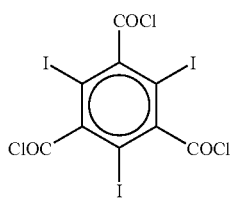

is described in DE 3001292.

The production of the corresponding tri-bromine compound is carried out analogously from tribromoaminoisophthalic acid by Sandmeyer reaction (introduction of CN and subsequent saponification) as described in EP 0073715.

In the case that $Y^2$ is not equal to $Y^1$, the following procedure has proven worthwhile:

The compounds of general formula B

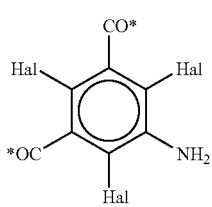

in which CO* and Hal are in the above-mentioned meaning, are first reacted with compounds of general formula C

CO*—(CHZ$^1$)-NH—Sg        (C)

in which CO* and $Z^1$ have the above-mentioned meaning, and Sg stands for an amino protective group.

The reaction is carried out according to the methods of amide formation that are already indicated above (Neher et al, Helv. Chim. Acta, 1946, 1815.)

Then, as already described above, it is reacted with compounds of general formula A and then optionally present amino protective groups are cleaved (see T. W. Greene).

It has proven advantageous to use the acid chlorides of general formula C.

If Sg represents a trifluoroacetyl protective group, the latter is cleaved directly in a single-pot process with excess diamine of general formula A.

Compounds of general formula C can be obtained according to methods that are known in the literature.

For the production of urea derivatives, compounds of general formula B are first reacted with isocyanates of general formula D

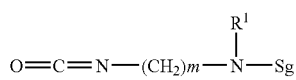

O=C=N—(CH$_2$)$_m$—N—Sg        (D)
                    |
                    R$^1$ and then further reacted as described above with the diamines of the general formula.

The reaction of the isocyanates is carried out in aprotic solvents as described above for amide formation. The reaction temperature is 0° C. to 100° C.

Isocyanates (D) are produced as described in, e.g., Guichard et al., J. Org. Chem., 1999, 8702.

Compounds of general formula B are described in DE 3001292.

b) The reaction of compounds of general formula IV with compounds of general formula V is carried out according to the methods of amide formation that are known to one skilled in the art, as were already previously described in detail under a).

Also here, the acid chloride of compounds IV is preferably used.

Compounds of general formula V are obtained from compounds of

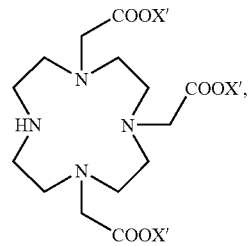

general formula E in which X' is in the above-mentioned meaning, by reaction with primary epoxides of general formula F

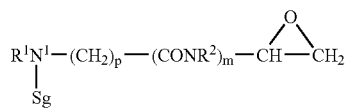

in which $R^1$, Sg, p, m, and $R^2$ are in the above-mentioned meanings. The reaction is carried out in protic or aprotic solvents, such as methanol, ethanol, butanol, propanol, DMF, toluene, CHCl$_3$, or DMA (optionally in each case with the addition of water) at temperatures of 0° C. to 15° C. In some cases, the addition of a Lewis acid, such as LiCl, LiBr, LiJ, LiClO$_4$ or Y(triflate)$_3$, has proven worthwhile.

Compounds of general formula F are accessible according to methods that are known in the literature (Krawiecka et al., J. Chem. Soc. Perkin Trans. 1, 2001, 1086) or can be purchased.

Compounds of general formula E are so-called DO3A derivatives and are described in the literature (Chatal et al., Tetrahedron Lett., 1996, 7515).

c) The reaction of epoxides of general formula VI with compounds of general formula VII is carried out according to the methods of the reaction of epoxides with amines that are described under b).

In some cases, it has proven advantageous to use the method described in EP 0545511 with use of the compound

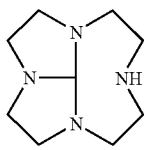

Action can also be taken, however, according to EP 0643705, or the lithium process that is described under WO 98/55467 can be used.

The production of compounds VI in the case of the W'-protective group, see b), is known in the literature.

The TriBoc-cyclene compound is described in Kimura et al., J. Am. Chem. Soc., 1997, 3068, and the tri Z-cyclene compound is described in Delaney et al., J. Chem. Soc., Perkin Trans., 1991, 3329.

Compounds of general formula VI are accessible by reaction of triols of general formula G

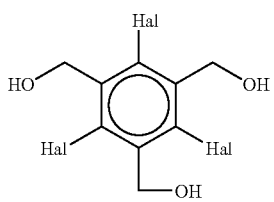

(G)

with epoxides of general formula H

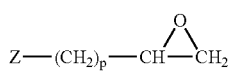

(H)

with p in the above-mentioned meaning and in which Z stands for Cl, Br, I, or $OT_S$.

The reaction is carried out according to methods of glycide ether formation (p=1) or etherification that are known in the literature, Mouzin et al., Synthesis, 1983, 117.

Compounds of general formula H are known in the literature, e.g., Sharpless et al., J. Org. Chem., and DE 935433 or can be purchased (e.g., epichlorohydrin, Fluka, Aldrich).

Compounds of general formula G in the case of Hal=iodine are described in U.S. Pat. No. 6,310,243. The production of the bromine compound is carried out analogously.

d) The reaction is carried out such that first the amide of the compounds of general formula IX is deprotonated according to the method that is known to one skilled in the art, e.g., with NaH in DMF, THF, DMA, dioxane, toluene (temperatures of 0° C.–100° C.) or BuLi, LDA, Li-HMDS, Na-HMDS in THF, MTB at temperatures of −70° to 0° C. and then reacted with compounds of general formula VIII (preferred temperatures of −70 to 70° C.).

Compounds of general formula VIII are obtained from compounds of general formula G

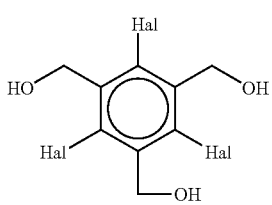

(G)

according to the methods that are known to one skilled in the art for converting a primary OH group into a halide or tosylate, triflate, etc.

Compounds of general formula IX are obtained from compounds of general formula IXa

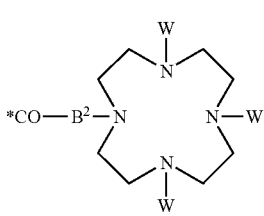

IXa by amide formation with amines of formula $R^1NH_2$ (amides of the formula are commercially available or known in the literature) according to the methods of amide coupling already mentioned under a).

Compounds of general formula IXa are described in, e.g., WO 97/02051, WO 99/16757 or can be produced simply from tri-Boc cyclene or tri-Z-cyclene according to methods that are known in the literature.

The compounds according to the invention can be used both in x-ray diagnosis and in MR diagnosis.

The high x-ray opacity paired with the good water-solubility of the iodized x-ray contrast media is combined with the intense hydrophilia of metal chelates and good compatibility in a molecule that is inherent in them. The very high hydrophilia of the new compounds results in that the side-effect profile corresponds to that of the very well-tolerated Gd compounds, as they are used in MR imaging. This property therefore makes it especially suitable for use in patients with a proven allergy to iodized compounds or in the case of existing atopy. In particular, the incidence of severe side effects such as bronchiospasms and shock or even death is reduced to the low level of the MR contrast medium.

The low osmolality of the formulations is an indication of a generally very good compatibility of the new compounds. They are therefore especially suitable for intravascular (parenteral) uses.

Depending on the pharmaceutical formulation, the contrast media can be used exclusively for x-ray diagnosis (triiodine complexes with diamagnetic metals), but also simultaneously for x-ray diagnosis and MRT diagnosis (triiodine complexes with paramagnetic atoms, preferably Gd). The compounds can very advantageously be used in, e.g., urography, computer tomography, angiography, gastrography, mammography, cardiology and neuroradiology. Even in the case of radiation therapy, the complexes that are used are advantageous. The compounds are suitable for all perfusion measurements. A differentiation of areas that are well supplied with blood and ischemic areas is possible after intravascular injection. Quite generally, these compounds can be used in all indications where conventional contrast media are used in x-ray diagnosis or MR diagnosis.

The new contrast media can also be used fo the magnetization-transfer technique (see, e.g., Journ. Chem. Phys. 39(11), 2892 (1963), as well as WO 03/013616), if they contain mobile protons in their chemical structure. This is the case, for example, in the hydroxyl group-containing compounds, as they are described in Example 5 (page 41), Example 6 (page 44), Example 7 (page 47) and Example 8 (page 50). This application document thus also comprises contrast media that are suitable in principle for this special MRI technique.

The contrasting of cerebral infarctions and tumors of the liver or space-occupying processes in the liver as well as of tumors of the abdomen (including the kidneys) and the muscle-skeleton system is especially valuable diagnostically. Based on the low osmotic pressure, the blood vessels can be visualized especially advantageously after intraarterial or else intravenous injection.

If the compound according to the invention is intended for use in MR diagnosis, the metal ion of the signaling group must be paramagnetic. These are in particular the divalent and trivalent ions of the elements of atomic numbers 21–29, 42, 44 and 58–70. Suitable ions are, for example, the chromium(II), iron(II), cobalt(II), nickel(II), copper(II), praseodymium(III), neodymium(III), samarium(III) and ytterbium(III) ion. Because of their strong magnetic moment, gadolinium(III), terbium(III), dysprosium(III), holmium(III), erbium(III), iron(III) and manganese(II) ions are preferred; gadolinium(III) and manganese(II) ions are especially preferred.

If the compound according to the invention is intended for use in x-ray diagnosis, the metal ion is preferably derived from an element of a higher atomic number to achieve an adequate absorption of the x-rays. It was found that for this purpose, diagnostic agents that contain a physiologically compatible complex salt with metal ions of elements of atomic numbers 25, 26 and 39 as well as 57–83 are-suitable.

Preferred are manganese(II), iron(II), iron(III), praseodymium(III), neodymium(III), samarium(III), gadolinium(III), ytterbium(III) or bismuth(III) ions, especially dysprosium(III) ions and yttrium(III) ions.

The production of the pharmaceutical agents according to the invention is carried out in a way that is known in the art by the complex compounds according to the invention—optionally with the addition of the additives that are commonly used in galenicals—being suspended or dissolved in aqueous medium and then the suspension or solution optionally being sterilized. Suitable additives are, for example, physiologically harmless buffers (such as, for example, tromethamine), additives of complexing agents or weak complexes (such as, for example, diethylenetriaminepentaacetic acid or the Ca complexes that correspond to the metal complexes according to the invention) or—if necessary—electrolytes such as, for example, sodium chloride, or—if necessary—antioxidants, such as, for example, ascorbic acid.

If suspensions or solutions of the agents according to the invention in water or physiological salt solution are desired for enteral or parenteral administration or other purposes, they are mixed with one or more adjuvant(s) that are commonly used in galenicals [for example, methyl cellulose, lactose, mannitol] and/or surfactant(s) [for example, lecithins, Tween®, Myrj®] and/or flavoring substance(s) for taste correction [for example, ethereal oils].

In principle, it is also possible to produce the pharmaceutical agents according to the invention without isolating the complexes. In any case, special care must be taken to perform the chelation so that the complexes according to the invention are virtually free of noncomplexed metal ions that have a toxic effect.

This can be ensured, for example, with the aid of color indicators such as xylenol orange by control titrations during the production process. The invention therefore also relates to the process for the production of complex compounds and their salts. As a final precaution, there remains purification of the isolated complex.

In the in-vivo administration of the agents according to the invention, the latter can be administered together with a suitable vehicle, such as, for example, serum or physiological common salt solution and together with another protein such as, for example, human serum albumin (HSA).

The agents according to the invention are usually administered parenterally, preferably i.v. They can also be administered intraarterially or interstitially/intracutaneously, depending on whether a vessel/organ is to be visualized selectively contrasted (e.g., visualization of the coronary arteries after intraarterial injection) or tissue or pathologies (e.g., diagnosis of cerebral tumors after intravenous injection).

The pharmaceutical agents according to the invention contain preferably 0.001–1 mol/l of the above-mentioned compound and are generally dosed in amounts of 0.001–5 mmol/kg.

The agents according to the invention meet the many requirements for suitability as contrast media for magnetic resonance tomography. After oral or parenteral administration by increasing the signal intensity, they are extremely well suited for enhancing the informational value of the image-that is obtained with the aid of an MR tomograph. They also show the high effectiveness that is necessary to load the body with the minimum possible amounts of foreign substances and the good compatibility that is necessary to maintain the non-invasive nature of the studies. The high effectiveness (relaxivity) of the paramagnetic compounds according to the invention is of great advantage for use in magnetic resonance tomography. Thus, the relaxivity (L/mmol$^{-1}$*sec$^{-1}$ of gadolinium-containing compounds is generally 2 to 4× greater than in conventional Gd complexes (e.g., gadobutrol).

The good water solubility and low osmolality of the agents according to the invention makes it possible to produce highly concentrated solutions, so as to keep the volume burden of the circulatory system within reasonable limits and to offset the dilution by bodily fluids. In addition, the agents according to the invention exhibit not only high stability in-vitro, but also surprisingly high stability in-vivo, so that a release or an exchange of the ions, which are inherently toxic and are bonded in the complexes, is carried out only extremely slowly within the time that it takes for the new contrast media to be completely excreted.

In general, the agents according to the invention are dosed for use as MRT diagnostic agents in amounts of 0.001–5 mmol of Gd/kg, preferably 0.005–0.5 mmol of Gd/kg.

The agents according to the invention are extremely well suited as x-ray contrast media, whereby it is especially to be emphasized that with them, no signs of the anaphylaxis-like reactions that are known from the iodine-containing contrast media can be detected in biochemical-pharmacological studies. In the case of strong x-ray absorption, they are especially effective in areas of higher tube voltages (e.g., CT and DSA).

In general, the agents according to the invention are dosed for administration as x-ray contrast media analogously to, for example, meglumine-diatrizoate, in amounts of 0.01–5 mmol/kg, preferably 0.02–1 mmol of substance/kg, which corresponds to 0.06–6 mmol (I+Dy)/kg in the case of, e.g., iodine—Dy compounds.

Depending on the diagnostic requirement, formulations can be selected that can be used both in x-ray diagnosis and in MR diagnosis. To achieve optimal results for both imaging modalities, it may be advantageous to select formulations in which the proportion of paramagnetic ions is reduced, since for many MR diagnostic applications, a point of diminishing returns is reached with too high a proportion of paramagnetic ions.

For dual uses, formulations can be used in which the proportion, in percent, of paramagnetic substances (e.g., Gd) is reduced to 0.05 to 50, preferably to 2–20%. As an example, a cardiac diagnostic application can be mentioned. For the examination, a formulation that consists of the substances according to the invention in a total concentration of, e.g., 0.25 mol/l is used. The proportion of Gd-containing complexes is 20%, the remaining 80% of the metals are, e.g., Dy atoms. In an x-ray coronary angiography after intra-arterial or intravenous administration, e.g., 50 ml is used, i.e., 0.18 mmol of substance per kg of body weight in a patient who weighs 70 kg. Shortly after x-ray visualization of the coronary vessels has taken place, an MR diagnosis of the heart is followed to be able to differentiate vital myocardial areas from necrotic myocardial areas. The amount of about 110 μmol of Gd/kg previously administered for the test is optimal for this purpose.

EXAMPLE 1 a) 1,3,5-Triiodotrimesic acid-N,N,N-tris-(2-aminoethyl)amide

A solution of 10 g (15.5 mmol) of 1,3,5-triiodotrimesic acid trichloride (DE 3001292, Schering AG, priority: Jan. 11, 1980) in 100 ml of tetrahydrofuran is added in drops to 24 g (400 mmol) of ethylenediamine for 1 hour at room temperature and stirred for 14 more hours. The solid that accumulates is filtered off, rewashed with ethanol, taken up in 100 ml of water, and the solution that is produced is set at a pH of 8.0 with 1 M lithium hydroxide solution. After concentration by evaporation in a vacuum, it is recrystallized from ethanol.

Yield: 7.8 g (70% of theory) of a colorless solid Elementary analysis: Cld.: C, 25.23; H, 2.96; N, 11.77; I, 53.31. Fnd.: C, 25.46; H, 2.99; N, 11.68; I, 52.98.

b) 1,3,5-Triiodotrimesic acid-N,N,N-tris-(3,6-diaza-4,7-dioxo-8-methyloctane-1,8-diyl-{10-[1,4,7-tris-(carboxylatomethyl)-1,4,7,10-tetraazacyclododecanyl, Gd-complex]})amide 48.5 g (77.09 mmol) of the Gd complex of 10-[4-carboxy-1-methyl-2-oxo-3-azabutyl]-1,4,7,10-tetraazacyclododecane-1,4,7-triacetic acid (WO 98/24775, Schering AG, (Example 1)) is suspended in 400 ml of DMSO and mixed with 9.8 g (84.8 mmol) of N-hydroxysuccinimide and 16.7 g (81 mmol) of dicyclohexylcarbodiimide and preactivated for 1 hour. Then, it is mixed with 12.3 g (17.12 mmol) of 1,3,5-triiodotrimesic acid-N,N,N-tris-(2-aminoethyl)-amide and stirred for 3 days at room temperature under nitrogen. Insoluble components are filtered out, and the solution is poured into 2000 ml of acetone. The solid that accumulates in this case is filtered off and washed in portions with 1000 ml of acetone and with 500 ml of diethyl ether. The residue is taken up in 500 ml of water and absorptively precipitated for 2 hours with 100 g of ion exchanger (IRA 67 OH-form) and filtered off. Then, it is absorptively precipitated for 2 hours with 30 g of ion exchanger (IR 267 H-form), filtered off, mixed with 2 g of activated carbon, heated for 2 hours to 60° C., filtered off, and the solution is concentrated by evaporation to 100 ml. To remove the residual dimethyl sulfoxide, the solution is poured into 1000 ml of acetone, and the precipitate that accumulates is filtered off. The residue is dissolved in 250 ml of water, and with a little ion exchanger (H-form and OH-form), the conductivity is set at a value of 0.005 mS (pH=7.0), filtered off and concentrated by evaporation in a vacuum.

Yield: 33.9 g (73% of theory) of a colorless solid Water content (Karl-Fischer): 5.9% Elementary analysis (relative to the anhydrous substance): Cld.: C, 33.92; H, 4.15; N, 11.54; I, 14.93; Gd, 18.51. Fnd.: C, 33.99; H, 4.17; N, 11.49; I, 14.88; Gd, 18.37.

EXAMPLE 2

1,3,5-Triiodotrimesic acid-N,N,N-tris-(3,6-diaza-4,7-dioxooctane-1,8-diyl-{10-[1,4,7-tris-(carboxylatomethyl)-1,4,7,10-tetraazacyclododecanyl, Gd complex]})amide 9.4 g (15.3 mmol) of the Gd complex of 10-[4-carboxy-2-oxo-3-azabutyl]-1,4,7,10-tetraazacyclododecane-1,4,7-triacetic-acid (WO 98/24775, Schering-AG, (Example 11)) is suspended in 100 ml of DMSO and mixed with 1.96 g (17 mmol) of N-hydroxysuccinimide and 3.3 g (16 mmol) of dicyclohexylcarbodiimide and preactivated for 1 hour. Then, it is mixed with 2.4 g (3.36 mmol) of 1,3,5-triiodotrimesic acid-N,N,N-tris-(2-aminoethyl)-amide and stirred for 3 days at room temperature under nitrogen. Insoluble components are filtered out, and the solution is poured into 1000 ml of acetone. The solid that accumulates in this case is filtered off and washed in portions with 300 ml of acetone and with 100 ml of diethyl ether. The residue is taken up in 200 ml of water and absorptively precipitated for 2 hours with 30 g of ion exchanger (IRA 67 OH-form) and filtered off. Then, it is absorptively precipitated for 2 hours with 10 g of ion exchanger (IR 267 H-form), filtered off, mixed with 2 g of activated carbon, heated for 2 hours to 60° C., filtered off, and the solution is concentrated by evaporation to 100 ml. To remove the residual dimethyl sulfoxide, the solution is poured into 1000 ml of acetone, and the precipitate that accumulates is filtered off. The residue is dissolved in 250 ml of water, and with a little ion exchanger (H-form and OH-form), the conductivity is set to a value of 0.005 mS (pH=7.0), filtered off and concentrated by evaporation in a vacuum.

Yield: 6.0 g (68% of theory) of a colorless solid Water content (Karl-Fischer): 5.4% Elementary analysis (relative to the anhydrous substance): Cld.: C, 33.06; H, 3.98; N, 11.73; I, 15.18; Gd, 18.82. Fnd.: C, 33.31; H, 4.02; N, 11.70; I, 15.09; Gd, 18.74.

EXAMPLE 3 a) 1,4,7-Tris-(benzyloxycarbonyl)-10-(ethoxycarbonylmethyl)-1,4,7,10-tetrazacyclododecane 68.2 g (118.6 mmol) of 1,4,7-tris-(benzyloxycarbonyl)-1,4,7,10-tetrazacyclododecane (Delaney et al., *J Chem. Soc. Perkin Trans.* 1991, 3329) is dissolved in 700 ml of acetonitrile and mixed with 75.4 g (545.5 mmol) of sodium carbonate. Then, 39.6 g (355.5 mmol) of bromoacetic acid ethyl ester is added while being stirred vigorously, and it is heated for 20 hours to 40° C. Insoluble components are filtered out, evaporated to the dry state and chromatographed on silica gel (mobile solvent: ethyl acetate/hexane 20:1). The fractions that contain the product are combined and concentrated by evaporation.

Yield: 72.3 g (92% of theory) of a colorless oil Elementary analysis: Cld.: C, 65.44; H, 6.71; N, 8.48. Fnd.: C, 65.51; H, 6.78; N, 8.43.

b) 1,4,7-Tris-(benzyloxycarbonyl)-10-(carboxymethyl)-1,4,7,10-tetrazacyclododecane 34 g (51.4 mmol) of 1,4,7-tris-(benzyloxycarbonyl)-10-(ethoxycarbonylmethyl)-1,4,7,10-tetrazacyclododecane is dissolved in 300 ml of dioxane and mixed with 144 ml of 5% aqueous NaOH solution and stirred for 24 hours at room temperature. After neutralization with concentrated HCl, it is evaporated to the dry state. The residue is taken up in 250 ml of ethyl acetate and extracted twice with 250 ml each of 1N HCl solution. The organic phase is dried on sodium sulfate, and the solvent is evaporated to the dry state.

Yield: 27.8 g (85% of theory) of a colorless solid Elementary analysis: Cld.: C, 64.54; H, 6.37; N, 8.86. Fnd.: C, 64.47; H, 6.41; N, 8.79.

c) 1,3,5-Triiodotrimesic acid-N,N,N-tris-(3-aza-4-oxopentane-1,5-diyl-{10-[1,4,7-tris-(benzyloxycarbonyl)-1,4,7,10-tetrazacyclododecanyl]})-amide 44.6 g (70.6 mmol) of 1,4,7-tris-(benzyloxycarbonyl)-10-(carboxymethyl)-1,4,7,10-tetrazacyclododecane, 21 ml (164 mmol) of triethylamine, 14.6 g (70.5 mmol) of dicyclohexylcarbodiimide and 8.1 g (70.5 mmol) of N-hydroxysuccinimide are added to a suspension of 16.8 g (23.5 mmol) of 1,3,5-triiodotrimesic acid-N,N,N-tris-(2-aminoethyl)amide in 446 ml of DMF, and it is stirred for 20 hours at room temperature. Insoluble components are filtered out, and it is evaporated to the dry state. The residue is taken up in 500 ml of ethyl acetate and extracted twice with 500 ml each of water. The organic phase is dried on sodium sulfate, the solvent is evaporated to the dry state, and the residue is chromatographed on silica gel (mobile solvent: dichloromethane/methanol 20:1). The fractions that contain the product are combined and concentrated by evaporation.

Yield: 23.3 g (39% of theory) of a colorless solid Elementary analysis: Cld.: C, 54.93; H, 5.32; N, 9.86; I, 14.88. Fnd.: C, 55.11; H, 5.37; N, 9.81; I, 14.76.

d) 1,3,5-Triiodotrimesic acid-N,N,N-tris-(3-aza-4-oxopentane-1,5-diyl-{1-[1,4,7,10-tetrazacyclododecanyl]})-amide 20 g (7.8 mmol) of 1,3,5-triiodotrimesic acid-N,N,N-tris-(3-aza-4-oxopentane-1,5-diyl-{10-[1,4,7-tris-(benzyloxycarbonyl)-1,4,7,10-tetrazacyclododecanyl]})-amide is mixed at 0–5° C. carefully [with] 140 ml of HBr/AcOH (33%) and stirred for 3 hours at room temperature. Then, the reaction mixture is poured into 800 ml of diethyl ether, the solid that accumulates in this case is suctioned off and rewashed several times with diethyl ether. The residue is dissolved in 100 ml of water and 100 ml of dichloromethane and, while being stirred vigorously, 32% NaOH solution is added until a pH of 10 is reached. The organic phase is separated, the aqueous phase is extracted three times with 50 ml each of dichloromethane, the combined organic phases are dried on magnesium sulfate and evaporated to the dry state.

Yield: 10.3 g (97% of theory) of a colorless solid Elementary analysis: Cld.: C, 40.01; H, 6.04; N, 18.66; I, 28.18. Fnd.: C, 40.19; H, 6.07; N, 18.60; I, 28.11.

e) 2,4,6-Triiodotrimesic acid-N,N,N-tris-(3-aza-4-oxopentane-1,5-diyl-{10-[1,4,7-tris-(carboxymethyl)-1,4,7,10-tetrazacyclodecanyl]})-amide 18.6 g (13.7 mmol) of 1,3,5-triiodotrimesic acid-N,N,N-tris-(3-aza-4-oxopentane-1,5-diyl-{1-[1,4,7,10-tetrazacyclododecanyl]})-amide is dissolved in 75 ml of water, 19.5 g (206.5 mmol) of chloroacetic acid is added, and a pH of 9.5 is set at 60° C. with 32% NaOH. It is heated for 10 hours to 70° C., whereby the pH of the reaction mixture is readjusted continuously to 9.5. After cooling to room temperature, a pH of 1 is set with concentrated HCl, and the solution is concentrated by evaporation in a vacuum. The residue is absorptively precipitated with 250 ml of methanol, insoluble components are filtered out, and the filtrate is concentrated by evaporation. The residue is dissolved in 100 ml of water and added to an ion-exchange column (600 ml, IR 120, H$^+$-form). Then, it is washed with 2 l of water, and the acidic eluate is concentrated by evaporation. The residue is dissolved in 70 ml of methanol and added in drops in 900 ml of diethyl ether, the solid that accumulates in this case is suctioned off, rewashed several times with diethyl ether and dried in a vacuum.

Yield: 13.8 g (54% of theory) of a colorless solid Elementary analysis: Cld.: C, 40.39; H, 5.33; N, 13.46; I, 20.32. Fnd.: C, 40.51; H, 5.39; N, 13.38; I, 20.36.

f) 2,4,6-Triiodotrimesic acid-N,N,N-tris-(3-aza-4-oxopentane-1,5-diyl-{10-[1,4,7-tris-(carboxylatomethyl)-1,4,7,10-tetrazacyclododecanyl, Gd complex]})amide 13 g (6.9 mmol) of 2,4,6-triiodotrimesic acid-N,N,N-tris-(3-aza-4-oxopentane-1,5-diyl-{10-[1,4,7-tris-(carboxymethyl)-1,4,7,10-tetrazacyclododecanyl]})-amide is dissolved in 100 ml of water and acidified by adding 3 ml of acetic acid. 3.7 g (10.4 mmol) of gadolinium oxide is added, and it is refluxed for 6 hours. After complexing is completed, a pH of 7.4 is set with ammonia and chromatographed on silica gel (mobile solvent: dichloromethane/methanol/ammonia: –10/10/1). The fractions that contain the product are combined and absorptively precipitated with 10 g of ion exchanger (IR 267 H-form) for 2 hours and filtered off, then absorptively precipitated with 10 g of ion exchanger (IRA 67 OH-form) for 2 hours, filtered off, mixed with 2 g of activated carbon, heated for 2 hours to 60° C., filtered off and freeze-dried.

Yield: 6.2 g (36% of theory) of a colorless solid Water content (Karl-Fischer): 6.2% Elementary analysis (relative to the anhydrous substance): Cld.: C, 32.39; H, 3.88; N, 10.79; I, 16.30; Gd, 20.20. Fnd.: C, 32.44; H, 3.89; N, 10.71; I, 16.33; Gd, 20.07.

g) 2,4,6-Triiodotrimesic acid-N,N,N-tris-(3-aza-4-oxopentane-1,5-diyl-{10-[1,4,7-tris-(carboxylatomethyl)-1,4,7,10-tetrazacyclododecanyl, Dy complex]})amide 13 g (6.9 mmol) of 2,4,6-triiodotrimesic acid-N,N,N-tris-(3-aza-4-oxopentane-1,5-diyl-{10-[1,4,7-tris-(carboxymethyl)-1,4,7,10-tetrazacyclododecanyl]})-amide is dissolved in 100 ml of water and acidified by adding 3 ml of acetic acid. 3.88 g (10.4 mmol) of dysprosium oxide is added, and it is refluxed for 6 hours. After complexing is completed, the pH is set at 7.4 with ammonia, and it is chromatographed on silica gel (mobile solvent: dichloromethane/methanol/ammonia: 10/10/1). The fractions that contain the product are combined and absorptively precipitated with 10 g of ion exchanger (IR 267 H-form) for 2 hours and filtered off, then absorptively precipitated with 10 g of ion exchanger (IRA 67 OH-form) for 2 hours, filtered off, mixed with 2 g of activated carbon, heated for 2 hours to 60° C., filtered off and freeze-dried.

Yield: 7.0 g (41% of theory) of a colorless solid Water content (Karl-Fischer): 5.9% Elementary analysis (relative to the anhydrous substance): Cld.: C, 32.18; H, 3.86; N, 10.72; I, 16.19; Dy, 20.73. Fnd.: C, 32.32; H, 3.91; N, 10.67; I, 16.11; Dy, 20.68.

h) 2,4,6-Triiodotrimesic acid-N,N,N-tris-(3-aza-4-oxopentane-1,5-diyl-{10-[1,4,7-tris-(carboxylatomethyl)-1,4,7,10-tetrazacyclododecanyl, Y complex]})amide 13 g (6.9 mmol) of 2,4,6-triiodotrimesic acid-N,N,N-tris-(3-aza-4-oxopentane-1,5-diyl-{10-[1,4,7-tris-(carboxymethyl)-1,4,7,10-tetrazacyclododecanyl]})-amide is dissolved in 100 ml of water and acidified by adding 3 ml of acetic acid. 3.72 g (10.4 mmol) of yttrium carbonate is added, and it is refluxed for 6 hours. After the complexing is completed, it is set at pH, 7.4 with ammonia and chromatographed on silica gel (mobile solvent: dichloromethane/methanol/ammonia: 10/10/1). The fractions that contain the product are combined and absorptively precipitated with 10 g of ion exchanger (IR 267 H-form) for 2 hours and filtered off, then absorptively precipitated with 10 g of ion exchanger (IRA 67 OH-form) for 2 hours, filtered off, mixed with 2 g of activated carbon, heated for 2 hours to 60° C., filtered off and freeze-dried.

Yield: 6.5 g (42% of theory) of a colorless solid Water content (Karl-Fischer): 4.8% Elementary analysis (relative to the anhydrous substance): Cld.: C, 35.51; H, 4.26; N, 11.38; I, 17.87; Y, 12.52. Fnd.: C, 35.73; H, 4.31; N, 11.31; I, 17.79; Y, 12.60.

EXAMPLE 4 a) 1,4,7-Tris-(benzyloxycarbonyl)-10-(1-ethoxycarbonylethyl)-1,4,7,10-tetrazacyclododecane 50.1 g (87.0,mmol) of 1,4,7-tris-(benzyloxycarbonyl)-1,4,7,10-tetrazacyclododecane (Delaney et al., *J. Chem. Soc. Perkin Trans.* 1991, 3329) is dissolved in 500 ml of acetonitrile and mixed with 55.5 g (400 mmol) of sodium carbonate. Then, while being stirred vigorously, 54.3 g (300 mmol) of 1-bromopropionic acid ethyl ester is added, and it is heated for 20 hours to 60° C. Insoluble components are filtered out, evaporated to the dry state and chromatographed on silica gel (mobile solvent: ethyl acetate/hexane 20:1). The fractions that contain the product are combined and concentrated by evaporation.

Yield: 46 g (78% of theory) of a colorless oil. Elementary analysis: Cld.: C, 65.86; H, 6.87; N, 8.30. Fnd.: C, 65.99; H, 6.88; N, 8.23.

b) 1,4,7-Tris-(benzyloxycarbonyl)-10-(1-carboxyethyl)-1,4,7,10-tetrazacyclododecane 33.7 g (50 mmol) of 1,4,7-tris-(benzyloxycarbonyl)-10-(1-ethoxycarbonylethyl)-1,4,7,10-tetrazacyclododecane is dissolved [in] 300 ml of dioxane and mixed with 140 ml of 5% aqueous NaOH solution and stirred for 24 hours at room temperature. After neutralization with concentrated HCl, it is evaporated to the dry state. The residue is taken up in 250 ml of ethyl acetate and extracted twice with 250 ml each of 1N HCL solution. The organic phase is dried on sodium sulfate, and the solvent is evaporated to the dry state.

Yield: 28.2 g (87% of theory) of a colorless solid Elementary analysis: Cld.: C, 65.00; H, 6.55; N, 8.66. Fnd.: C, 65.22; H, 6.59; N, 8.60.

c) 1,3,5-Triiodotrimesic acid-N,N,N-tris-(3-aza-1-methyl-4-oxopentane-1,5-diyl-{10-[1,4,7-tris-(benzyloxycarbonyl)-1,4,7,10-tetrazacyclododecanyl]})-amide 45.6 g (70.6 mmol) of 1,4,7-tris-(benzyloxycarbonyl)-10-(1-carboxyethyl)-1,4,7,10-tetrazacyclododecane, 21 ml (164 mmol) of triethylamine, 14.6 g (70.5 mmol) of dicyclohexylcarbodiimide and 8.1 g (70.5 mmol) of N-hydroxysuccinimide are added to a suspension of 16.8 g (23.5 mmol) of 1,3,5-triiodotrimesic acid-N,N,N-tris-(2-aminoethyl)amide in 450 ml DMF, and it is stirred for 20 hours at room temperature. Insoluble components are filtered out and evaporated to the dry state. The residue is taken up in 500 ml of ethyl acetate and extracted twice with 500 ml each of water. The organic phase is dried on sodium sulfate, the solvent is evaporated to the dry state, and the residue is chromatographed on silica gel (mobile solvent: dichloromethane/methanol 20:1). The fractions that contain the product are combined and concentrated by evaporation.

Yield: 24.5 g (40% of theory) of a colorless solid Elementary analysis: Cld.: C, 55.43; H, 5.47; N, 9.70; I, 14.64. Fnd.: C, 55.49; H, 5.43; N, 9.66; I, 14.60.

d) 1,3,5-Triiodotrimesic acid-N,N,N-tris-(3-aza-1-methyl-4-oxopentane-1,5-diyl-{1-[1,4,7,10-tetrazacyclododecanyl]})-amide 23 g (8.85 mmol) of 1,3,5-triiodotrimesic acid-N,N,N-tris-(3-aza-4-oxopentane-1,5-diyl-{10-[1,4,7-tris-(benzyloxycarbonyl)-1,4,7,10-tetrazacyclododecanyl]})-amide is mixed carefully at 0–5° C. with 140 ml of HBr/AcOH (33%) and stirred for 3 hours at room temperature. Then, the reaction mixture is poured into 800 ml of diethyl ether, the solid that accumulates in this case is suctioned off and rewashed several times with diethyl ether. The residue is dissolved in 100 ml of water and 100 ml of dichloromethane while being stirred vigorously, and 32% NaOH solution is added until a pH of 10 is reached. The organic phase is separated, the aqueous phase is extracted three times with 50 ml each of dichloromethane, the combined organic phases are dried on magnesium sulfate and evaporated to the dry state.

Yield: 11.7 g (95% of theory) of a colorless solid Elementary analysis: Cld.: C, 41.39; H, 6.29; N, 18.10; I, 27.33. Fnd.: C, 41.51; H, 6.32; N, 18.01; I, 27.26.

e) 2,4,6-Triiodotrimesic acid-N N,N-tris-(3-aza-1-methyl-4-oxopentane-1,5-diyl-{10-[1,4,7-tris-(carboxymethyl)-1,4,7,10-tetrazacyclododecanyl]})-amide 18.8 g (13.5 mmol) of 1,3,5-triiodotrimesic acid-N,N,N-tris-(3-aza-1-methyl-4-oxopentane-1,5-diyl-{1-[1,4,7,10-tetraazacyclododecanyl]})-amide is dissolved-in 75 ml of water, 19.5 g (206.5 mmol) of chloroacetic acid is added, and a pH of 9.5 is set at 60° C. with 32% NaOH. It is heated for 10 hours to 70° C., whereby the pH of the reaction mixture is continuously readjusted to 9.5. After cooling to room temperature, a pH of 1 is set with concentrated HCl, and the solution is concentrated by evaporation in a vacuum. The residue is absorptively precipitated with 250 ml of methanol, insoluble components are filtered out, and the filtrate is concentrated by evaporation. The residue is dissolved in 100 ml of water and added to an ion-exchange column (600 ml, IR 120, H$^+$-form). Then, it is washed with 2 l of water, and the acidic eluate is concentrated by evaporation. The residue is dissolved in 70 ml of methanol and added in drops in 900 ml of diethyl ether, the solid that accumulates in this case is suctioned off, rewashed several times with diethyl ether and dried in a vacuum.

Yield: 15.0 g (58% of theory) of a colorless solid Elementary analysis: Cld.: C, 41.39; H, 5.53; N, 13.16; I, 19.88. Fnd.: C, 41.46; H, 5.537; N, 13.11; I, 19.79.

f) 2,4,6-Triiodotrimesic acid-N,N,N-tris-(3-aza-1-methyl-4-oxopentane-1,5-diyl-{10-[1,4,7-tris-(carboxylatomethyl)-1,4,7,10-tetrazacyclododecanyl, Gd complex]})amide 13.2 g (6.9 mmol) of 2,4,6-triiodotrimesic acid-N,N,N-tris-(3-aza-1-methyl-4-oxopentane-1,5-diyl-{10-[1,4,7-tris-(carboxymethyl)-1,4,7,10-tetrazacyclododecanyl]})-amide is dissolved in 100 ml of water and acidified by adding 3 ml of acetic acid. 3.7 g (10.4 mmol) of gadolinium oxide is added, and it is refluxed for 6 hours. After complexing is completed, the pH is set at 7.4 with ammonia and chromatographed on silica gel (mobile solvent: dichloromethane/methanol/ammonia: 10/10/1). The fractions that contain the product are combined and absorptively precipitated with 10 g of ion exchanger (IR 267 H-form) for 2 hours and filtered off, then it is absorptively precipitated with 10 g of ion exchanger (IRA 67 OH-form) for 2 hours, filtered off, mixed with 2 g of activated carbon, heated for 2 hours to 60° C., filtered off and freeze-dried.

Yield: 7.1 g (41% of theory) of a colorless solid Water content (Karl-Fischer): 5.6% Elementary analysis (relative to the anhydrous substance): Cld.: C, 33.34; H, 4.07; N, 10.60; I, 16.01; Gd, 19.84. Fnd.: C, 33.51; H, 4.14; N, 10.53; I, 15.98; Gd, 19.76.

EXAMPLE 5 a) Dibenzyloxiranylmethylamine 98.6 g (0.5 mol) of dibenzylamine and 55.5 g (0.6 mol) of epichlorohydrin are dissolved in 500 ml of methanol and heated for 6 hours to 80° C. The solution is evaporated to the dry state and mixed with 500 ml of tert-butanol. A solution of 36.4 g (0.65 mol) of potassium hydroxide in 50 ml of water is now added while being stirred, and it is heated for 2 hours to 80° C. After cooling to room temperature, the potassium chloride that is formed is filtered out, the filtrate is evaporated to the dry state and chromatographed on silica gel (mobile solvent: hexane/ethyl acetate 10:1). The fractions that contain the product are combined and concentrated by evaporation.

Yield: 126 g (99% of theory) of a colorless oil Elementary analysis: Cld.: C, 80.60; H, 7.56; N, 5.53. Fnd.: C, 80.72; H, 7.59; N, 5.51.

b) [1-(3-Dibenzylamino-2-hydroxypropyl)-1,4,7,10-tetraazacyclododecane]pentahydrochloride 100 ml (752.77 mmol) of N,N-dimethylformamide dimethyl acetal is added to 100 g (580.48 mmol) of 1,4,7,10-tetraazacyclododecane, dissolved in 700 ml of toluene, and it is heated for 2 hours to 120° C. under nitrogen. In this case, a methanol/toluene azeotrope is distilled off continuously. Then, the reaction mixture is concentrated by evaporation at 70° C. in a vacuum, 157 g (620 mmol) of dibenzyloxiranylmethylamine is added, and it is heated under nitrogen for 24 hours to 110° C. After cooling to room temperature, it is mixed with 500 ml of water and extracted twice with 200 ml each of ethyl acetate. The aqueous phase is mixed with 250 ml of concentrated HCl and then heated for 12 hours to 80° C. It is evaporated to the dry state, mixed with 200 ml of ethanol and 200 ml of methanol and evaporated again to the dry state. The residue is dissolved in 600 ml of ethanol while being heated, and then it is slowly cooled to 0° C., whereby a white solid is crystallized out. The solid is filtered off, washed with ethanol and then dried at 50° C. in a vacuum.

Yield: 280 g (79% of theory) of a colorless solid Elementary analysis: Cld.: C, 49.39; H, 7.29; N, 11.52; Cl, 29.16. Fnd.: C, 49.67; H, 7.44; N, 11.56; Cl, 28.22.

c) 10-(3-Dibenzylamino-2-hydroxypropyl)-1,4,7-tris-(tert-butoxycarbonylmethyl)-1,4,7,10-tetraazacyclododecane 32% NaOH solution is added to 250 g (411.2 mmol) of [1-(3-dibenzylamino-2-hydroxypropyl)-1,4,7,10-tetraazacyclododecane] pentahydrochloride, dissolved in 500 ml of water and 500 ml of dichloromethane, while being stirred vigorously until a pH of 10 is reached. The organic phase is separated, the aqueous phase is extracted three times with 250 ml each of dichloromethane, the combined organic phases are dried on magnesium sulfate and evaporated to the dry state. The residue is dissolved in 1200 ml of acetonitrile and mixed with 176.2 g (1.275 mol) of potassium carbonate. Then, 248.7 g (1.275 mol) of bromoacetic acid-tert-butyl ester is added while being stirred vigorously, and it is heated for 3 hours to 60° C. Insoluble components are filtered out, it is evaporated to the dry state and chromatographed on silica gel (mobile solvent:dichloromethane/methanol 20:1). The fractions that contain the product are combined and concentrated by evaporation.

Yield: 262 g (83% of theory) of a colorless solid Elementary analysis: Cld.: C, 67.25; H, 9.05; N, 9.12. Fnd.: C, 67.33; H, 9.02; N, 9.15.

d) 10-(3-Amino-2-hydroxypropyl)-1,4,7-tris-(tert-butoxycarbonylmethyl)-1,4,7,10-tetraazacyclododecane 76.8 g (100 mmol) of 10-(3-dibenzylamino-2-hydroxypropyl)-1,4,7-tris-(tert-butoxycarbonylmethyl)-1,4,7,10-tetraazacyclododecane is dissolved in 500 ml of methanol, mixed with 40 ml of water, and 10 g of palladium catalyst (20% Pd/C) is added. It is hydrogenated for 8 hours at 50°

C. under normal pressure. Catalyst is filtered out, and the filtrate is evaporated to the dry state in a vacuum.

Yield: 58.5 g (quantitative) of a colorless powder Elementary analysis: Cld.: C, 59.26; H, 9.77; N, 11.91. Fnd.: C, 59.48; H, 9.86; N, 11.67.

e) 1,3,5-Triiodotrimesic acid-N,N,N-tris-(2-hydroxypropane-1,3-diyl-{10-[1,4,7-tris-(tert-butoxycarbonylmethyl)-1,4,7,10-tetraazacyclododecanyl]})amide 12.2 g (120 mmol) of triethylamine and then 38.8 g (66 mmol) of 10-(3-amino-2-hydroxypropyl)-1,4,7-tris-(tert-butoxycarbonylmethyl)-1,4,7,10-tetraazacyclododecane are added to 12.86 g (20 mmol) of 1,3,5-triiodotrimesic acid tris chloride (DE 3001292, Schering AG, priority: Jan. 11, 1980), dissolved in 400 ml of tetrahydrofuran, and it is stirred for 6 hours at room temperature. Insoluble components are filtered out, it is evaporated to the dry state, and chromatographed on silica gel (mobile solvent:dichloromethane/methanol 20: 1). The fractions that contain the product are combined and concentrated by evaporation.

Yield: 32.7 g (71% of theory) of a colorless solid Elementary analysis: Cld.: C, 50.19; H, 7.37; N, 9.15; I, 16.57. Fnd.: C, 50.33; H, 7.40; N, 9.11; I, 16.43.

f) 1,3,5-Triiodotrimesic acid-N N,N-tris-(2-hydroxypropane-1,3-diyl-{10-[1,4,7-tris-(carboxymethyl)-1,4,7,10-tetraazacyclododecanyl]})amide 34.5 g (15 mmol) of 1,3,5-triiodotrimesic acid-N,N,N-tris-(2-hydroxypropane-1,3-diyl-{10-[1,4,7-tris-(tert-butoxycarbonylmethyl)-1,4,7,10-tetraazacyclododecanyl]}) amide is dissolved in 100 ml of dichloromethane, mixed at 0° C. with 100 ml of trifluoroacetic acid and stirred for 3 hours at 0° C. The batch is poured into 500 ml of diethyl ether, the solid that accumulates is filtered off, rewashed three times with 100 ml each of diethyl ether and dried in a vacuum.

Yield: 25.3 g (94% of theory) of a colorless solid Elementary analysis: Cld.: C, 40.21; H, 5.40; N, 11.72; I, 21.24. Fnd.: C, 40.44; H, 5.49; N, 11.67; I, 21.11.

g) 1,3.5-Triiodotrimesic acid-N,N,N-tris-(2-hydroxypropane-1,3-diyl-{10-[1,4,7-tris-(carboxylatomethyl)-1,4,7,10-tetraazacyclododecanyl]}, Gd complex)amide 21.5 g (12 mmol) of 1,3,5-triiodotrimesic acid-N,N,N-tris-(2-hydroxypropane-1,3-diyl-{10-[1,4,7-tris-(carboxymethyl)-1,4,7,10-tetraazacyclododecanyl]})amide is dissolved in 250 ml of water and acidified by adding 5 ml of acetic acid. 13 g (36.2 mmol) of gadolinium oxide is added and refluxed for 3 hours. After complexing is completed, the pH is set at 7.4 with ammonia and chromatographed on silica gel (mobile solvent:dichloromethane/methanol/ammonia: 20/20/1). The fractions that contain the product are combined and absorptively precipitated with 10 g of ion exchanger (IR 267 H-form) for 2 hours and filtered off, then absorptively precipitated with 10 g of ion exchanger (IRA 67 OH-form) for 2 hours, filtered off, mixed with 2 g of activated carbon, heated for 2 hours to 60° C., filtered off and freeze-dried.

Yield: 19.4 g (68% of theory) of a colorless solid Water content (Karl-Fischer): 5.3% Elementary analysis (relative to anhydrous substance): Cld.: C, 31.96; H, 3.89; N, 9.32; I, 16.88; Gd, 20.92. Fnd.: C, 32.11; H, 3.94; N, 9.28; I, 16.77; Gd, 20.79.

EXAMPLE 6 a) 1-Benzyl-1-methyl(oxiranylmethyl)amine 60.6 g (0.5 mol) of benzylmethylamine and 55.5 g (0.6 mol) of epichlorohydrin are dissolved in 500 ml of methanol and heated for 6 hours to 80° C. The solution is evaporated to the dry state and mixed with 500 ml of tert-butanol. A solution of 36.4 g (0.65 mol) of potassium hydroxide in 50 ml of water is now added while being stirred, and it is heated for 2 hours to 80° C. After cooling to room temperature, potassium chloride that has formed is filtered out, the filtrate is evaporated to the dry state and chromatographed on silica gel (mobile solvent:hexane/ethyl acetate 10:1). The fractions that contain the product are combined and concentrated by evaporation.

Yield: 85 g (96% of theory) of a colorless oil Elementary analysis: Cld.: C, 74;54; H, 8.53; N, 7.90. Fnd.: C, 74.68; H, 8.55; N, 7.82.

b) [1-(3-Benzylmethylamino-2-hydroxypropyl)-1,4,7,10-tetraazacyclododecane]pentahydrochloride 100 ml (752.77 mmol) of N,N-dimethylformamide dimethyl acetal is added to 100 g (580.48 mmol) of 1,4,7,10-tetraazacyclododecane, dissolved in 700 ml of toluene, and it is heated for 2 hours to 120° C. under nitrogen. In this case, a methanol/toluene azeotrope is continuously distilled off. Then, the reaction mixture is concentrated by evaporation at 70° C. in a vacuum, 110 g (620 mmol) of 1-benzyl-1-methyl(oxiranylmethyl)amine is added, and it is heated under nitrogen for 24 hours to 110° C. After cooling to room temperature, it is mixed with 500 ml of water and extracted twice with 200 ml each of ethyl acetate. The aqueous phase is mixed with 250 ml of concentrated HCl and then heated for 12 hours to 80° C. It is evaporated to the dry state, mixed with 200 ml of ethanol and 200 ml of methanol and again evaporated to the dry state. The residue is dissolved in 600 ml of ethanol while being heated, and they) it is slowly cooled to 0° C., whereby a white solid crystallizes out. The solid is filtered off, washed with ethanol and then dried at 50° C. in a vacuum.

Yield: 235 g (76% of theory) of a colorless solid Elementary analysis: Cld.: C, 42.91; H, 7.58; N, 13.17; Cl, 33.33. Fnd.: C, 43.34; H, 7.60; N, 13.29; Cl, 32.78.

c) 10-(3-Benzylmethylamino-2-hydroxypropyl)-1,4,7-tris-(tert-butoxycarbonylmethyl)-1,4,7,10-tetraazacyclododecane 32% NaOH solution is added to 212.7 g (400 mmol) of [1-(3-benzylmethylamino-2-hydroxypropyl)-1,4,7,10-tetraazacyclododecane]pentahydrochloride, dissolved in 500 ml of water and 500 ml of dichloromethane, while being stirred vigorously until a pH of 10 is reached. The organic phase is separated, the aqueous phase is extracted three times with 250 ml each of dichloromethane, the combined organic phases are dried on magnesium sulfate and evaporated to the dry state. The residue is dissolved in 1200 ml of acetonitrile and mixed with 176.2 g (1.275 mol) of potassium carbonate. Then, 248.7 g (1.275 mol) of bromoacetic acid-tert-butyl ester is added while being stirred vigorously, and it is heated for 3 hours to 60° C. Insoluble components are filtered out, it is evaporated to the dry state, and chromatographed on silica gel (mobile solvent:dichloromethane/methanol 20:1). The fractions that contain the product are combined and concentrated by evaporation.

d) 10-(3-Methylamino-2-hydroxypropyl)-1,4,7-tris-(tert-butoxycarbonylmethyl)-1,4,7,10-tetraazacyclododecane 69.2 g (100 mmol) of 10-(3-benzylmethylamino-2-hydroxypropyl)-1,4,7-tris-(tert-butoxycarbonylmethyl)-1,4,7,10-tetraazacyclododecane is dissolved in 500 ml of methanol, mixed with 40 ml of water, and 10 g of palladium catalyst (20% Pd/C) is added. It is hydrogenated for 8 hours at 50° C. under normal pressure. Catalyst is filtered out, and the filtrate is evaporated to the dry state in a vacuum.

Yield: 60 g (quantitative) of a colorless powder Elementary analysis: Cld.: C, 59.67; H, 9.88; N, 11.64. Fnd.: C, 59.89; H, 9.81; N, 11.52.

e) 1,3,5-Triiodotrimesic acid-N,N,N-tris-(2-hydroxypropane-1,3-diyl-{10-[1,4,7-tris-(tert-butoxycarbonylmethyl)-1,4,7,10-tetraazacyclododecanyl]})methylamide 12.2 g (120 mmol) of triethylamine and then 39.7 g (66 mmol) of 10-(3-methylamino-2-hydroxypropyl)-1,4,7-tris-(tert-butoxycarbonylmethyl)-1,4,7,10-tetraazacyclododecane are added to 12.86 g (20 mmol) of 1,3,5-triiodotrimesic acid tris chloride (DE 3001292, Schering AG, priority: Jan. 11, 1980), dissolved in 400 ml of tetrahydrofuran, and it is stirred for 18 hours at room temperature. Insoluble components are filtered out, it is evaporated to the dry state and chromatographed on silica gel (mobile solvent:dichloromethane/methanol 20:1). The fractions that contain the product are combined and concentrated by evaporation.

Yield: 31.4 g (67% of theory) of a colorless solid Elementary analysis: Cld.: C, 50.83; H, 7.50; N, 8.98; I, 16.41. Fnd.: C, 50.99; H, 7.57; N, 8.90; I, 16.22.

f) 1,3,5-Triiodotrimesic acid-N,N,N-tris-(2-hydroxypropane-1,3-diyl-{10-[1,4,7-tris-(carboxymethyl)-1,4,7,10-tetraazacyclododecanyl]})methylamide 35.1 g (15 mmol) of 1,3,5-triiodotrimesic acid-N,N,N-tris-(2-hydroxypropane-1,3-diyl-{10-[1,4,7-tris-(tert-butoxycarbonylmethyl)-1,4,7,10-tetraazacyclododecanyl]})methylamide is dissolved in 100 ml of dichloromethane, mixed at 0° C. with 100 ml of trifluoroacetic acid and stirred for 3 hours at 0° C. The batch is poured into 500 ml of diethyl ether, the solid that accumulates is filtered off, it is rewashed three times with 100 ml each of diethyl ether and dried in a vacuum.

Yield: 26.4 g (96% of theory) of a colorless solid Elementary analysis: Cld.: C, 40.25; H, 5.60; N, 11.45; I, 20.75. Fnd.: C, 40.17; H, 5.69; N, 11.51; I, 20.58.

g) 1,3,5-Triiodotrimesic acid-N,N,N-tris-(2-hydroxypropane-1,3-diyl-{10-[1,4,7-tris-(carboxylatomethyl)-1,4,7,10-tetraazacyclododecanyl]}, Gd complex) methylamide 22 g (12 mmol) of 1,3,5-triiodotrimesic acid-N,N,N-tris-(2-hydroxypropane-1,3-diyl-{10-[1,4,7-tris-(carboxymethyl)-1,4,7,10-tetraazacyclododecanyl]})methylamide is dissolved in 250 ml of water and acidified by adding 5 ml of acetic acid. 13 g (36.2 mmol) of gadolinium oxide is added, and it is refluxed for 3 hours. After complexing is completed, the pH is set at 7.4 with ammonia and chromatographed on silica gel (mobile solvent:dichloromethane/methanol/ammonia: 20/20/1). The fractions that contain the product are combined and absorptively precipitated with 10 g of ion exchanger (IR 267 H-form) for 2 hours and filtered off, then absorptively precipitated with 10 g of ion exchanger (IRA 67 OH-form) for 2 hours, filtered off, mixed with 2 g of activated carbon, heated for 2 hours to 60° C., filtered off and freeze-dried.

Yield: 18.2 g (62% of theory) of a colorless solid Water content (Karl-Fischer): 6.1% Elementary analysis (relative to the anhydrous substance): Cld.: C, 32.94; H, 4.08; N, 9.15; I, 16.57; Gd, 20.54. Fnd.: C, 33.21; H, 4.13; N, 9.10; I, 16.43; Gd, 20.22.

EXAMPLE 7 a) 1,3,5-Triiodo-2,4,6-tris-(oxiranylmethoxymethyl)benzene 55 ml of a 32% NaOH solution is added in drops at room temperature to a mixture that consists of 11.0 g (20.1 mmol) of 1,3,5-triiodo-2,4,6-trishydroxymethylbenzene, 55.5 g (0.6 mol) of epichlorohydrin and 1.1 g (3.2 mmol) of tetrabutylammonium hydrogen sulfate within 1 hour, and then it is stirred for 12 hours. It is mixed with 150 ml of water and extracted twice with 200 ml each of toluene. The combined organic phases are dried on sodium sulfate, the solvent is evaporated to the dry state and chromatographed on silica gel (mobile solvent:hexane/ethyl acetate 10:1). The fractions that contain the product are combined and concentrated by evaporation.

Yield: 10.5 g (73% of theory) of a colorless solid Elementary analysis: Cld.: C, 30.28; H, 2.96; I, 53.32. Fnd.: C, 30.44; H, 2.99; I, 53.21.

b) 1,3,5-Triiodo-{2,4,6-tris[2-hydroxy-3-(1,4,7,10-tetraazacyclododecan-1-yl)propyloxy-methyl]}benzene 10 ml (75.28 mmol) of N,N-dimethylformamide dimethyl acetal is added to 10 g (58.05 mmol) of 1,4,7,10-tetraazacyclododecane, dissolved in 100 ml of toluene, and it is heated for 2 hours to 120° C. under nitrogen. In this case, a methanol/toluene azeotrope is distilled off continuously. Then, the reaction mixture is concentrated by evaporation at 70° C. in a vacuum, 13.6 g (19.1 mmol) of 1,3,5-triiodo-2,4,6-tris-(oxiranylmethoxymethyl)benzene is added, and it is heated under nitrogen for 24 hours to 110° C. After cooling to room temperature, it is mixed with 100 ml of 2N HCl and then heated for 12 hours to 80° C. It is evaporated to the dry state, mixed with 50 ml of ethanol and 50 ml of methanol and evaporated to the dry state again. The residue is dissolved in 100 ml of ethanol while being heated, and then slowly cooled to 0° C., whereby a white solid crystallizes out. The solid is filtered off, washed with ethanol and then dried at 50° C. in a vacuum. The solid is dissolved in 100 ml of water and 100 ml of dichloromethane, and 32% NaOH solution is added while being stirred vigorously until a pH of 10 is reached. The organic phase is separated, the aqueous phase is extracted three times with 100 ml each of dichloromethane, the combined organic phases are dried on magnesium sulfate and evaporated to the dry state.

Yield: 19.0 g (81% of theory) of a colorless solid Elementary analysis: Cld.: C, 40.98; H, 6.63; N, 13.66; I, 30.93. Fnd.: C, 41.32; H, 6.71; N, 13.54; I, 30.77.

c) 1,3,5-Triiodo-{2,4,6-tris[2-hydroxy-3-(1,4,7-triscarboxymethyl-1,4,7,10-tetraazacyclododecan-1-yl)propyloxymethyl]}benzene 16.6 g (13.5 mmol) of 1,3,5-triiodo-{2,4,6-tris[2-hydroxy-3-(1,4,7,10-tetraazacyclododecan-1-yl)propyloxymethyl]}benzene is dissolved in 75 ml of water, 19.5 g (206.5 mmol) of chloroacetic acid is added, and a pH of 9.5 is set at 60° C. with 32% NaOH. It is heated for 10 hours to 70° C., whereby the pH of the reaction mixture is continuously readjusted to 9.5. After cooling to room temperature, a pH of 1 is set with concentrated HCl, and the solution is concentrated by evaporation in a vacuum. The residue is absorptively precipitated with 250 ml of methanol, insoluble components are filtered out, and the filtrate is concentrated by evaporation. The residue is dissolved in 100 ml of water and added to an ion-exchange column (600 ml, IR 120, H+-form). Then, it is washed with 2 l of water, and the acidic eluate is concentrated by evaporation. The residue is dissolved in 70 ml of methanol and added in drops in 900 ml of diethyl ether, the solid that accumulates in this case is suctioned off, rewashed several times with diethyl ether and dried in a vacuum.

Yield: 14.4 g (61% of theory) of a colorless solid Elementary analysis: Cld.: C, 41.11; H, 5.69; N, 9.59; I, 21.71. Fnd.: C, 41.34; H, 5.56; N, 9.62; I, 21.45.

d) 1,3,5-Triiodo-{2,4,6-tris[2-hydroxy-3-(1,4,7-triscarboxylatomethyl-1,4,7,10-tetraazacyclododecan-1-yl)propyloxymethyl]Gd complex}benzene 12.1 g (6.9 mmol) of 1,3,5-triiodo-{2,4,6-tris[2-hydroxy-3-(1,4,7-triscarboxymethyl-1,4,7,10-tetraazacyclododecan-1-yl)propyloxymethyl]}benzene is dissolved in 100 ml of water and acidified by adding 3 ml of acetic acid. 3.7 g (10.4 mmol) of gadolinium oxide is added, and it is refluxed for 6 hours. After complexing is completed, the pH is set at 7.4 with ammonia, and it is chromatographed on silica gel (mobile solvent:dichloromethane/methanol/ammonia: 10/10/1). The fractions that contain the product are combined and absorptively precipitated with 10 g of ion exchanger (IR 267 H-form) for 2 hours and filtered off, then absorptively precipitated with 10 g of ion exchanger (IRA 67 OH-form) for 2 hours, filtered off, mixed with 2 g of activated carbon, heated for 2 hours to 60° C., filtered off and freeze-dried.

Yield: 7.0 g (43% of theory) of a colorless solid Water content (Karl-Fischer): 5.4% Elementary analysis (relative to the anhydrous substance): Cld.: C, 32.52; H, 4.09; N, 7.59; I, 17.18; Gd, 21.29. Fnd.: C, 32.88; H, 4.19; N, 7.62; I, 17.00; Gd, 20.99.

EXAMPLE 8 a) 10-[4-Aza-6-(benzyloxycarbonylamino)-5-oxo-2-hydroxyhexyl]-1,4,7-tris-(tert-butoxycarbonylmethyl)-1,4,7,10-tetraazacyclododecane 21.97 g (105 mmol) of Z-glycine is dissolved in 400 ml of DMF, mixed with 12.1 g (105 mmol) of N-hydroxysuccinimide and 21.7 g (105 mmol) of dicyclohexylcarbodiimide while being cooled with ice and preactivated for 1 hour in ice. Then, 58.8 g (100 mmol) of 10-(3-amino-2-hydroxypropyl)-1,4,7-tris-(tert-butoxycarbonylmethyl)-1,4,7,10-tetraazacyclododecane and 15.4 ml (120 mmol) of triethylamine are added and stirred overnight at room temperature. Insoluble components are filtered out and evaporated to the dry state. The residue is taken up in 500 ml of ethyl acetate and extracted twice with 500 ml each of water. The organic phase is dried on sodium sulfate, the solvent is evaporated to the dry state, and the residue is chromatographed on silica gel (mobile solvent:dichloromethane/methanol 20:1). The fractions that contain the product are combined and concentrated by evaporation.

Yield: 63.2 g (81% of theory) of a colorless solid Elementary analysis: Cld.: C, 60.13; H, 8.54; N, 10.79. Fnd.: C, 60.32; H, 8.561; N, 10.59.

b) 10-(4-Aza-6-amino-5-oxo-2-hydroxyhexyl)-1,4,7-tris-(tert-butoxycarbonylmethyl)-1,4,7,10-tetraazacyclododecane 60 g (77 mmol) of 10-[4-aza-6-(benzyloxycarbonylamino)-5-oxo-2-hydroxyhexyl]-1,4,7-tris-(tert-butoxycarbonylmethyl)-1,4,7,10-tetraazacyclododecane is dissolved in 500 ml of methanol, mixed with 40 ml of water, and 10 g of palladium catalyst (10% Pd/C) is added. It is hydrogenated for 8 hours at 50° C. under normal pressure. Catalyst is filtered out, and the filtrate is evaporated to the dry state.

Yield: 48.8 g (98% of theory) of a colorless solid Elementary analysis: Cld.: C, 57.74; H, 9.38; N, 13.03. Fnd.: C, 57.68; H, 9.44; N, 13.11.

c) 1,3,5-Triiodotrimesic acid-N,N,N-tris-(3-aza-2-oxo-5-hydroxyhexane-1,6-diyl-{10-[1,4,7-tris-(tert-butoxycarbonylmethyl)-1,4,7,10-tetraazacyclododecanyl]})-amide 12.2 g (120 mmol) of triethylamine and then 42.6 g (66 mmol) of 10-(4-aza-6-amino-5-oxo-2-hydroxyhexyl)-1,4,7-tris-(tert-butoxycarbonylmethyl)-1,4,7,10-tetraazacyclododecane are added to 12.86 g (20 mmol) of 1,3,5-triiodotrimesic acid tris chloride (DE 3001292, Schering AG, priority: Jan. 11, 1980), dissolved in 400 ml of tetrahydrofuran, and it is stirred for 6 hours at room temperature. Insoluble components are filtered out, evaporated to the dry state and chromatographed on silica gel (mobile solvent: dichloromethane/methanol 20:1). The fractions that contain the product are combined and concentrated by evaporation.

Yield: 36.5 g (74% of theory) of a colorless solid Elementary analysis: Cld.: C, 49.63; H, 7.23; N, 10.21; I, 15.42. Fnd.: C, 49.97; H, 7.31; N, 10.12; I, 15.26.

d) 1,3,5-Triiodotrimesic acid-N,N,N-tris-(3-aza-2-oxo-5-hydroxyhexane-1,6-diyl-{10-[1,4,7-tris-(carboxymethyl)-1,4,7,10-tetraazacyclododecanyl]}) amide 34.6 g (14 mmol) of 1,3,5-triiodotrimesic acid-N,N,N-tris-(3-aza-2-oxo-5-hydroxyhexane-1,6-diyl-{10-[1,4,7-tris-(tert-butoxycarbonylmethyl)-1,4,7,10-tetraazacyclododecanyl]})amide is dissolved in 100 ml of dichloromethane, mixed at 0° C. with 100 ml of trifluoroacetic acid and stirred for 3 hours at 0° C. The batch is poured into 500 ml of diethyl ether, the solid that accumulates is filtered off, rewashed three times with 100 ml each of diethyl ether and dried in a vacuum.

Yield: 26.0 g (95% of theory) of a colorless solid Elementary analysis: Cld.: C, 40.38; H, 5.39; N, 12.84; I, 19.39. Fnd.: C, 40.56; H, 5.45; N, 12.78; I, 19.17.

e) 1,3,5-Triiodotrimesic acid-N,N,N-tris-(3-aza-2-oxo-5-hydroxyhexane-1,6-diyl-{10-[1,4,7-tris-(carboxylatomethyl)-1,4,7,10-tetraazacyclododecanyl]}, Gd complex)amide 23.6 g (12 mmol) of 1,3,5-triodotrimesic acid-N,N,N-tris-(3-aza-2-oxo-5-hydroxyhexane-1,6-diyl-{10-[1,4,7-tris-(carboxymethyl)-1,4,7,10-tetraazacyclo-dodecanyl]})amide is dissolved in 250 ml of water and acidified by adding 5 ml of acetic acid. 13 g (36.2 mmol) of gadolinium oxide is added, and it is refluxed for 3 hours. After complexing is completed, the pH is set at 7.4 again with ammonia, and it is chromatographed on silica gel (mobile solvent:dichloromethane/methanol/ammonia: 20/20/1). The fractions that contain the product are combined and absorptively precipitated with 10 g of ion exchanger (IR 267 H-form) for 2 hours and filtered off, then absorptively precipitated with 10 g of ion exchanger (IRA 67 OH-form) for 2 hours, filtered off, mixed with 2 g of activated carbon, heated for 2 hours to 60° C., filtered off and freeze-dried.

Yield: 20.8 g (67% of theory) of a colorless solid Water content (Karl-Fischer): 6.4% Elementary analysis (relative to the anhydrous substance): Cld.: C, 32.68; H, 3.99; N, 10.39; I, 15.69; Gd, 19.45. Fnd.: C, 32.99; H, 4.07; N, 10.35; I, 15.53; Gd, 19.22.

EXAMPLE 9 a) 1,3,5-Triiodo-2,4,6-tris-(toluenesulfonyloxy)methylbenzene 76.3 g (400 mmol) of toluenesulfonic acid chloride is added in drops to a mixture that consists of 50.0 g (91.4 mmol) of 1,3,5-triiodo-2,4,6-tris-hydroxymethylbenzene and 3 g (8.7 mmol) of tetrabutylammonium hydrogen sulfate in 200 ml of 32% NaOH solution and 300 ml of toluene at room temperature, and then it is stirred for 12 hours. It is mixed with 300 ml of water and extracted twice with 200 ml each of toluene. The combined organic phases are dried on sodium sulfate, the solvent is evaporated to the dry state and chromatographed on silica gel (mobile solvent:hexane/ethyl acetate 10:1). The fractions that contain the product are combined and concentrated by evaporation.

Yield: 47.2 g (51% of theory) of a colorless solid Elementary analysis: Cld.: C, 35.73; H, 2.70; I, 37.75. Fnd.: C, 36.03; H, 2.77; I, 37.56.

b) 1,4,7-Tris-(benzyloxycarbonyl)-10-(carbamidomethyl)-1,4,7,10-tetrazacyclododecane 17.8 g (130.5 mmol) of isobutyl chloroformate is added in drops at −20° C. to a solution of 75 g (118.7 mmol) of 1,4,7-tris-(benzyloxycarbonyl)-10-(carboxymethyl)-1,4,7,10-tetrazacyclododecane and 16.9 g (130.5 mmol) of diusopropylethylamine in 500 ml of THF. Then, it is stirred for 1 hour at −20° C. and mixed carefully with 20 ml of 25% aqueous ammonia solution. It is stirred for 2 more hours at 0° C., then the solvent is distilled off in a vacuum and the residue is chromatographed on silica gel (mobile solvent: ethyl acetate/hexane 10:1). The fractions that contain the product are combined and concentrated by evaporation.

Yield: 60.7 g (81% of theory) of a colorless solid Elementary analysis: Cld.: C, 64.64; H, 6.54; N, 11.09. Fnd.: C, 64.81; H, 6.549; N, 11.00.

c) 1,3,5-Triiodo-2,4,6-tris-(2-aza-3-oxobutane-1,4-diyl-{10-[1,4,7-tris-(benzyloxycarbonyl)-1,4,7,10-tetraazacyclododecanyl]})benzene 44.6 g (70.6 mmol) of 1,4,7-tris-(benzyloxycarbonyl)-10-(carbamidomethyl)-1,4,7,10-tetrazacyclododecane is dissolved in 500 ml of THF and mixed at 0° C. under argon with 1.71 g (71 mmol) of sodium hydride and stirred for 1 hour at room temperature. Then, a solution of 20.2 g (20 mmol) of 1,3,5-triiodo-2,4,6-tris-(toluenesulfonyloxy)methylbenzene in 150 ml of THF is added in drops and refluxed for 20 hours. After cooling, insoluble components are filtered out and evaporated to the dry state. The residue is taken up in 500 ml of ethyl acetate and extracted twice with 500 ml. each of water. The organic phase is dried on sodium sulfate, the solvent is evaporated to the dry state, and the residue is chromatographed on silica gel (mobile solvent: dichloromethane/methanol 20: 1). The fractions that contain the product are combined and concentrated by evaporation.

Yield: 29.4 g (62% of theory) of a colorless solid Elementary analysis: Cld.: C, 55.85; H, 5.32; N, 8.80; I, 15.95. Fnd.: C, 56.07; H, 5.39; N, 8.67; I, 15.76.

d) 1,3,5-Triiodo-2,4,6-tris-{2-aza-3-oxobutane-1,4-diyl-[10-(1,4,7,10-tetraazacyclododecanyl)]}benzene 20 g (8.4 mmol) of 1,3,5-triiodo-2,4,6-tris-(2-aza-3-oxobutane-1,4-diyl-{10-[1,4,7-tris-(benzyloxycarbonyl)-1,4,7,10-tetraazacyclododecanyl]})benzene is carefully mixed at 0–5° C. [with] 140 ml of HBr/AcOH (33%) and stirred for 3 hours at room temperature. Then, the reaction mixture is poured into 800 ml of diethyl ether, the solid that accumulates in this case is suctioned off, and it is rewashed several times with diethyl ether. The residue is dissolved in 100 ml of water and 100 ml of dichloromethane while being stirred vigorously, and 32% NaOH solution is added until a pH of 10 is reached. The organic phase is separated, the aqueous phase is extracted three times with 50 ml each of dichloromethane, the combined organic phases are dried on magnesium sulfate and evaporated to the dry state.

Yield: 9.1 g (91% of theory) of a colorless solid Elementary analysis: Cld.: C, 39.70; H, 6.15; N, 17.81; I, 32.27. Fnd.: C, 39.91; H, 6.22; N, 17.75; I, 32.09.

e) 1,3,5-Triiodo-2,4,6-tris-(2-aza-3-oxobutane-1,4-diyl-{10-[1,4,7-tris-(carboxymethyl)-1,4,7,10-tetraazacyclododecanyl]})benzene 17.7 g (15 mmol) of 1,3,5-triiodo-2,4,6-tris-{2-aza-3-oxobutane-1,4-diyl-[10-(1,4,7,10-tetraazacyclododecanyl)]}benzene is dissolved in 75 ml of water, 19.5 g (206.5 mmol) of chloroacetic acid is added, and a pH of 9.5 is set at 60° C. with 32% NaOH. It is heated for 10 hours to 70° C., whereby the pH of the reaction mixture is readjusted continuously to 9.5. After cooling to room temperature, the pH is set at 1 with concentrated HCl, and the solution is concentrated by evaporation in a vacuum. The residue is absorptively precipitated with 250 ml of methanol, insoluble components are filtered out, and the filtrate is concentrated by evaporation. The residue is dissolved in 100 ml of water and added to an ion-exchange column (600 ml, IR 120, H+-form). Then, it is washed with 2 l of water, and the acidic eluate is concentrated by evaporation. The residue is dissolved in 70 ml of methanol and added in drops in 900 ml of diethyl ether, the solid that accumulates in this case is suctioned off, rewashed several times with diethyl ether and dried in a vacuum.

f) 1,3,5-Triiodo-2,4,6-tris-(2-aza-3-oxobutane-1,4-diyl-{10-[1,4,7-tris-(carboxylatomethyl)-1,4,7,10-tetraazacyclododecanyl]}, Gd complex)benzene 11.7 g (6.9 mmol) of 1,3,5-triiodo-2,4,6-tris-(2-aza-3-oxobutane-1,4-diyl-{10-[1,4,7-tris-(carboxymethyl)-1,4,7,10-tetraazacyclododecanyl]})benzene is dissolved in 100 ml of water and acidified by adding 3 ml of acetic acid. 3.7 g (10.4 mmol) of gadolinium oxide is added, and it is refluxed for 6 hours. After complexing is completed, the pH is set at 7.4 with ammonia, and it is chromatographed on silica gel (mobile solvent:dichloromethane/methanol/ammonia: 10/10/1). The fractions that contain the product are combined and absorptively precipitated with 10 g of ion exchanger (IR 267 H-form) for 2 hours and filtered off, then absorptively precipitated with 10 g of ion exchanger (IRA 67 OH-form) for 2 hours, filtered off, mixed with 2 g of activated carbon, heated for 2 hours to 60° C., filtered off and freeze-dried.

Yield: 8.4 g (53% of theory) of a colorless solid Water content (Karl-Fischer): 6.1% Elementary analysis (relative to the anhydrous substance): Cld.: C, 31.63; H, 3.77; N, 9.71; I, 17.59; Gd, 21.79. Fnd.: C, 31.77; H, 3.72; N, 9.76; I, 17.45 Gd, 21.63.

g) 1,3,5-Triiodo-2,4,6-tris-(2-aza-3-oxobutane-1,4-diyl-{10-[1,4,7-tris-(carboxylatomethyl)-1,4,7,10-tetraazacyclododecanyl]}, Dy complex)benzene 11.7 g (6.9 mmol) of 1,3,5-triiodo-{2,4,6-tris-[2-(4,7,10-triscarboxymethyl-1,4,7,10-tetraazacyclododecan-1-ylacetylamino)methyl]}benzene is dissolved in 100 ml of water and acidified by adding 3 ml of acetic acid. 3.88 g (10.4 mmol) of dysprosium oxide is added, and it is refluxed for 6 hours. After complexing is completed, the pH is set at 7.4 with ammonia, and it is chromatographed on silica gel (mobile solvent:dichloromethane/methanol/ammonia: 10/10/1). The fractions that contain the product are combined and absorptively precipitated with 10 g of ion exchanger (IR 267 H-form) for 2 hours and filtered off, then absorptively precipitated with 10 g of ion exchanger (IRA 67 OH-form) for 2 hours, filtered off, mixed with 2 g of activated carbon, heated for 2 hours to 60° C., filtered off and freeze-dried.

Yield: 7.5 g (47% of theory) of a colorless solid Water content (Karl-Fischer): 5.9% Elementary analysis (relative to the anhydrous substance): Cld.: C, 31.40; H, 3.74; N, 9.64; I, 17.46; Dy, 22.36. Fnd.: C, 31.65; H, 3.79; N, 9.67; I, 17.25; Dy, 22.11.

h) 1,3,5-Triiodo-2,4,6-tris-(2-aza-3-oxobutane-1,4-diyl-{10-[1,4,7-tris-(carboxylatomethyl)-1,4,7,10-tetraazacyclododecanyl]}, Y complex)benzene 11.7 g (6.9 mmol) of 1,3,5-triodo-{2,4,6-tris-[2-(4,7,10-triscarboxymethyl-1,4,7,10-tetraazacyclododecan-1-ylacetylamino)methyl]}benzene is dissolved-in 100 ml of water and acidified by adding 3 ml of acetic acid. 3.72 g (10.4 mmol) of yttrium carbonate is added, and it is refluxed for 6 hours. After complexing is completed, the pH is set at 7.4 with ammonia, and it is chromatographed on silica gel (mobile solvent:dichloromethane/methanol/ammonia: 10/10/1). The fractions that contain the product are combined and absorptively precipitated with 10 g of ion exchanger (IR 267 H-form) for 2 hours and filtered off, then absorptively precipitated with 10 g of ion exchanger (IRA 67 OH-form) for 2 hours, filtered off, mixed with 2 g of activated carbon, heated for 2 hours to 60° C., filtered off and freeze-dried.

Yield: 8.7 g (61% of theory) of a colorless solid Water content (Karl-Fischer): 5.4% Elementary analysis (relative to the anhydrous substance): Cld.: C, 34.93; H, 4.17; N, 10.72; I, 19.43; Y, 13.61. Fnd.: C, 35.12; H, 4.11; N, 10.79; I, 19.34; Y, 13.52.

EXAMPLE 10 a) 1,4,7-Tris-(benzyloxycarbonyl)-10-(1-carbamidoethyl)-1,4,7,10-tetrazacyclododecane 17.8 g (130.5 mmol) of isobutyl chloroformate is added in drops to a solution of 76.8 g (118.7 mmol) of 1,4,7-tris-(benzyloxycarbonyl)-10-(1-carboxyethyl)-1,4,7,10-tetrazacyclododecane and 16.9 g (130.5 mmol) of diisopropylethylamine in 500 ml of THF at −20° C. Then, it is stirred for 1 hour at −20° C. and carefully mixed with 20 ml of 25% aqueous ammonia solution. It is stirred for 2 more hours at 0° C., then the solvent is distilled off in a vacuum, and the residue is chromatographed on silica gel (mobile solvent: ethyl acetate/hexane 10:1). The fractions that contain the product are combined and concentrated by evaporation.

Yield: 59.8 g (78% of theory) of a colorless solid Elementary analysis: Cld.: C, 65.10; H, 6.71; N, 10.85. Fnd.: C, 65.34; H, 6.86; N, 10.67.

b) 1,3,5-Triiodo-2,4,6-tris-(2-aza-4-methyl-3-oxobutane-1,4-diyl-{10-[1,4,7-tris-(benzyloxycarbonyl)-1,4,7,10-tetraazacyclododecanyl]})benzene 45.6 g (70.6 mmol) of 1,4,7-tris-(benzyloxycarbonyl)-10-(1-carbamidoethyl)-1,4,7,10-tetrazacyclododecane is dissolved in 500 ml of THF and mixed at 0° C. under argon with 1.71 g (71 mmol) of sodium hydride and stirred for 1 hour at room temperature. Then, a solution of 20.2 g (20 mmol) of 1,3,5-triiodo-2,4,6-tris-(toluenesulfonyloxy)methylbenzene in 150 ml of THF is added in drops and stirred for 20 hours under reflux. After cooling, insoluble components are filtered out and evaporated to the dry state. The residue is taken up in 500 ml of ethyl acetate and extracted twice with 500 ml each of water. The organic phase is dried on sodium sulfate, the solvent is evaporated to the dry state, and the residue is chromatographed on silica gel (mobile solvent: dichloromethane/methanol 20: 1). The fractions that contain the product are combined and concentrated by evaporation.

Yield: 27.7 g (57% of theory) of a colorless solid Elementary analysis: Cld.: C, 56.37; H, 5.48; N, 8.65; I, 15.67. Fnd.: C, 56.56; H, 5.39; N, 8.73; I, 15.46.

c) 1,3,5-Triiodo-2,4,6-tris-{2-aza-4-methyl-3-oxobutane-1,4-diyl-[10-(1,4,7,10-tetraazacyclododecanyl)]}benzene 25 g (10.3 mmol) of 1,3,5-triiodo-2,4,6-tris-(2-aza-4-methyl-3-oxobutane-1,4-diyl-{10-[1,4,7-tris-(benzyloxycarbonyl)-1,4,7,10-tetraazacyclododecanyl]})benzene is carefully mixed at 0–5° C. with 150 ml of HBr/AcOH (33%) and stirred for 3 hours at room temperature. Then, the reaction mixture is poured into 800 ml of diethyl ether, the solid that accumulates in this case is suctioned off, and it is rewashed several times with diethyl ether. The residue is dissolved in 100 ml of water and 100 ml of dichloromethane while being stirred vigorously, and 32% NaOH solution is added until a pH of 10 is reached. The organic phase is separated, the aqueous phase is extracted three times with 50 ml each of dichloromethane, the combined organic phases are dried on magnesium sulfate and evaporated to the dry state.

Yield: 11.4 g (90% of theory) of a colorless solid Elementary analysis: Cld.: C, 41.29; H, 6.43; N, 17.19; I, 31.16. Fnd.: C, 41.44; H, 6.49; N, 17.07; I, 31.00.

d) 1,3,5-Triiodo-2,4,6-tris-(2-aza-4-methyl-3-oxobutane-1,4-diyl-{10-[1,4,7-tris-(carboxymethyl)-1,4,7,10-tetraazacyclododecanyl]})benzene 18.3 g (15 mmol) of 1,3,5-triiodo-2,4,6-tris-{2-aza-4-methyl-3-oxobutane-1,4-diyl-[10-(1,4,7,10-tetraazacyclododecanyl)]}benzene is dissolved in 75 ml of water, 19.5 g (206.5 mmol) of chloroacetic acid is added, and a pH of 9.5 is set at 60° C. with 32% NaOH. It is heated for 10 hours to 70° C., whereby the pH of the reaction mixture is continuously readjusted to 9.5. After cooling to room temperature, a pH of 1 is set with concentrated HCl, and the solution is concentrated by evaporation in a vacuum. The residue is absorptively precipitated with 250 ml of methanol, insoluble components are filtered off, and the filtrate is concentrated by evaporation. The residue is dissolved in 100 ml of water and added to an ion-exchange column (600 ml, IR 120, H$^+$-form). Then, it is washed with 2 l of water, and the acidic eluate is concentrated by evaporation. The residue is dissolved in 70 ml of methanol and added in drops in 900 ml of diethyl ether, the solid that accumulates in this case is suctioned off, rewashed several times with diethyl ether and dried in a vacuum.

Yield: 15.5 g (59% of theory) of a colorless solid Elementary analysis: Cld.: C, 41.32; H, 5.55; N, 12.05; I, 21.83. Fnd.: C, 41.56; H, 5.62; N, 12.01; I, 21.73.

e) 1,3,5-Triiodo-2,4,6-tris-(2-aza-4-methyl-3-oxobutane-1,4-diyl-{10-[1,4,7-tris-(carboxylatomethyl)-1,4,7,10-tetraazacyclododecanyl], Gd complex)benzene 12.0 g (6.9 mmol) of 1,3,5-triiodo-2,4,6-tris-(2-aza-4-methyl-3-oxobutane-1,4-diyl-{10-[1,4,7-tris-(carboxymethyl)-1,4,7,10-tetraazacyclododecanyl]})benzene is dissolved in 100 ml of water and acidified by adding 3 ml of acetic acid. 3.7 g (10.4 mmol) of gadolinium oxide is added, and it is refluxed for 6 hours. After complexing is completed, a pH of 7.4 is set with ammonia, and it is chromatographed on silica gel (mobile solvent:dichloromethane/methanol/ammonia: 10/10/1). The fractions that contain the product are combined and absorptively precipitated with 10 g of ion exchanger (IR 267 H-form) for 2 hours and filtered off, then it is absorptively precipitated with 10 g of ion exchanger (IRA 67 OH-form) for 2 hours, filtered off, mixed with 2 g of activated carbon, heated for 2 hours to 60° C., filtered off and freeze-dried.

Yield: 7.6 g (47% of theory) of a colorless solid Water content (Karl-Fischer): 5.2% Elementary analysis (relative to the anhydrous substance): Cld.: C, 32.66; H, 3.97; N, 9.52; I, 17.25; Gd, 21.38. Fnd.: C, 32.78; H, 3.99; N, 9.45; I, 17.21; Gd, 21.19.

EXAMPLE 11 a) 10-[4-Carbamido-1-methyl-2-oxo-3-azabutyl]-1,4,7,10-tetraazacyclododecane-1,4,7-triacetic acid-tert-butyl ester 17.8 g (130.5 mmol) of isobutyl chloroformate is added in drops at −20° C. to a solution of 76.5 g (118.7 mmol) of 10-[4-carboxy-1-methyl-2-oxo-3-azabutyl]1,4,7,10-tetraazacyclododecane-1,4,7-triacetic acid-tert-butyl ester (DE 19549286 A1, Schering AG, (Example 2d)) and 16.9 g (130.5 mmol) of diisopropylethylamine in 500 ml of THF. Then, it is stirred for 1 hour at −20° C. and carefully mixed with 20 ml of 25% aqueous ammonia solution. It is stirred for 2 more hours at 0° C., then, the solvent is distilled off in a vacuum, and the residue is chromatographed on silica gel (mobile solvent:dichloromethane/methanol 20:1). The fractions that contain the product are combined and concentrated by evaporation.

Yield: 61.1 g (80% of theory) of a colorless solid Elementary analysis: Cld.: C, 57.92; H, 9.09; N, 13.07. Fnd.: C, 58.11; H, 9.12; N, 12.99.

b) 1,3,5-Triiddo-2,4,6-tris-(2,5-diaza-3,6-dioxo-7-methylheptane-1,7-diyl-{10-[1,4,7-tris-(tert-butyloxycarbonylmethyl)-1,4,7,10-tetraazacyclo-dodecanyl]})benzene 44.6 g (70.6 mmol) of 10-[4-carbamido-1-methyl-2-oxo-3-azabutyl]-1,4,7,10-tetraazacyclododecane-1,4,7-triacetic acid-tert-butyl ester is dissolved in 500 ml of THF and mixed at 0° C. under argon with 1.71 g (71 mmol) of sodium hydride, and it is stirred for 1 hour at room temperature. Then, a solution of 20.2 g (20 mmol) of 1,3,5-triiodo-2,4,6-tris-(toluenesulfonyloxy)methylbenzene in 150 ml of THF is added in drops and stirred under reflux for 20 hours. After cooling, insoluble components are filtered out and evaporated to the dry state. The residue is taken up in 500 ml of ethyl acetate and extracted twice with 500 ml each of water. The organic phase is dried on sodium sulfate, the solvent is evaporated to the dry state, and the residue is chromatographed on silica gel (mobile solvent:dichloromethane/methanol 20:1). The fractions that contain the product are combined and concentrated by evaporation.

Yield: 15.1 g (31% of theory) of a colorless solid Elementary analysis: Cld.: C, 50.62; H, 7.37; N, 10.42; I, 15:73. Fnd.: C, 50.79; H, 7.41; N, 10.44; I, 15.64.

c) 1,3,5-Triiodo-2,4,6-tris-(2,5-diaza-3,6-dioxo-7-methylheptane-1,7-diyl-{10-[1,4,7-tris-(carboxymethyl)-1,4,7,10-tetraazacyclododecanyl]})benzene 18.2 g (7.5 mmol) of 1,3,5-triiodo-2,4,6-tris-(2,5-diaza-3,6-dioxo-7-methylheptane-1,7-diyl-{10-[1,4,7-tris-(tert-butyloxycarbonylmethyl)-1,4,7,10-tetraazacyclododecanyl]})benzene is dissolved in 75 ml of dichloromethane, mixed at 0° C. with 75 ml of trifluoroacetic acid and stirred for 3 hours at 0° C. The batch is poured into 500 ml of diethyl ether, the solid that accumulates is filtered off, rewashed three times with 100 ml each of diethyl ether and dried in a vacuum.

Yield: 14.1 g (98% of theory) of a colorless solid Elementary analysis: Cld.: C, 41.39; H, 5.53; N, 13.16; I, 19.88. Fnd.: C, 41.51; H, 5.57; N, 13.11; I, 19.67.

d) 1,3,5-Triiodo-2,4,6-tris-(2,5-diaza-3,6-dioxo-7-methylheptane-1,7-diyl-{10-[1,4,7-tris-(carboxylatomethyl)-1,4,7,10-tetraazacyclododecanyl]}, Gd complex)benzene 13.2 g (6.9 mmol) of 1,3,5-triiodo-2,4,6-tris-(2,5-diaza-3,6-dioxo-7-methylheptane-1,7-diyl-{10-[1,4,7-tris-(carboxymethyl)-1,4,7,10-tetraazacyclo-dodecanyl]})benzene is dissolved in 100 ml of water and acidified by adding 3 ml of acetic acid. 3.7 g (10.4 mmol) of gadolinium oxide is added, and it is refluxed for 6 hours. After complexing is completed, the pH is set at 7.4 with ammonia, and it is chromatographed on silica gel (mobile solvent:dichloromethane/methanol/ammonia: 10/10/1). The fractions that contain the product are combined and absorptively precipitated with 10 g of ion exchanger (IR 267 H-form) for 2 hours and filtered off, then it is absorptively precipitated with 10 g of ion exchanger (IRA 67 OH-form) for 2 hours, filtered off, mixed with 2 g of activated carbon, heated for 2 hours to 60° C., filtered off and freeze-dried.

Yield: 10.2 g (58% of theory) of a colorless solid Water content (Karl-Fischer): 6.2% Elementary analysis (relative to the anhydrous substance): Cld.: C, 33.34; H, 4.07; N, 10.60; I, 16.01; Gd, 19.84. Fnd.: C, 33.52; H, 4.12; N, 10.63; I, 15.89; Gd, 19.72.

EXAMPLE 12 a) 10-(4-Carbamido-2-oxo-3-azabutyl)-1,4,7,10-tetraazacyclododecane-1,4,7-triacetic acid-tert-butyl ester 17.8 g (130.5 mmol) of isobutyl chloroformate is added in drops at −20° C. to a solution of 74.8 g (118.7 mmol) of 10-(4-carboxy-2-oxo-3-azabutyl)-1,4,7,10-tetraazacyclododecane-1,4,7-triacetic acid-tert-butyl ester (DE 19549286 A1, Schering AG, (Example 1i)) and 16.9 g (130.5 mmol) of diisopropylethylamine in 500 ml of THF. Then, it is stirred for 1 hour at −20° C. and carefully mixed with 20 ml of 25% aqueous ammonia solution. It is stirred for 2 more hours at 0° C., and then the solvent is distilled off in a vacuum, and the residue is chromatographed on silica gel (mobile solvent:dichloromethane/methanol 20:1). The fractions that contain the product are combined and concentrated by evaporation.

Yield: 55.9 g (75% of theory) of a colorless solid Elementary analysis: Cld.: C, 57.30; H, 8.98; N, 13.36. Fnd.: C, 57.45; H, 8.99; N, 13.31.

b) 1,3,5-Triiodo-2,4,6-tris-(2,5-diaza-3,6-dioxoheptane-1,7-diyl-{10-[1,4,7-tris-(tert-butyloxycarbonylmethyl)-1,4,7,10-tetraazacyclododecanyl]})benzene 44.4 g (70.6 mmol) of 10-(4-carbamido-2-oxo-3-azabutyl)-1,4,7,10-tetraazacyclododecane-1,4,7-triacetic acid-tert-butyl ester is dissolved in 500 ml of THF and mixed at 0° C. under argon with 1.71 g (71 mmol) of sodium hydride, and it is stirred for 1 hour at room temperature. Then, a solution of 20.2 g (20 mmol) of 1,3,5-triiodo-2,4,6-tris-(toluenesulfonyloxy)methylbenzene in 150 ml of THF is added in drops and stirred under reflux for 20 hours. After cooling, insoluble components are filtered out, and it is evaporated to the dry state. The residue is taken up in 500 ml of ethyl acetate and extracted twice with 500 ml each of water. The organic phase is dried on sodium sulfate, the solvent is evaporated to the dry state, and the residue is chromatographed on silica gel (mobile solvent:dichloromethane/methanol 20:1). The fractions that contain the product are combined and concentrated by evaporation.

Yield: 16.2 g (34% of theory) of a colorless solid Elementary analysis: Cld.: C, 50.00; H, 7.25; N, 10.60; I, 16.01. Fnd.: C, 50.17; H, 7.28; N, 10.55; I, 15.89.

c) 1,3,5-Triiodo-2,4,6-tris-(2,5-diaza-3,6-dioxoheptane-1,7-diyl-{10-[1,4,7-tris-(carboxymethyl)-1,4,7,10-tetraazacyclododecanyl]})benzene 17.9 g (7.5 mmol) of 1,3,5-triiodo-2,4,6-tris-(2,5-diaza-3,6-dioxoheptane-1,7-diyl-{10-[1,4,7-tris-(tert-butyloxycarbonylmethyl)-1,4,7,10-tetraazacyclododecanyl]})benzene is dissolved in 75 ml of dichloromethane, mixed at 0° C. with 75 ml of trifluoroacetic acid and stirred for 3 hours at 0° C. The batch is poured into 500 ml of diethyl ether, the solid that accumulates is filtered off, rewashed three times with 100 ml each of diethyl ether and dried in a vacuum.

Yield: 13.5 g (96% of theory) of a colorless solid Elementary analysis: Cld.: C, 40.39; H, 5.33; N, 13.46; I, 20.32. Fnd.: C, 40.21; H, 5.27; N, 13.57; I, 20.22.

d) 1,3,5-Triiodo-2,4,6-tris-(2,5-diaza-3,6-dioxoheptane-1,7-diyl-{10-[1,4,7-tris-(carboxylatomethyl)-1,4,7,10-tetraazacyclododecanyl]}, Gd complex)benzene 12.9 g (6.9 mmol) of 1,3,5-triiodo-2,4,6-tris-(2,5-diaza-3,6-dioxoheptane-1,7-diyl-{10-[1,4,7-tris-(carboxymethyl)-1,4,7,10-tetraazacyclododecanyl]})benzene is dissolved in 100 ml of water and acidified by adding 3 ml of acetic acid. 3.7 g (10.4 mmol) of gadolinium oxide is added, and it is refluxed for 6 hours. After complexing is completed, the pH is set at 7.4 with ammonia, and it is chromatographed on silica gel (mobile solvent:dichloromethane/methanol/ammonia: 10/10/1). The fractions that contain the product are combined and absorptively precipitated with 10 g of ion exchanger (IR 267 H-form) for 2 hours and filtered off, then it is absorptively precipitated with 10 g of ion exchanger (IRA 67 OH-form) for 2 hours, filtered off, mixed with 2 g of activated carbon, heated for 2 hours to 60° C., filtered off and freeze-dried.

Yield: 10.6 g (61% of theory) of a colorless solid Water content (Karl-Fischer): 6.5% Elementary analysis (relative to the anhydrous substance): Cld.: C, 32.39; H, 3.88; N, 10.79; I, 16.30; Gd, 20.19. Fnd.: C, 32.51; H, 3.91; N, 10.75; I, 16.16; Gd, 20.01.

EXAMPLE 13 a) 2,4,6-Triiodo-1,3,5-tris-(2-tert-butoxycarbonylaminoethoxymethyl)benzene 142 g (450 mmol) of toluenesulfonic acid-2-tert-butoxycarbonylaminoethyl ester (Canne et al., *Tetrahedron Letters*, 38, 1997, 3361), dissolved in 250 ml of toluene, is added in drops to a mixture that consists of 50.0 g (91.4 mmol) of 1,3,5-triiodo-2,4,6-trishydroxymethylbenzene, and 3 g (8.7 mmol) of tetrabutylammonium hydrogen sulfate in 200 ml of 32% NaOH solution and 300 ml of toluene at room temperature, and then it is stirred for 12 hours. It is mixed with water and extracted twice with 300 ml each of toluene. The combined organic phases are dried on sodium sulfate, the solvent is evaporated to the dry state and chromatographed on silica gel (mobile solvent:hexane/ethyl acetate 10:1). The fractions that contain the product are combined and concentrated by evaporation.

Yield: 28.6 g (32% of theory) of a colorless solid Elementary analysis: Cld.: C, 36.94; H, 4.96; N, 4.31; I, 37.75. Fnd.: C, 36.98; H, 4.90; N, 4.27; I, 37.64.

b) 2,4,6-Triiodo-1,3,5-tris-(aminoethoxymethyl) benzene 24.4 g (25 mmol) of 2,4,6-triiodo-1,3,5-tris-(2-tert-butoxycarbonylaminoethoxymethyl)benzene is dissolved in 100 ml of dichloromethane, mixed at 0° C. with 100 ml of trifluoroacetic acid and stirred for 3 hours at 0° C. The batch is poured into 500 ml of diethyl ether, the solid that accumulates in this case is suctioned off and rewashed several times with diethyl ether. The residue is dissolved in 100 ml of water and 100 ml of dichloromethane while being stirred vigorously, and 32% NaOH solution is added until a pH of 10 is reached. The organic phase is separated, the aqueous phase is extracted three times with 50 ml each of dichloromethane, the combined organic phases are dried on magnesium sulfate and evaporated to the dry state.
Yield: 14.7 g (87% of theory) of a colorless solid Elementary analysis: Cld.: C, 26.69; H, 3.58; N, 6.22; I, 56.39. Fnd.: C, 26.78; H, 3.55; N, 6.16; I, 56.27.

c) 2,4,6-Triiodo-1,3,5-tris-{10-[1,4,7-tris-(benzyloxycarbonyl)-1,4,7,10-tetraazacyclododecanyl]aminoethoxymethyl } benzene 44.6 g (70.6 mmol) of 1,4,7-tris-(benzyloxycarbonyl)-10-(carboxymethyl)-1,4,7,10-tetrazacyclododecane, 21 ml (164 mmol) of triethylamine, 14.6 g (70.5 mmol) of dicyclohexylcarbodiimide and 8.1 g (70.5 mmol) of N-hydroxysuccinimide are added to a solution of 15.9 g (23.5 mmol) of 2,4,6-triiodo-1,3,5-tris-(aminoethoxymethyl)benzene in 400 ml DMF, and it is stirred for 20 hours at room temperature. Insoluble components are filtered out and evaporated to the dry state. The residue is taken up in 500 ml of ethyl acetate and extracted twice with 500 ml each of water. The organic phase is dried on sodium sulfate, the solvent is evapotated to the dry state, and the residue is chromatographed on silica gel (mobile solvent:dichloromethane/methanol 20:1). The fractions that contain the product are combined and concentrated by evaporation.
Yield: 29 g (49% of theory) of a colorless solid Elementary analysis: Cld.: C, 55.78; H, 5.52; N, 9.34; I, 15.11. Fnd.: C, 55.91; H, 5.62; N, 9.26; I, 14.89.

d) 2,4,6-Triiodo-1,3,5-tris-[10-(1,4,7,10-tetraazacyclododecanyl)aminoethoxymethyl]benzene 20 g (7.9 mmol) of 2,4,6-triiodo-1,3,5-tris-{10-[1,4,7-tris-(benzyloxycarbonyl)-1,4,7,10-tetraazacyclododecanyl] aminoethoxymethyl}benzene is carefully mixed at 0–5° C. with 140 ml of HBr/AcOH (33%) and stirred for 3 hours at room temperature. Then, the reaction mixture is poured into 800 ml of diethyl ether, the solid that accumulates in this case is suctioned off and rewashed several times with diethyl ether. The residue is dissolved in 100 ml of water and 100 ml of dichloromethane while being stirred vigorously, and 32% NaOH solution is added until a pH of 10 is reached. The organic phase is separated, the aqueous phase is extracted three times with 50 ml each of dichloromethane, the combined organic phases are dried on magnesium sulfate and evaporated to the dry state.
Yield: 10.1 g (97% of theory) of a colorless solid Elementary analysis: Cld.: C, 41.20; H, 6.45; N, 16.01; I, 29.02. Fnd.: C, 41.09; H, 6.42; N, 15.98; I, 28.87.

e) 2,4,6-Triiodo-1,3,5-tris-{10-[1,4,7-tris-(carboxymethyl)-1,4,7,10-tetraazacyclododecanyl] aminoethoxymethyl}benzene 17.7 g (13.5 mmol) of 2,4,6-triiodo-1,3,5-tris-[10-(1,4,7, 10-tetraazacyclododecanyl)aminoethoxymethyl]benzene is dissolved in 75 ml of water, 19.5 g (206.5 mmol) of chloroacetic acid is added, and a pH of 9.5 is set at 60° C. with 32% NaOH. It is heated for 10 hours to 70° C., whereby the pH of the reaction mixture is continuously readjusted to 9.5. After cooling to room temperature, the pH is set at 1 with concentrated HCl, and the solution is concentrated by evaporation in a vacuum. The residue is absorptively precipitated with 250 ml of methanol, insoluble components are filtered out, and the filtrate is concentrated by evaporation. The residue is dissolved in 100 ml of water and added to an ion-exchange column (600 ml, IR 120, H$^+$-form). Then, it is washed with 2 l of water, and the acidic eluate is concentrated by evaporation. The residue is dissolved in 70 ml of methanol and added in drops in 900 ml of diethyl ether, the solid that accumulates in this case is suctioned off, rewashed several times with diethyl ether and dried in a vacuum.
Yield: 14.4 g (58% of theory) of a colorless solid Elementary analysis: Cld.: C, 41.25; H, 5.60; N, 11.45; I, 20.76. Fnd.: C, 41.20; H, 5.48; N, 11.51; I, 20.59.

f) 2,4,6-Triiodo-1,3,5-tris-{10-[1,4,7-tris-(carboxylatomethyl)-1,4,7,10-tetraazacyclododecanyl, Gd complex]aminoethoxymethyl}benzene 12.7 g (6.9 mmol) of 2,4,6-triiodo-1,3,5-tris-{10-[1,4,7-tris-(carboxymethyl)-1,4,7,10-tetraazacyclododecanyl] aminoethoxymethyl}benzene is dissolved in 100 ml of water and acidified by adding 3 ml of acetic acid. 3.7 g (10.4 mmol) of gadolinium oxide is added, and it is refluxed for 6 hours. After complexing is completed, the pH is set at 7.4 with ammonia, and it is chromatographed on silica gel (mobile solvent:dichloromethane/methanol/ammonia: 10/10/1). The fractions that contain the product are combined and absorptively precipitated with 10 g of ion exchanger (IR 267 H-form) for 2 hours and filtered off, then absorptively precipitated with 10 g of ion exchanger (IRA 67 OH-form) for 2 hours, filtered off, mixed with 2 g of activated carbon, heated for 2 hours to 60° C., filtered off and freeze-dried.
Yield: 7.4 g (44% of theory) of a colorless solid Water content (Karl-Fischer): 5.9% Elementary analysis (relative to the anhydrous substance): Cld.: C, 32.94; H, 4.08; N, 9.15; I, 16.57; Gd, 20.54. Fnd.: C, 33.21; H, 4.12; N, 9.17; I, 16.35; Gd, 20.31.

EXAMPLE 14 a) 2,4,6-Triiodo-5-[2-(2,2,2-trifluoroacetylamino)-acetylamino]-isophthalic acid dichloride 14.5 ml (200 mmol) of thionyl chloride is added in drops at 0° C. within 1 hour to a solution of 34.2 g (200 mmol) of glycine trifluoroacetate in 200 ml of dimethylacetamide. Then, 23.8 g (40 mmol) of 5-amino-2,4,6-triiodoisophthalic acid dichloride (DE 2943777, Schering AG, (priority: Oct. 26, 1979)) is added at 0° C. and stirred for 4 days at room temperature. The reaction mixture is poured into 5liters of ice water and the solid that accumulates is filtered off. For further purification, the filter residue is dissolved in 1000 ml of ethyl acetate, shaken out twice with saturated sodium bicarbonate solution, the organic phase is dried on sodium sulfate, and the solvent is concentrated by evaporation in a vacuum.

Yield: 29.3 g (97% of theory) of a colorless solid Elementary analysis: Cld.: C, 19.25; H, 0.54; N, 3.74. Fnd.: C, 19.39; H, 0.57; N, 3.72.

b) 5-(2-Aminoacetylamino)-N N-bis-(2-aminoethyl)-2,4,6-triiodoisophthalic acid amide A solution of 10 g (13.3 mmol) of 2,4,6-triiodo-5-[2-(2, 2,2-trifluoroacetylamino)-acetylamino]-isophthalic acid dichloride in 100 ml of tetrahydrofuran is added in drops to 26.7 ml (399 mmol) of ethylenediamine over 1 hour at room temperature, and it is stirred for 14 more hours. The solid that accumulates is filtered off, rewashed with ethanol, taken up in 100 ml of water, and the pH is set at 8.0 with 1 M lithium hydroxide solution. After concentration by evaporation in a vacuum, it is recrystallized from ethanol.

Yield: 6.4 g (68% of theory) of a colorless solid Elementary analysis: Cld.: C, 24.02; H, 2.74; N, 12.01; I, 54.38. Fnd.: C, 24.276; H, 2.79; N, 11.98; I, 54.25.

c) 2,4,6-Triiodo-5-(3,6-diaza-1,4,7-trioxo-8-methyloctane-1,8-diyl-{10-[1,4,7-tris-(carboxylatomethyl)-1,4,7,10-tetraazacyclododecanyl, Gd complex]}) aminoisophthalic acid-N,N-bis-(3,6-diaza-4,7-dioxo-8-methyloctane-1,8-diyl-{10-[1,4,7-tris-(carboxylatomethyl)-1,4,7,10-tetraazacyclododecanyl, Gd complex]})amide 9.6 g (15.2 mmol) of the Gd complex of 10-[4-carboxy-2-oxo-3-aza-1-methylbutyl]1,4,7,10-tetraazacyclododecane-1,4,7-triacetic acid (WO 98/24775, Schering AG, (Example 1)) is suspended in 100 ml of DMSO and mixed with 1.96 g (17 mmol) of N-hydroxysuccinimide and 3.3 g (16 mmol) of dicyclohexylcarbodiimide and preactivated for 1 hour. Then, it is mixed with 2.4 g (3.4 mmol) of 5-(2-aminoacetylamino)-N,N-bis-(2-aminoethyl)-2,4,6-triiodo-isophthalic acid amide and stirred for 3 days at room temperature under nitrogen. Insoluble components are filtered off, and the solution is poured into 1000 ml of acetone. The solid that accumulates in this case is filtered off and washed in portions with 300 ml of acetone and with 100 ml of diethyl ether. The residue is taken up in 200 ml of water and absorptively precipitated for 2 hours with 30 g of ion exchanger (IRA 67 OH-form) and filtered off. Then, it is absorptively precipitated for 2 hours with 10 g of ion exchanger (IR 267 H-form), filtered off, mixed with 2 g of activated carbon, heated for 2 hours to 60° C., filtered off, and the solution is concentrated by evaporation to 100 ml. To remove the residual dimethyl sulfoxide, the solution is poured into 1000 ml of acetone, and the precipitate that accumulates is filtered off. The residue is dissolved in 250 ml of water, the conductivity is set at a value of 0.005 mS (pH=7.0) with a little ion exchanger (H-form and OH-form), it is filtered off and concentrated by evaporation in a vacuum.

Yield: 5.7 g (62% of theory) of a colorless solid Water content (Karl-Fischer): 5.7% Elementary analysis (relative to the anhydrous substance): Cld.: C, 33.64; H, 4.09; N, 11.60; I, 15.02; Gd, 18.61. Fnd.: C, 33.77; H, 4.13; N, 11.54; I, 15.00; Gd, 18.53.

EXAMPLE 15 a) 2,4,6-Triiodo-5-(3,6-diaza-1,4,7-trioxooctane-1,8-diyl-{10-[1,4,7-tris-(carboxylatomethyl)-1,4,7,10-tetraazacyclododecanyl, Gd complex]})aminoisophthalic acid-N,N-bis-(3,6-diaza-4,7-dioxooctane-1,8-diyl-{10-[1,4,7-tris-(carboxylatomethyl)-1,4,7,10-tetraazacyclododecanyl, Gd complex]})amide 9.4 g (15.2 mmol) of the Gd complex of 10-[4-carboxy-2-oxo-3-azabutyl]-1,4,7,10-tetraazacyclododecane-1,4,7-triacetic acid (WO 98/24775, Schering AG, (Example 11)) is suspended in 100 ml of DMSO and mixed with 1.96 g (17 mmol) of N-hydroxysuccinimide and 3.3 g (16 mmol) of dicyclohexylcarbodiimide and preactivated for 1 hour. Then, it is mixed with 2.4 g (3.4 mmol) of 5-(2-aminoacetylamino)-N,N-bis-(2-aminoethyl)-2,4,6-triiodoisophthalic acid amide, and it is stirred for 3 days at room temperature under nitrogen. Insoluble components are filtered out, and the solution is poured into 1000 ml of acetone. The solid that accumulates in this case is filtered off and mixed in portions with 300 ml of acetone and washed with 100 ml of diethyl ether. The residue is taken up in 200 ml of water and absorptively precipitated for 2 hours with 30 g of ion exchanger (IRA 67 OH-form) and filtered off. Then, it is absorptively precipitated for 2 hours with 10 g of ion exchanger (IR 267 H-form), filtered off, mixed with 2 g of activated carbon, heated for 2 hours to 60° C., filtered off, and the solution is concentrated by evaporation to 100 ml. To remove the residual dimethyl sulfoxide, the solution is poured into 1000 ml of acetone, and the precipitate that accumulates is filtered off. The residue is dissolved in 250 ml of water, the conductivity is set at a value of 0.005 mS (pH=7.0) with a little ion exchanger (H-form and OH-form), it is filtered off and concentrated by evaporation in a vacuum.

Yield: 6.1 g (67% of theory) of a colorless solid Water content (Karl-Fischer): 6.4% Elementary analysis (relative to the anhydrous substance): Cld.: C, 32.76; H, 3.92; N, 11.80; I, 15.27; Gd, 18.92. Fnd.: C, 32.91; H, 3.98; N, 11.81; I, 15.11; Gd, 18.67.

EXAMPLE 16 a) 2,4,6-Triiodo-5-(3-aza-1,4-dioxopentane-1,5-diyl-{10-[1,4,7-tris-(benzyloxycarbonyl)-1,4,7,10-tetraazacyclododecanyl]})aminoisophthalic acid-N,N-bis-(3-aza-4-oxopentane-1,5-diyl-{10-[1,4,7-tris-(benzyloxycarbonyl)-1,4,7,10-tetraazacyclododecanyl]})amide 44.6 g (70.6 mmol) of 1,4,7-tris-(benzyloxycarbonyl)-10-(carboxymethyl)-1,4,7,10-tetrazacyclododecane, 21 ml (164 mmol) of triethylamine, 14.6 g (70.5 mmol) of dicyclohexylcarbodiimide and 8.1 g (70.5 mmol) of N-hydroxysuccinimide are added to a suspension of 16.5 g (23.5 mmol) of 5-(2-aminoacetylamino)-N,N-bis-(2-aminoethyl)-2,4,6-triiodoisophthalic acid amide in 446 ml DMF, and it is stirred for 20 hours at room temperature. Insoluble components are filtered out, and it is evaporated to the dry state. The residue is taken up in 500 ml of ethyl acetate and extracted twice with 500 ml each of water. The organic phase is dried on sodium sulfate, the solvent is evaporated to the dry state, and the residue is chromatographed on silica gel (mobile solvent: dichloromethane/methanol 20:1). The fractions that contain the product are combined and concentrated by evaporation.

Yield: 30.5 g (51% of theory) of a colorless solid Elementary analysis: Cld.: C, 54.76; H, 5.27; N, 9.91; I, 14.96. Fnd.: C, 54.99; H, 5.35; N, 9.87; I, 14.65.

b) 2,4,6-Triiodo-5-(3-aza-1,4-dioxopentane-1,5-diyl-{10-[1,4,7,10-tetraazacyclododecanyl]})aminoisophthalic acid-N,N-bis-(3-aza-4-oxopentane-1,5-diyl-{10-[1,4,7,10-tetraazacyclododecanyl]})amide 20 g (7.9 mmol) of 2,4,6-triiodo-5-(3-aza-1,4-dioxopentane-1,5-diyl-{10-[1,4,7-tris-(benzyloxycarbonyl)-1,4,7,10-tetraazacyclododecanyl]})aminoisophthalic acid-N,N-bis-(3-aza-4-oxopentane-1,5-diyl-{10-[1,4,7-tris-(benzyloxycarbonyl)-1,4,7,10-tetraazacyclododecanyl]})amide is carefully mixed at 0–5° C. [with] 140 ml of HBr/AcOH (33%) and stirred for 3 hours at room temperature. Then, the reaction mixture is poured into 800 ml of diethyl ether, the solid that accumulates in this case is suctioned off, and it is rewashed several times with diethyl ether. The residue is dissolved in 100 ml of water and 100 ml of dichloromethane while being stirred vigorously, and 32% NaOH solution is added until a pH of 10 is reached. The organic phase is separated, the aqueous phase is extracted three times with 50 ml each of dichloromethane, the combined organic phases are dried on magnesium sulfate, and it is evaporated to the dry state.

Yield: 10.1 g (96% of theory) of a colorless solid Elementary analysis: Cld.: C, 39.53; H, 5.96; N, 18.86; I, 28.48. Fnd.: C, 39.44; H, 5.99; N, 18.91; I, 28.51.

c) 2,4,6-Triiodo-5-(3-aza-1,4-dioxopentane-1,5-diyl-{10-[1,4,7-tris-(carboxymethyl)-1,4,7,10-tetraazacyclododecanyl]})aminoisophthalic acid-N,N-bis-(3-aza-4-oxopentane-1,5-diyl-{10-[1,4,7-tris-(carboxymethyl)-1,4,7,10-tetraazacyclododecanyl]})amide 18.0 g (13.5 mmol) of 2,4,6-triiodo-5-(3-aza-1,4-dioxopentane-1,5-diyl-{10-[1,4,7,10-tetraazacyclododecanyl]})aminoisophthalic acid-N,N-bis-(3-aza-4-oxopentane-1,5-diyl-{10-[1,4,7,10-tetraazacyclododecanyl]})amide is dissolved in 75 ml of water, 19.5 g (206.5 mmol) of chloroacetic acid is added, and a pH of 9.5 is set at 60° C. with 32% NaOH. It is heated for 10 hours to 70° C., whereby the pH of the reaction mixture is readjusted continuously to 9.5. After cooling to room temperature, the pH is set at 1 with concentrated HCl, and the solution is concentrated by evaporation in a vacuum. The residue is absorptively precipitated with 250 ml of methanol, insoluble components are filtered out, and the filtrate is concentrated by evaporation. The residue is dissolved in 100 ml of water and added to an ion-exchange column (600 ml, IR 120, H+-form). Then, it is washed with 2 l of water, and the acidic eluate is concentrated by evaporation. The residue is dissolved in 70 ml of methanol and added in drops to 900 ml of diethyl ether, the solid that accumulates in this case is suctioned off, rewashed several times with diethyl ether and dried in a vacuum.

Yield: 15.3 g (61% of theory) of a colorless solid Elementary analysis: Cld.: C, 40.05; H, 5.26; N, 13.56; I, 20.65. Fnd.: C, 40.22; H, 5.29; N, 13.49; I, 20.56.

d) 2,4,6-Triiodo-5-(3-aza-1,4-dioxopentane-1,5-diyl-{10-[1,4,7-tris-(carboxylatomethyl)-1,4,7,10-tetraazacyclododecanyl, Gd complex]})aminoisophthalic acid-N,N-bis-(3-aza-4-oxopentane-1,5-diyl-{10-[1,4,7-tris-(carboxylatomethyl)-1,4,7,10-tetraazacyclododecanyl, Gd complex]})amide 12.8 g (6.9 mmol) of 2,4,6-triiodo-5-(3-aza-1,4-dioxopentane-1,5-diyl-{10-[1,4,7-tris-(carboxymethyl)-1,4,7,10-tetraazacyclododecanyl]})aminoisophthalic acid-N,N-bis-(3-aza-4-oxopentane-1,5-diyl-{10-[1,4,7-tris-(carboxymethyl)-1,4,7,10-tetraazacyclododecanyl]})amide is dissolved in 100 ml of water and acidified by adding 3 ml of acetic acid. 3.7 g (10.4 mmol) of gadolinium oxide is added, and it is refluxed for 6 hours. After complexing is completed, the pH is set at 7.4 with ammonia, and it is chromatographed on silica gel (mobile solvent:dichloromethane/methanol/ammonia: 10/10/1). The fractions that contain the product are combined and absorptively precipitated with 10 g of ion exchanger (IR 267 H-form) for 2 hours and filtered off, then absorptively precipitated with 10 g of ion exchanger (IRA 67 OH-form) for 2 hours, filtered off, mixed with 2 g of activated carbon, heated for 2 hours to 60° C., filtered off and freeze-dried.

Yield: 8.3 g (48% of theory) of a colorless solid Water content (Karl-Fischer): 6.9% Elementary analysis (relative to the anhydrous substance): Cld.: C, 32.07; H, 3.82; N, 10.86; I, 16.40; Gd, 20.32. Fnd.: C, 32.21; H, 3.85; N, 10.89; I, 16.25; Gd, 20.19.

EXAMPLE 17 a) 2,4,6-Triiodo-5-(3-aza-1,4-dioxo-5-methylpentane-1,5-diyl-{10-[1,4,7-tris-(benzyloxycarbonyl)-1,4,7,10-tetraazacyclododecanyl]})aminoisophthalic acid-N,N-bis-(3-aza-5-methyl-4-oxopentane-1,5-diyl-{10-[1,4,7-tris-(benzyloxycarbonyl)-1,4,7,10-tetraazacyclododecanyl]})amide 45.7 g (70.6 mmol) of 1,4,7-tris-(benzyloxycarbonyl)-10-(1-carboxyethyl)-1,4,7,10-tetrazacyclododecane, 21 ml (164 mmol) of triethylamine, 14.6 g (70.5 mmol) of dicyclohexylcarbodiimide and 8.1 g (70.5 mmol) of N-hydroxysuccinimide are added to a suspension of 16.5 g (23.5 mmol) of 5-(2-aminoacetylamino)-N,N-bis-(2-aminoethyl)-2,4,6-triiodoisophthalic acid amide in 446 ml DMF, and it is stirred for 20 hours at room temperature. Insoluble components are filtered out, and it is evaporated to the dry state. The residue is taken up in 500 ml of ethyl acetate and extracted twice with 500 ml each of water. The organic phase is dried on sodium sulfate, the solvent is evaporated to the dry state, and the residue is chromatographed on silica gel (mobile solvent: dichloromethane/methanol 20:1). The fractions that contain the product are combined and concentrated by evaporation.

Yield: 28.6 g (47% of theory) of a colorless solid Elementary analysis: Cld.: C, 55.27; H, 5.42; N, 9.75; I, 14.72. Fnd.: C, 55.34; H, 5.44; N, 9.79; I, 14.65.

b) 2,4,6-Triiodo-5-(3-aza-1,4-dioxo-5-methylpentane-1,5-diyl-{10-[1,4,7,10-tetraazacyclododecanyl]})aminoisophthalic acid-N,N-bis-(3-aza-5-methyl-4-oxopentane-1,5-diyl-{10-[1,4,7,10-tetraazacyclododecanyl]})amide 20 g (7.7 mmol) of 2,4,6-triiodo-5-(3-aza-1,4-dioxo-5-methylpentane-1,5-diyl-{10-[1,4,7-tris-(benzyloxycarbonyl)-1,4,7,10-tetraazacyclododecanyl]})aminoisophthalic acid-N,N-bis-(3-aza-5-methyl-4-oxopentane-1,5-diyl-{10-[1,4,7-tris-(benzyloxycarbonyl)-1,4,7,10-tetraazacyclododecanyl]})amide are carefully mixed at 0–5° C. [with] 140 ml of HBr/AcOH (33%) and stirred for 3 hours at room temperature. Then, the reaction mixture is poured into 800 ml of diethyl ether, the solid that accumulates in this case is suctioned off and rewashed several times with diethyl ether. The residue is dissolved in 100 ml of water and 100 ml of dichloromethane while being stirred vigorously, and 32% NaOH solution is added until a pH of 10 is reached. The organic phase is separated, the aqueous phase is extracted three times with 50 ml each of dichloromethane, the combined organic phases are dried on magnesium sulfate and evaporated to the dry state.

Yield: 10.2 g (96% of theory) of a colorless solid Elementary analysis: Cld.: C, 40.94; H, 6.21; N, 18.28; I, 27.61. Fnd.: C, 41.13; H, 6.17; N, 18.32; I, 27.47.

c) 2,4,6-Triiodo-5-(3-aza-1,4-dioxo-5-methylpentane-1,5-diyl-{10-[1,4,7-tris-(carboxymethyl)-1,4,7,10-tetraazacyclododecanyl]})aminoisophthalic acid-N,N-bis-(3-aza-5-methyl-4-oxopentane-1,5-diyl-{10[1,4,7-tris-(carboxymethyl)-1,4,7,10-tetraazacyclododecanyl]})amide 18.6 g (13.5 mmol) of 2,4,6-triiodo-5-(3-aza-1,4-dioxo-5-methylpentane-1,5-diyl-{10-[1,4,7,10-tetraazacyclododecanyl]})aminoisophthalic acid-N,N-bis-(3-aza-5-methyl-4-oxopentane-1,5-diyl-{10-[1,4,7,10-tetraazacyclododecanyl]}) amide is dissolved in 75 ml of water, 19.5 g (206.5 mmol) of chloroacetic acid is added, and the pH is set at 9.5 at 60° C. with 32% NaOH. It is heated for 10 hours to 70° C., whereby the pH of the reaction mixture is readjusted continuously to 9.5. After cooling to room temperature, a pH of 1 is set with concentrated HCl, and the solution is concentrated by evaporation in a vacuum. The residue is absorptively precipitated with 250 ml of methanol, insoluble components are filtered out, and the filtrate is concentrated by evaporation. The residue is dissolved in 100 ml of water and added to an ion-exchange column (600 ml, IR 120, H+-form). Then, it is washed with 2 l of water, and the acidic eluate is concentrated by evaporation. The residue is dissolved in 70 ml of methanol and added in drops in 900 ml of diethyl ether, the solid that accumulates in this case is suctioned off, rewashed several times with diethyl ether, and dried in a vacuum.

Yield: 14.1 g (55%) of a colorless solid Elementary analysis: Cld.: C, 41.06; H, 5.46; N, 13.26; I, 20.02. Fnd.: C, 41.34; H, 5.52; N, 13.31; I, 19.69.

d) 2,4,6-Triiodo-5-(3-aza-1,4-dioxo-5-methylpentane-1,5-diyl-{10-[1,4,7-tris-(carboxylatomethyl)-1,4,7,10-tetraazacyclododecanyl, Gd complex]})aminoisophthalic acid-N,N-bis-(3-aza-5-methyl-4-oxopentane-1,5-diyl-{10-[1,4,7-tris-(carboxylatomethyl)-1,4,7,10-tetraazacyclododecanyl, Gd complex]})amide, 13.1 g (6.9 mmol) of 2,4,6-triiodo-5-(3-aza-1,4-dioxo-5-methylpentane-1,5-diyl-{10-[1,4,7-tris-(carboxymethyl)-1,4,7,10-tetraazacyclododecanyl]})aminoisophthalic acid-N,N-bis-(3-aza-5-methyl-4-oxopentane-1,5-diyl-{10-[1,4,7-tris-(carboxymethyl)-1,4,7,10-tetraazacyclododecanyl]}) amide is dissolved in 100 ml of water and acidified by adding 3 ml of acetic acid. 3.7 g (10.4 mmol) of gadolinium oxide is added, and it is refluxed for 6 hours. After complexing is completed, a pH of 7.4 is set with ammonia, and it is chromatographed on silica gel (mobile solvent:dichloromethane/methanol/ammonia: 10/10/1). The fractions that contain the product are combined and absorptively precipitated with 10 g of ion exchanger (IR 267 H-form) for 2 hours and filtered off, then absorptively precipitated with 10 g of ion exchanger (IRA 67 OH-form) for 2 hours, filtered off, mixed with 2 g of activated carbon, heated for 2 hours to 60° C., filtered off and freeze-dried.

Yield: 7.6 g (44% of theory) of a colorless solid Water content (Karl-Fischer): 5.3% Elementary analysis (relative to the anhydrous substance): Cld.: C, 33.02; H, 4.01; N, 10.66; I, 16.10; Gd, 19.96. Fnd.: C, 33.34; H, 4.08; N, 10.62; I, 16.01; Gd, 19.82.

EXAMPLE 18 a) 2,4,6-Triiodo-5-{methyl[2-(2,2,2-trifluoroacetylamino)-acetyl]amino}-isophthalic acid dichloride 14.5 ml (200 mmol) of thionyl chloride is added in drops at 0° C. within 1 hour to a solution of 34.2 g (200 mmol) of glycine trifluoroacetate in 200 ml of dimethylacetamide. Then, 24.4 g (40 mmol) of 5-amino-2,4,6-triiodoisophthalic acid dichloride (EP 0033426, Sovak, 1/80 US) is added at 0° C., and it is stirred for 4 days at room temperature. The reaction mixture is poured into 5 liters of ice water, and the solid that accumulates is filtered off. For further purification, the filter residue is dissolved in 1000 ml of ethyl acetate, shaken out twice with saturated sodium bicarbonate solution, the organic phase is dried on sodium sulfate, and the solvent is concentrated by evaporation in a vacuum.

Yield: 28.7 g (94% of theory) of a colorless solid Elementary analysis: Cld.: C, 20.47; H, 0.79; N, 3.67. Fnd.: C, 20.52; H, 0.77; N, 3.71.

b) 5-[(2-Aminoacetyl)-methylamino]-N,N-bis-(2-aminoethyl)-2,4,6-triiodoisophthalic acid amide A solution of 10 g (13.1 mmol) of 2,4,6-triiodo-5-{methyl-[2-(2,2,2-trifluoroacetylamino)-acetyl]-amino}-isophthalic acid dichloride in 100 ml of tetrahydrofuran is added in drops to 26.7 ml (399 mmol) of ethylenediamine-over 1 hour at room temperature, and it is stirred for 14 more hours. The precipitated solid is filtered off, rewashed with ethanol, taken up in 100 ml of water, and a pH of 8.0 is set with 1 M lithium hydroxide solution. After concentration by evaporation in a vacuum, it is recrystallized from ethanol.

Yield: 7.3 g (78% of theory) of a colorless solid Elementary analysis: Cld.: C, 25.23; H, 2.96; N, 11.77; I, 53.31. Fnd.: C, 25.44; H, 2.98; N, 11.81; I, 53.09.

c) 2,4,6-Triiodo-5-(3-aza-1,4-dioxopentan-1,5-diyl-{10-[1,4,7-tris-(benzyloxycarbonyl)-1,4,7,10-tetraazacyclododecanyl]})-methylaminoisophthalic acid-N,N-bis-(3-aza-4-oxopentane-1,5-diyl-{10-[1,4,7-tris-(benzyloxycarbonyl)-1,4,7,10-tetraazacyclododecanyl]})-amide 44.6 g (70.6 mmol) of 1,4,7-tris-(benzyloxycarbonyl)-10-(carboxymethyl)-1,4,7,10-tetrazacyclododecane, 21 ml (164 mmol) of triethylamine, 14.6 g (70.5 mmol) of dicyclohexylcarbodiimide and 8.1 g (70.5 mmol) of N-hydroxysuccinimide are added to a suspension of 16.8 g (23.5 mmol) of 5-[(2-aminoacetyl)-methylamino]-N,N-bis-(2-aminoethyl)-2,4,6-triiodoisophthalic acid amide in 446 ml of DMF, and it is stirred for 20 hours at room temperature. Insoluble components are filtered out, and it is evaporated to the dry state. The residue is taken up in 500 ml of ethyl acetate, and it is extracted twice with 500 ml each of water. The organic phase is dried on sodium sulfate, the solvent is evaporated to the dry state, and the residue is chromatographed on silica gel (mobile solvent:dichloromethane/methanol 20:1). The fractions that contain the product are combined and concentrated by evaporation.

Yield: 34.9 g (58% of theory) of a colorless solid Elementary analysis: Cld.: C, 54.93; H, 5.32; N, 9.86; I, 14.88. Fnd.: C, 55.12; H, 5.39; N, 9.81; I, 14.72.

d) 2,4,6-Triiodo-5-(3-aza-1,4-dioxopentane-1,5-diyl-{10-[1,4,7,10-tetraazacyclododecanyl]})-methylaminoisophthalic acid-N,N-bis-(3-aza-4-oxopentane-1,5-diyl-{10-[1,4,7,10-tetraazacyclododecanyl]})-amide 20 g (7.8 mmol) of 2,4,6-triiodo-5-(3-aza-1,4-dioxopentane-1,5-diyl-{10-[1,4,7-tris-(benzyloxycarbonyl)-1,4,7,10-tetraazacyclododecanyl]})methylaminoisophthalic acid-N,N-bis-(3-aza-4-oxopentane-1,5-diyl-{10-[1,4,7-tris-(benzyloxycarbonyl)-1,4,7,10-tetraazacyclododecanyl]})-amide is carefully mixed at 0–5° C. [with] 140 ml of HBr/AcOH (33%) and stirred for 3 hours at room temperature. Then, the reaction mixture is poured into 800 ml of diethyl ether, the solid that accumulates in this case is suctioned off and rewashed several times with diethyl ether. The residue is dissolved in 100 ml of water and 100 ml of dichloromethane while being stirred vigorously, and 32% NaOH solution is added until a pH of 10 is reached. The organic phase is separated, the aqueous phase is extracted three times with 50 ml each of dichloromethane, the combined organic phases are dried on magnesium sulfate, and it is evaporated to the dry state.

Yield: 10.0 g (95% of theory) of a colorless solid Elementary analysis: Cld.: C, 40.01; H, 6.04; N, 18.66; I, 28.18. Fnd.: C, 40.19; H, 6.07; N, 18.62; I, 28.03.

e) 2,4,6-Triiodo-5-(3-aza-1,4-dioxopentane-1,5-diyl-{10-[1,4,7-tris-(carboxymethyl)-1,4,7,10-tetraazacyclododecanyl]})-methylaminoisophthalic acid-N,N-bis-(3-aza-4-oxopentane-1,5-diyl-{10-[1,4,7-tris-(carboxymethyl)-1,4,7,10-tetraazacyclododecanyl]})-amide 18.2 g (13.5 mmol) of 2,4,6-triiodo-5-(3-aza-1,4-dioxopentane-1,5-diyl-{10-[1,4,7,10-tetraazacyclododecanyl]})-methylaminoisophthalic acid-N,N-bis-(3-aza-4-oxopentane-1,5-diyl-{10-[1,4,7,10-tetraazacyclododecanyl]})-amide is dissolved in 75 ml of water, 19.5 g (206.5 mmol) of chloroacetic acid is added, and a pH of 9.5 is set at 60° C. with 32% NaOH. It is heated for 10 hours to 70° C., whereby the pH of the reaction mixture is readjusted continuously to 9.5. After cooling to room temperature, a pH of 1 is set with concentrated HCl, and the solution is concentrated by evaporation in a vacuum. The residue is absorptively precipitated with 250 ml of methanol, insoluble components are filtered out, and the filtrate is concentrated by evaporation. The residue is dissolved in 100 ml of water and added to an ion-exchange column (600 ml, IR 120, H⁺-form). Then, it is washed with 2 l of water, and the acidic eluate is concentrated by evaporation. The residue is dissolved in 70 ml of methanol and added in drops in 900 ml of diethyl ether, the solid that accumulates in this case is suctioned off, rewashed several times with diethyl ether and dried in a vacuum.

Yield: 15.0 g (59% of theory) of a colorless solid Elementary analysis: Cld.: C, 40.39; H, 5.33; N, 13.46; I, 20.32. Fnd.: C, 40.53; H, 5.37; N, 13.41; I, 20.17.

f) 2,4,6-Triiodo-5-(3-aza-1,4-dioxopentane-1,5-diyl-{10-[1,4,7-tris-(carboxylatomethyl)-1,4,7,10-tetraazacyclododecanyl, Gd complex]})-methylaminoisophthalic acid-N,N-bis-(3-aza-4-oxopentane-1,5-diyl-{10-[1,4,7-tris-(carboxylatomethyl)-1,4,7,10-tetraazacyclododecanyl, Gd complex]})-amide 12.9 g (6.9 mmol) of 2,4,6-triiodo-5-(3-aza-1,4-dioxopentane-1,5-diyl-{10-[1,4,7-tris-(carboxymethyl)-1,4,7,10-tetraazacyclododecanyl]})-methylaminoisophthalic acid-N,N-bis-(3-aza-4-oxopentane-1,5-diyl-{10-[1,4,7-tris-(carboxymethyl)-1,4,7,10-tetraazacyclododecanyl]})-amide is dissolved in 100 ml of water and acidified by adding 3 ml of acetic acid. 3.7 g (10.4 mmol) of gadolinium oxide is added, and it is refluxed for 6 hours. After complexing is completed, a pH of 7.4 is set with ammonia, and it is chromatographed on silica gel (mobile solvent:dichloromethane/methanol/ammonia: 10/10/1). The fractions that contain the product are combined and absoritively precipitated with 10 g of ion exchanger (IR 267 H-form) for 2 hours and filtered off, then absorptively precipitated with 10 g of ion exchanger (IRA 67 OH-form) for 2 hours, filtered off, mixed with 2 g of activated carbon, heated for 2 hours to 60° C., filtered off and freeze-dried.

Yield: 8.7 g (51% of theory) of a colorless solid Water content (Karl-Fischer): 5.8% Elementary analysis (relative to the anhydrous substance): Cld.: C, 32.39; H, 3.88; N, 10.79; I, 16.30; Gd, 20.19. Fnd.: C, 32.48; H, 3.91; N, 10.76; I, 16.21; Gd, 20.08.

EXAMPLE 19 a) 5-[3-(2-Aminoethyl)-ureido]-N,N-bis-(2-aminoethyl)-2,4,6-triiodoisophthalic acid amide 100 ml of a 2 M solution of phosgene in toluene is carefully added to a solution of 29.8 g (50 mmol) of 5-amino-2,4,6-triiodoisophthalic acid dichloride (DE 2943777, Schering AG, (priority: Oct. 26, 1979)) in 250 ml of dioxane, and it is heated for 24 hours to 60° C. Then, the solution is concentrated by evaporation in a vacuum at 80° C., whereby the gases are directed through a 20% aqueous NaOH solution. The residue is dissolved in 200 ml of tetrahydrofuran and added in drops to 66.9 ml (1.0 mol) of ethylenediamine over 1 hour at room temperature, and it is stirred for 24 more hours. The solid that accumulates is filtered off, rewashed with ethanol, taken up in 200 ml of water, and a pH of 8.0 is set with 1 M lithium hydroxide solution. After concentration by evaporation in a vacuum, it is recrystallized from ethanol.

Yield: 19.4 g (53% of theory) of a colorless solid Elementary analysis: Cld.: C, 24.71; H, 3.04; N, 13.45; I, 52.22. Fnd.: C, 24.91; H, 3.09; N, 13.36; I, 51.97.

b) 2,4,6-Triiodo-5-(2,5-diaza-1,6-dioxoheptane-1,7-diyl-{10-[1,4,7-tris-(benzyloxycarbonyl)-1,4,7,10-tetraazacyclododecanyl]})-aminoisophthalic acid-N,N-bis-(3-aza-4-oxopentane-1,5-diyl-{10-[1,4,7-tris-(benzyloxycarbonyl)-1,4,7,10-tetraazacyclododecanyl]})-amide 44.6 g (70.6 mmol) of 1,4,7-tris-(benzyloxycarbonyl)-10-(carboxymethyl)-1,4,7,10-tetrazacyclododecane, 21 ml (164 mmol) of triethylamine, 14.6 g (70.5 mmol) of dicyclohexylcarbodiimide and 8.1 g (70.5 mmol) of N-hydroxysuccinimide are added to a suspension of 17.1 g (23.5 mmol) of 5-[3-(2-aminoethyl)-ureido]-N,N-bis-(2-aminoethyl)-2,4,6- triiodoisophthalic acid amide in 446 ml DMF, and it is stirred for 20 hours at room temperature. Insoluble components are filtered out, and it is evaporated to the dry state. The residue is taken up in 500 ml of ethyl acetate and extracted twice with 500 ml each of water. The organic phase is dried on sodium sulfate, the solvent is evaporated to the dry state, and the residue is chromatographed on silica gel (mobile solvent:dichloromethane/methanol 20:1). The fractions that contain the product are combined and concentrated by evaporation.

Yield: 32.7 g (54% of theory) of a colorless solid Elementary analysis: Cld.: C, 54.61; H, 5.33; N, 10.24; I, 14.80. Fnd.: C, 54.81; H, 5.35; N, 10.13; I, 14.72.

c) 2,4,6-Triiodo-5-(2,5-diaza-16-dioxoheptane-1,7-diyl-{10-[1,4,7,10-tetraazacyclododecanyl]})-aminoisophthalic acid-N,N-bis-(3-aza-4-oxopentane-1,5-diyl-{10-[1,4,7,10-tetraazacyclododecanyl]})-amide 25.7 g (10 mmol) of 2,4,6-triiodo-5-(2,5-diaza-1,6-dioxoheptane-1,7-diyl-{10-[1,4,7-tris-(benzyloxycarbonyl)-1,4,7,10-tetraazacyclododecanyl]})-aminoisophthalic acid-N,N-bis-(3-aza-4-oxopentane-1,5-diyl-{10-[1,4,7-tris-(benzyloxycarbonyl)-1,4,7,10-tetraazacyclododecanyl]})-amide is carefully mixed at 0–5° C. [with] 140 ml of HBr/AcOH (33%) and stirred for 3 hours at room temperature. Then, the reaction mixture is poured into 800 ml of diethyl ether, the solid that accumulates in this case is suctioned off and rewashed several times with diethyl ether. The residue is dissolved in 100 ml of water and 100 ml of dichloromethane while being stirred vigorously, and 32% NaOH solution is added until a pH of 10 is reached. The organic phase is separated, the aqueous phase is extracted three times with 50 ml each of dichloromethane, the combined organic phases are dried on magnesium sulfate and evaporated to the dry state.

Yield: 12.8 g (94% of theory) of a colorless solid Elementary analysis: Cld.: C, 39.57; H, 6.05; N, 19.48; I, 27.87. Fnd.: C, 39.71; H, 5.99; N, 19.56; I, 27.61.

d) 2,4,6-Triiodo-5-(2,5-diaza-1,6-dioxoheptane-1,7-diyl-{10-[1,4,7-tris-(carboxymethyl)-1,4,7,10-tetraazacyclododecanyl]})-aminoisophthalic acid-N,N-bis-(3-aza-4-oxopentane-1,5-diyl-{10-[1,4,7-tris-(carboxymethyl)-1,4,7,10-tetraazacyclododecanyl]})-amide 18.4 g (13.5 mmol) of 2,4,6-triiodo-5-(2,5-diaza-1,6-dioxoheptane-1,7-diyl-{10-[1,4,7,10-tetraazacyclododecanyl]})-aminoisophthalic acid-N,N-bis-(3-aza-4-oxopentane-1,5-diyl-{10-[1,4,7,10-tetraazacyclododecanyl]})-amide is dissolved in 75 ml of water, 19.5 g (206.5 mmol) of chloroacetic acid is added, and a pH of 9.5 is set at 60° C. with 32% NaOH. It is heated for 10 hours to 70° C., whereby the pH of the reaction mixture is readjusted continuously to 9.5. After cooling to room temperature, a pH of 1 is set with concentrated HCl, and the solution is concentrated by evaporation in a vacuum. The residue is absorptively precipitated with 250 ml of methanol, insoluble components are filtered out, and the filtrate is-concentrated by evaporation. The residue is dissolved in 100 ml of water and added to an ion-exchange column (600 ml, IR 120, H⁺-form). Then, it is washed with 2 l of water, and the acidic eluate is concentrated by evaporation. The residue is dissolved in 70 ml of methanol and added in drops in 900 ml of diethyl ether, the solid that accumulates in this case is suctioned off, rewashed several times with diethyl ether, and it is dried in a vacuum.

Yield: 14.3 g (56% of theory) of a colorless solid Elementary analysis: Cld.: C, 40.07; H, 5.34; N, 14.09; I, 20.16. Fnd.: C, 40.24; H, 5.31; N, 13.99; I, 19.98.

e) 2,4,6-Triiodo-5-(2,5-diaza-1,6-dioxoheptane-1,7-diyl-{10-[1,4,7-tris-(carboxylatomethyl)-1,4,7,10-tetraazacyclododecanyl, Gd complex]})-aminoisophthalic acid-N,N-bis-(3-aza-4-oxopentane-1,5-diyl-{10-[1,4,7-tris-(carboxylatomethyl)-1,4,7,10-tetraazacyclododecanyl, Gd complex]})-amide 13.0 g (6.9 mmol) of 2,4,6-triiodo-5-(2,5-diaza-1,6-dioxoheptane-1,7-diyl-{10-[1,4,7-tris-(carboxymethyl)-1,4,7,10-tetraazacyclododecanyl]})-aminoisophthalic acid-N,N-bis-(3-aza-4-oxopentane-1,5-diyl-{10-[1,4,7-tris-(carboxymethyl)-1,4,7,10-tetraazacyclododecanyl]})-amide is dissolved in 100 ml of water and acidified by adding 3 ml of acetic acid. 3.7 g (10.4 mmol) of gadolinium oxide is added, and it is refluxed for 6 hours. After complexing is completed, the pH is set at 7.4 with ammonia, and it is chromatographed on silica gel (mobile solvent:dichloromethane/methanol/ammonia: 10/10/1). The fractions that contain the product are combined and absorptively precipitated with 10 g of ion exchanger (IR 267 H-form) for 2 hours and filtered off, then, it is absorptively precipitated with 10 g of-ion exchanger (IRA 67 OH-form) for 2 hours, filtered off, mixed with 2 g of activated carbon, heated for 2 hours to 60° C., filtered off and freeze-dried.

Yield: 7.1 g (41% of theory) of a colorless solid Water content (Karl-Fischer): 6.3% Elementary analysis (relative to the anhydrous substance): Cld.: C, 32.19; H, 3.90; N, 11.32; I, 16.19; Gd, 20.07. Fnd.: C, 32.34; H, 3.91; N, 11.28; I, 16.07; Gd, 19.96.

PHARMACOLOGICAL EXAMPLES

CT Studies with Example 1B

By way of example, the suitability of the described compound class was examined in Example 1B with the aid of computer tomography (CT) of rats. For the CT studies, a Siemens Somatom CR was available. The 5-second image was prepared with a layer thickness of 2 mm and a tube voltage of 125 kV. Substance 1B was formulated as an aqueous solution at a concentration of 0.17 mol/l (corresponds to 145 mg (1+Gd)/ml.

Male Wistar rats (400 g of body weight) were scanned before (FIG. 1a) and after intravenous injection (FIG. 1) of 1B in a dose of 0.15 mmol/kg (corresponds to 127 mg of (I+Gd)/kg).

Despite the small size of the animal being examined, a very clear contrasting of the blood-conveying vessels (A) and the renal cortex (N) could itself be observed with the low dose of 127 mg of (I+Gd). This early phase reflects the blood perfusion of the renal cortex. As early as 15 minutes later in the parenchyma phase, the renal pelvis was contrasted, which can be attributed to a quick renal excretion of the substance (FIG. 2).

MRT Studies with Example 1B

The same substance (IB) was examined with the aid of magnetic resonance tomography (MRT) as a contrast medium.

The MRT studies were performed on a 1.5 T device (Siemens Symphonie with 40 mT/m gradients). 400 g Wistar rats were examined with T1-weighted image sequences (angiography TR 2.54 ms, TE 1.12 ms und α=40° or organ visualization TR 54 ms, TE 4.8 ms and α=40°). The angiography (MRA, FIG. 3) was from 0–60 seconds p.i., and the organ visualization (FIGS. 4a and b) was prepared 15 minutes after the injection. Substance 1B was formulated as an aqueous solution at a concentration of 0.17 mol/l (corresponds to 0.5 mol of Gd/l) and was intravenously injected in a dose of 0.03 mmol of substance or 0.1 mmol of Gd/kg.

The MRA has an excellent ability to visualize the large arteries (aorta, femoral artery) as well as the heart.

In the whole-body image (FIG. 4b), a clear contrasting of liver (L) as well as kidneys (renal pelvis=N) can be detected. The ureter (U) could also be visualized, which also emphasized the quick renal elimination of the substance.

This combined CT and MR study demonstrates the dual uses of this new compound class. Excellent contrast enhancement was demonstrated in CT and in MR. The clinical use of these compounds is conceivable, for example, in a high-resolution MultiSlice CT (visualization of the coronary vessels). After that, a delayed MRT is performed to evaluate the vitality of the myocardium. To this end, a second injection of a contrast medium is not necessary.

Phantom Studies with Example 3F in Comparison to Gadovist and Iopromilde

The relative X-ray attenuation of Example 3F was determined at concentrations of 0.05, 0.1 and 0.2 mol/l of substance, equivalent to 0.3, 0.6 and 1.2 mol/ of opacifying elements (Gd+iodine), compared to equimolar concentrations of iopromide and gadobutrol. To this end, a phantom was used, in which dilutions of the starting formulations (Example 3F-0.27M, Ultravist® 300 mg of I/ml equivalent to 0.788 mol/l of iopromide and gadobutrol 1 mol/l) in distilled water was pipetted into well-plates (Oster 3524). A milliliter of each dilution was pipetted in each case into a well-plate, which corresponded to a height of 0.5 cm. The finish-pipetted well-plate was positioned on the horizontal patient table of the C-arm x-ray device (stenoscope D6, General Electric) in the beam path, and above it, a plastic container with a 17-cm-water column was set on the well-plate to simulate soft-tissue absorption and radiation-hardening of the x-ray radiation as under in-vivo conditions.

The x-ray images were recorded in the "high pulse" modality with the DSM x-ray device stenoscope D6 (General Electric) with a cesium filter/iodine intensifier of 16 cm and a 2 mm aluminum filter with various voltages of the x-ray anode.

All images were recorded after manual selection of the anode voltage of x-ray tubes and variation of mA to optimize the image contrast in the respective anode voltage.

The images of stenoscope D6 were then transferred into an image-analyzing device (Quantimet 500+, Leica) and visualized on a scale of 256 gray-scale values. For quantitative gray-scale determination, a circular ROI⁻(region of interest) for each well was analyzed, and the background was subtracted in the respective anode voltage.

The measured gray values of Example 3F, iopromide and gadobutrol, were applied against the respective concentration and a linear regional analysis was performed. The increase in compensating lines was calculated in this case, and the ratio of straight lines between the various contrast media was determined.

Representative x-ray images of the above-described phantom are visualized in FIG. 5.

The ratio between the concentrations of Example 3F, iopromide and gadobutrol was linear in all cases. The evaluation showed a significantly higher x-ray absorption of Example 3F than iopromide and gadobutrol at equimolar concentrations (FIG. 5).

In the evaluation of x-ray images, Example 3F showed a 3.08×-higher x-ray absorption than iopromide and a 3.77×-higher x-ray absorption than gadobutrol with 110 kV and equimolar concentrations. Still higher differences in the x-ray absorption of Example 3F can be expected for higher anode voltages, as they are used in modern x-ray CT-processes (helicoidal and mult-line CT). Radiation hardening that occurs in addition under in-vivo conditions promotes additional elements, such as, e.g., Gd, Dy, Yb or Bi.

The phantom studies confirm that Example 3F has an excellent x-ray absorption and is suitable for use in modern DSA and CT, especially multi-line CT.

Distribution Coefficient

The distribution coefficient of Example 3F was determined in comparison to Gadovist, iopromide and iotrolan in 1-butanol and tris-HCl buffer at pH 7.6. The contrast media were dissolved in the buffer at a final concentration of 0.1 mmol of Gd/l, and the iodine-containing contrast media were used with a starting concentration of 1 mg of I/ml.

TABLE 1

Distribution Coefficient of Example 3F in Comparison to Commercially Available MR- and X-ray Contrast Media

| Substance | Distribution Coefficient of Butanol/Water |
|---|---|
| Example 3F | 0.0002 ± 0.0001 |
| Gadobutrol | 0.006 ± 0.0007 |
| Iopromide | 0.051 ± 0.003 |
| Iotrolan | 0.0065 ± 0.002 |

The data in Table 1 confirm that Example 3F is a very hydrophilic substance with a low distribution coefficient of butanol/water and has even better values than the very well-tolerated MR-contrast medium Gadovist. In comparison to this, the commercially available iodine-containing compound Iopromide has a much lower hydrophilia with up to a 255×-higher distribution coefficient of butanol/water (0.051 vs. 0.0002).

IC-50/LD-50 Correlation

To determine the IC-50, the neutral red test was used in epithelial cells of the distal renal tubule. In addition, this test is very helpful for predicting with high accuracy the LD-50 values of newly synthesized compounds.

Epithelial cell line MDCK of the renal distal renal tubule of a canine kidney (ECACC No. 85011435) was incubated from 10,000 cells/well in Alpha MEM Eagle (10% fetal bovine serum) at 37° C. and 5% $CO_2$, 95% atmospheric humidity for 20 hours with various Examples 1B, 3F and 5F. Neutral red was used as an indicator for cell viability and for measuring lyosomal integrity and employed to determine those contrast medium concentrations in which a 50% reduction of cell viability (IC-50) occurred after 24 hours.

Four independent replicates were tested for each concentration of contrast medium. The results are summarized in Table 2. Compared to the reference compound for MR contrast media, Gadovist showed a strong increase in compatibility. The latter is a reference compound in clinical practice and a contrast medium with proven excellent compatibility. The highest compatibility was found for Example 3F with 1170 μmol of I eq/ml.

TABLE 2

Comparison of $IC_{50}$ Values of Different Examples According to the Invention with Gadobutrol as well as the $LD_{50}$ Value to be Expected in Mice.

| Substance | $IC_{50}$ μmol of I eq/ml | "Expected" $LD_{50}$ of Mice ($r^2$: 0.93) mmol of I eq/kg |
|---|---|---|
| Gadovist | 153 | 32 |
| Example 1B | 930 | 165 |
| Example 3F | 1170 | 195 |
| Example 5G | 788 | 143 |

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosure of all applications, patents and publications, cited herein and of corresponding German application No. 10307759.6, filed Feb. 19, 2004, and U.S. Provisional Application Ser. No. 60/452,053, filed Mar. 6, 2003 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

BRIEF DESCRIPTION OF DRAWINGS

FIG. 1 Illustrates Male Wistar rats which were scanned before (FIG. 1a) and after intravenous injection (FIG. 1b) of 1B in a dose of 0.15 mmol/kg (corresponds to 127 mg of (I=Gd)/kg).

FIG. 2 Illustrates CT Image of a Rat 15 Minutes after I.V. Injection of IB.

FIG. 3 Illustrates IVIRA 7.5 Seconds After I.V. Injection of IB in Rats.

FIG. 4 Illustrates baseline organ visualization (FIG. 4a) and organ visualization that was prepared 15 minutes after the injection (FIG. 4b).

FIG. 5 Illustrates comparison of X-ray Absorption of Example 3F, Gadobutrol and Iopromide X-ray images of the phantom at 60 and 110 kV anode voltage are recorded with the C-arm device stenoscope D6.

FIG. 6 Illustrates relative X-ray Absorption of Example 3F in Comparison with Gadobutrol and Iopromide at Various Anode Voltages of X-ray Tubes.

The invention claimed is:
1. A metal complex of formula I

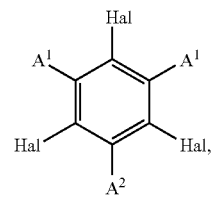

in which
Hal stands for bromine or iodine,
$A^1$ stands for —CONR$^1$—(CH$_2$)$_n$—NR$^2$—(CO—CHZ$^1$-NH)$_m$—CO—CHZ$^2$-*, —CONR$^1$—(CH$_2$)$_p$—(CONR$^2$CH$_2$)$_m$—CHOH—CH$_2$—*, —CH$_2$O—(CH$_2$)$_p$—CHOH—CH$_2$—*, —CH$_2$—O—(CH$_2$)$_n$—NR$^1$—(CO—CHZ$^1$-NH)$_m$—CO—CHZ$^2$-*, or —CH$_2$—NR$^1$—CO—(CHZ$^1$-NH—CO)$_m$—CHZ$^2$-*,
$A^2$ independently has the same meaning as $A^1$ or in the case that $A^1$ has the meaning first mentioned above can also stand for the radical-NR$^1$—CO—(NR$^1$)$_m$—(CH$_2$)$_p$—NR$^2$—(CO—CHZ$^1$-NH)$_m$—CO—CHZ$^2$-*,
* designates the binding site to K,
$R^1$ and $R^2$ mean, independently of one another, a hydrogen atom, $C_1$–$C_2$-alkyl group or a monohydroxy-$C_1$–$C_2$-alkyl group,
$Z^1$ and $Z^2$ mean, independently of one another, a hydrogen atom or a methyl group,
n means the number 2–4,
m means the number 0 or 1 and
p means the number 1–4,
K stands for a macrocyclic compound of formula $I_a$

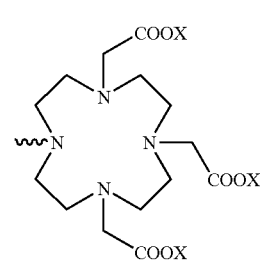

with X meaning a hydrogen atom or a metal ion equivalent of atomic numbers 20–29, 39, 42, 44 or 57–83, provided that at least two X stand for metal ion equivalents, and optionally present free carboxy groups optionally are present as salts of organic and/or inorganic bases or amino acids or amino acid amides.

2. A metal complex according to claim 1, characterized in that $A^1$ stands for
—CONH(CH$_2$)$_{2;3}$NHCOCH$_2$NHCOCH(CH$_3$)—,
—CONH(CH$_2$)$_{2;3}$NHCOCH$_2$NHCOCH$_2$—, —CONH(CH$_2$)$_{2;3}$NHCOCH$_2$—, —CONH(CH$_2$)$_{2;3}$NHCOCH(CH$_3$)—, —CONHCH$_2$CH(OH)CH$_2$—, —CON(CH$_3$)CH$_2$CH(OH)CH$_2$—, —CH$_2$OCH$_2$CH(OH)CH$_2$—, —CONHCH$_2$CONHCH$_2$CH(OH)CH$_2$—, —CH$_2$NHCOCH$_2$—, —CH$_2$NHCOCH(CH$_3$)—, —CH$_2$NHCOCH$_2$NHCOCH$_2$—, —CH$_2$NHCOCH$_2$NHCOCH(CH$_3$)—, —CH$_2$O(CH$_2$)$_2$ NHCOCH$_2$—, —CON(CH$_2$CH$_2$OH) CH$_2$CH$_2$NHCOCH$_2$—, or —CH$_2$O(CH$_2$)$_2$N(CH$_2$CH$_2$OH)COCH$_2$—.

3. A metal complex according to claim 1, wherein A$^2$ stands for
—NHCOCH$_2$NHCOCH$_2$NHCOCH(CH$_3$)—,
—NHCOCH$_2$NHCOCH$_2$NHCOCH$_2$—,
—NHCOCH$_2$NHCOCH$_2$—, —NHCOCH$_2$NHCOCH(CH$_3$)—, —N(CH$_3$)COCH$_2$NHCOCH$_2$—, —NHCONH(CH$_2$)$_2$NHCONH$_2$—, —NHCOCH$_2$N(CH$_2$CH$_2$OH)COCH$_2$—, or —N(CH$_3$)COCH$_2$N(CH$_2$CH$_2$OH)COCH$_2$—.

4. A metal complex according to claim 1, wherein at least one X stands for a metal ion equivalent of atomic numbers 21–29, 42, 44, or 58–70.

5. A metal complex according to claim 4, wherein at least one X stands for a metal ion equivalent of the ions gadolinium(III), dysprosium(III), europium(III), iron(III) or manganese(II).

6. A pharmaceutical composition that contains at least one metal complex according to claim 1 and one or more additives suitable for use in a galenical formulation.

7. A method of x-ray diagnosis comprising administering to a patient at least one metal complex according to claim 1 and performing x-ray diagnosis.

8. A method of MRT diagnosis comprising administering to a patient at least one metal complex according to claim 4 for and performing MRT diagnosis.

9. A pharmaceutical composition that contains a metal complex according to claim 1 in a molar ratio of 2000:1 to 1:1.

10. A pharmaceutical composition according to claim 6, wherein said at least one metal complex is dissolved or suspended in water or in a physiologically acceptable salt solution at a concentration of 0.001 to 1 mol/l.

11. A method for x-ray diagnosis or MR diagnosis of a cerebral infarction, a tumor of the liver, a space-occupying process in the liver, a tumor of the abdomen, a kidney, a muscle-skeleton system, or a blood vessel, comprising administering to a patient at least one metal complex according to claim 1, and performing x-ray diagnosis or MR diagnosis.

12. A process for preparing a metal complex according to claim 1, comprising
a) reacting a triiodo- or tribromoaromatic compound of formula II

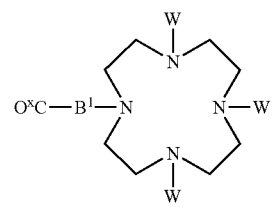

(II)

with a macrocyclic compound of formula III

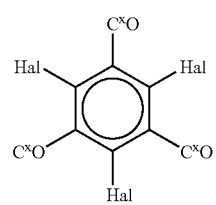

(III)

in which
C$^x$O stands for a —COOH— or activated carboxyl group,
W stands for a protective group or a —CH$_2$COOX' group with X' in the meaning of X as defined in claim 1 or a protective group and —Y$^1$—NR$^1$—CO—B$^1$—, which forms upon reaction of a Y$^1$NHR$^1$ group of a compound of formula II with the O$^x$CB$^1$— group of a compound of formula III, stands for the radical A$^1$ in the meaning of —CO—NR$^1$—(CH$_2$)$_n$—NR$^2$—(CO—CHZ$^1$-NH)$_m$—CO—CHZ$^2$- or —CH$_2$—O—(CH$_2$)$_n$—NR$^1$—(CO—CHZ$^1$-NH)$_m$—CO—CHZ$^2$- and —Y$^2$—NR$^1$—CO—B$^1$—, which forms upon reaction of the Y$^2$NHR$^1$ group of a compound of formula II with the O$^x$CB$^1$— group of a compound of formula III, stands for —Y$^1$—NR$^1$—CO—B$^1$— or for the case that —Y$^1$—NR$^1$—CO—B$^1$— has the meaning first mentioned above, the latter also stands for —NR$^1$—CO—(NR$^1$)$_m$(CH$_2$)$_p$—NR$^2$—(CO—CHZ$^1$-NH)$_m$—CO—CHZ$^2$-,
and then optionally removing protective group W and introducing the radical CH$_2$COOX, or optionally removing the protective group that stands for X' and then reacting with a metal oxide or metal salt of an element of atomic numbers 20–29, 39, 42, 44 or 57–83, or b) reacting a triiodo- or tribromoaromatic compound of formula IV

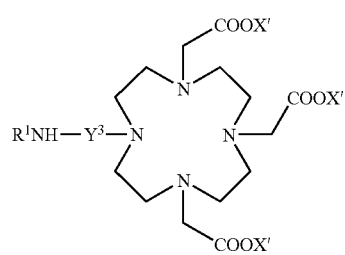

(IV)

with a macrocyclic compound of formula V

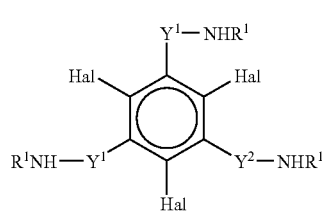

(V)

in which —C$^x$O and X' have the above-mentioned meaning and —CO—NR$^1$—Y$^3$—, which forms upon reaction of the $Y^3NHR^1$ group of a compound of formula V with the $O^xC$— group of a compound of formula IV, stands for radical $A^1$ in the meaning of —$CONR^1$—$(CH_2)_p$—$(CONR^2CH_2)_m$—CH(OH)CH$_2$—, and then optionally removing the protective group that stands for X' and then reacting with a metal oxide or metal salt of an element of atomic numbers 20–29, 39, 42, 44 or 57–83, or c) reacting a triiodo- or tribromoaromatic compound of formula VI

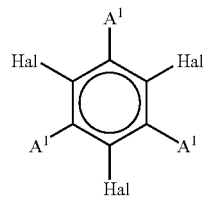
(VI)

in which
A$^1$ stands for a radical

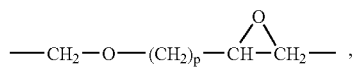

with a cyclene of formula VII

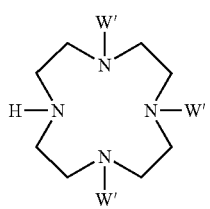
(VII)

in which W' stands for a hydrogen atom or a protective group, removing the optionally present protective groups and then introducing radical —CH$_2$COOX to form a metal complex of formula I with A in the meaning of radical —CH$_2$—O—(CH$_2$)$_p$—CHOH—CH$_2$—, or d) reacting a triiodo- or tribromoaromatic compound of formula VIII

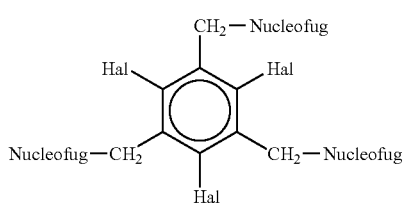
(VIII)

[Nucleofug = nucleofuge]

in which Nucleofuge stands for a nucleofuge group, with a macrocyclic compound of formula IX

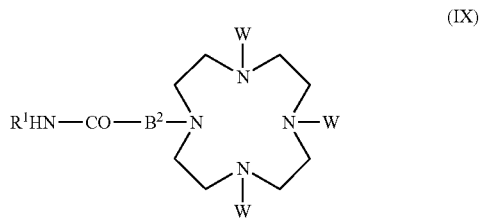
(IX)

in which
R$^1$ and W have the above-mentioned meanings, and B$^2$ stands for the radical —(CHZ$^1$-NHCO)$_m$—CHZ$^2$, and then further processing as indicated under a), such that metal complexes of formula I are obtained with A$^1$ in the meaning of radical —CH$_2$—NR$^1$—CO—(CHZ$^1$-NHCO)$_m$—CHZ$^2$, then in the metal complexes, obtained according to a)–d), of formula I, still present acid hydrogen atoms are optionally substituted by cations of inorganic or organic bases, amino acids or amino acid amides.

13. A process for preparing a pharmaceutical composition according to claim 6, comprising bringing into a composition said at least one metal complex and the one or more additives suitable for use in a galenical formulation.

14. A pharmaceutical composition according to claim 6, which is in a suitable form for enteral or parenteral administration.

15. A metal complex according to claim 1, wherein A$^1$ stands for
—CONH(CH$_2$)$_{2;3}$NHCOCH$_2$NHCOCH(CH$_3$)—,
—CONH(CH$_2$)$_{2;3}$NHCOCH$_2$NHCOCH$_2$)—,
—CONH(CH$_2$)$_{2;3}$NHCOCH$_2$)—, —CONH(CH$_2$)$_{2;3}$NHCOCH(C$_3$)—, —CONHCH$_2$CH(OH)CH$_2$—,
—CON(CH$_3$)CH$_2$CH(OH)CH$_2$—, —CH$_2$OCH$_2$CH(OH)CH$_2$—, —CONHCH$_2$CONHCH$_2$CH(OH)CH$_2$—, —CH$_2$NHCOCH$_2$—, —CH$_2$NHCOCH(CH$_3$)—, —CH$_2$NHCOCH$_2$NHCOCH$_2$—, —CH$_2$NHCOCH$_2$NHCOCH(CH$_3$)—, —CH$_2$O(CH$_2$)$_2$NHCOCH$_2$—, or —CH$_2$O(CH$_2$)$_2$N(CH$_2$CH$_2$OH)COCH$_2$—.

16. A metal complex according to claim 1, wherein A$^2$ stands for
—NHCOCH$_2$NHCOCH$_2$NHCOCH(CH$_3$)—,
—NHCOCH$_2$NHCOCH$_2$NHCOCH$_2$—,
—NHCOCH$_2$NHCOCH$_2$—, —NHCOCH$_2$NHCOCH(CH$_3$)—, —N(CH$_3$)COCH$_2$NHCOCH$_2$—, —NHCOCH$_2$N(CH$_2$CH$_2$OH)COCH$_2$—, or —N(CH$_3$)COCH$_2$N(CH$_2$CH$_2$OH)COCH$_2$—.

17. A process according to claim 12, wherein the nucleofuge group is
F, Cl, Br, I, —OTs, —OMs, OH,

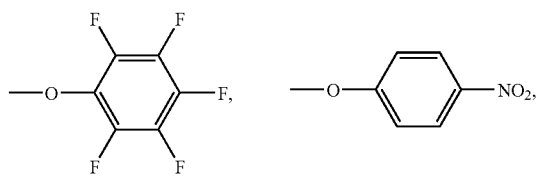

-continued
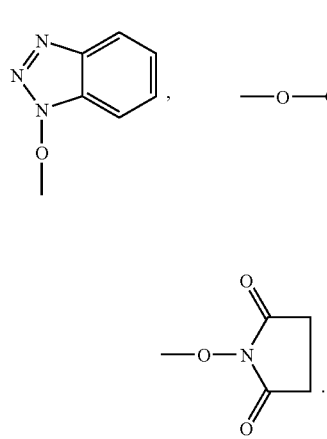
18. A pharmaceutical composition that contains a metal complex according to claim 1 in a molar ratio of 49:1 to 4:1.
19. A process according to claim 12, wherein the nucleofuge group is
F, Cl, Br, I, OH,
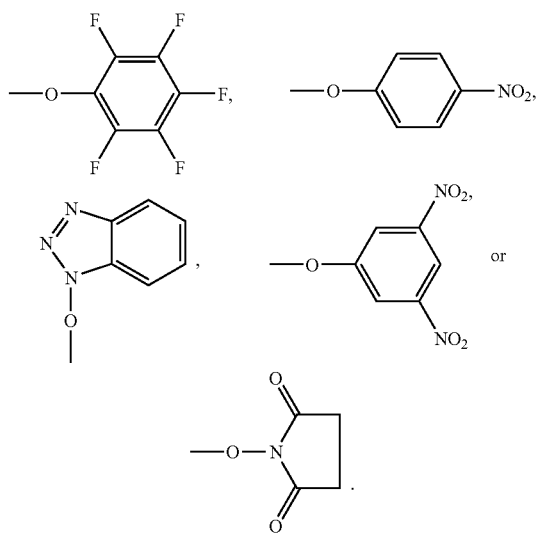
* * * * *

UNITED STATES PATENT AND TRADEMARK OFFICE
CERTIFICATE OF CORRECTION

PATENT NO. : 7,208,140 B2
APPLICATION NO. : 10/780887
DATED : April 24, 2007
INVENTOR(S) : Heiko Schirmer et al.

Page 1 of 1

It is certified that error appears in the above-identified patent and that said Letters Patent is hereby corrected as shown below:

Column 54, diagram:    $1^{st}$ " $A^1$ " should read -- $KA^1$ -- line 7
                                    $2^{nd}$ " $A^2$ " should read -- $A^2K$ -- line 12
                                    $3^{rd}$ " $A^1$ " should read -- $A^1K$ -- line 7

Column 54, line 57, reads "characterized in that" should read -- wherein --

Column 55, line 11, reads "$NHCONH_2$" should read -- $NHCOCH_2$ --

Column 55, line 19, delete "the ions".

Signed and Sealed this

Twenty-third Day of October, 2007

JON W. DUDAS
*Director of the United States Patent and Trademark Office*